(12) United States Patent
Inchauspe et al.

(10) Patent No.: US 8,293,528 B2
(45) Date of Patent: *Oct. 23, 2012

(54) PEPTIDE COMPOSITIONS AND THEIR USE IN PARTICULAR IN THE PREPARATION OF PHARMACEUTICAL COMPOSITIONS ACTIVE AGAINST THE HEPATITIS C VIRUS

(75) Inventors: Geneviève Inchauspe, Lyons (FR); Anne Fournillier, Lyons (FR); Nourredine Himoudi, Lyons (FR); Perrine Martin, Decines Charpieu (FR)

(73) Assignees: Transgene SA, Illkirch-Graffenstaden (FR); INSERM (Institut National de la Sante et de la Reserche Medicale), Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 12/653,751

(22) Filed: Dec. 17, 2009

(65) Prior Publication Data

US 2011/0020398 A1    Jan. 27, 2011

Related U.S. Application Data

(63) Continuation of application No. 11/503,245, filed on Aug. 11, 2006, now abandoned, which is a continuation-in-part of application No. 10/514,762, filed as application No. PCT/FR03/01478 on May 15, 2003, now Pat. No. 7,393,831.

(30) Foreign Application Priority Data

May 17, 2002  (FR) ..................................... 02 06111

(51) Int. Cl.
*C12N 15/63* (2006.01)
*A48K 39/29* (2006.01)

(52) U.S. Cl. ............... 435/320.1; 424/189.1; 424/192.1; 424/199.1; 424/93.1; 536/23.72

(58) Field of Classification Search ........................ None
See application file for complete search history.

(56) References Cited

U.S. PATENT DOCUMENTS

| | | | |
|---|---|---|---|
| 5,106,726 A | 4/1992 | Wang | |
| 5,436,126 A | 7/1995 | Wang | |
| 5,582,968 A | 12/1996 | Wang et al. | |
| 5,639,594 A | 6/1997 | Wang et al. | |
| 5,683,864 A | 11/1997 | Houghton et al. | |
| 5,712,087 A | 1/1998 | Houghton et al. | |
| 5,736,321 A | 4/1998 | Hosein et al. | |
| 5,747,239 A | 5/1998 | Wang et al. | |
| 6,150,087 A | 11/2000 | Chien | |
| 6,312,889 B1 | 11/2001 | Houghton et al. | |
| 6,346,375 B1 | 2/2002 | Chien | |
| 6,534,482 B1 | 3/2003 | Fikes et al. | |
| 6,562,346 B1 | 5/2003 | Paliard et al. | |
| 6,635,257 B1 | 10/2003 | Depla et al. | |
| 7,393,831 B2 | 7/2008 | Fournillier et al. | |
| 7,695,960 B2 * | 4/2010 | Inchauspe et al. | 435/320.1 |
| 2002/0115061 A1 | 8/2002 | Chisari et al. | |
| 2003/0095980 A1 | 5/2003 | Maertens et al. | |
| 2003/0118603 A1 | 6/2003 | Maertens et al. | |
| 2003/0194747 A1 | 10/2003 | Georges et al. | |
| 2003/0202987 A1 | 10/2003 | Depla et al. | |
| 2003/0203869 A1 | 10/2003 | Fikes et al. | |
| 2007/0020285 A1 | 1/2007 | Fournillier et al. | |
| 2007/0072176 A1 | 3/2007 | Inchauspe et al. | |

FOREIGN PATENT DOCUMENTS

| | | |
|---|---|---|
| EP | 0388232 A1 | 9/1990 |
| EP | 0450931 A1 | 4/1991 |
| EP | 0468527 A2 | 7/1991 |
| EP | 0452931 A2 | 4/1994 |
| EP | 1506225 B1 | 7/2006 |
| WO | WO 93/00365 A1 | 1/1993 |
| WO | WO 94/20127 A1 | 9/1994 |
| WO | WO 99/58658 A2 | 11/1999 |
| WO | WO 99/67285 A1 | 12/1999 |
| WO | WO 01/21189 A1 | 3/2001 |
| WO | WO 01/30812 A3 | 5/2001 |
| WO | WO 01/90197 A1 | 11/2001 |
| WO | WO 01/92311 A2 | 12/2001 |
| WO | WO 02/070006 A2 | 9/2002 |
| WO | WO 03/097677 A2 | 11/2003 |

OTHER PUBLICATIONS

U.S. Appl. No. 12/132,321, filed Jun. 3, 2008, Fournillier et al.
U.S. Appl. No. 12/211,385, filed Sep. 16, 2008, Fournillier et al.
Abrams et al., "Generation of Stable CD4/ and CD8/ T Cell Lines from Patients Immunized with ras Oncogene-Derived Peptides Reflecting Codon 12 Mutations," Cell. Immunol. 182:137-151, 1997.
Battegay et al., "Patients with Chronic Hepatitis C have Circulating Cytotoxic T Cells which Recognize Hepatitis C Virus-Encoded Peptides Binding to HLA-A2.1 Molecules," J. Virol. 69:2462-2470, 1995.
Brinster et al., "Different Hepatitis C Virus Nonstructural Protein 3 (Ns3)-DNA-Expressing Vaccines Induce in HLA-A2.1 Transgenic Mice Stable Cytotoxic T Lymphocytes that Target One Major Epitope," Hepatology 34:1206-1217, 2001. Chang et al., "Identification of HLA-A3 and -B7-Restricted CTL Response to Hepatitis C Virus in Patients with Acute and Chronic Hepatitis C," J. Immunol. 162:1156-1164, 1999.
Chang et al., "Immunological Significance of Cytotoxic T Lymphocyte Epitope Variants in Patients Chronically Infected by the Hepatitis C Virus," J. Clin. Invest. 100:2376-2385, 1997.
Day et al., "Broad Specificity of Virus-Specific CD4+ T-Helper-Cell Responses in Resolved Hepatitis C Virus Infection," J. Virology 76:12584-12595, 2002.
Definition of "epitope," in Immunobiology, 4th Edition, p. 600, 1999.
Diepolder et al., "Immunodominant CD4+ T-Cell Epitope within Nonstructural Protein 3 in Acute Hepatitis C Virus Infection," J. Virol. 71:6011-6019, 1997.
Fournillier et al., "Primary and Memory T Cell Responses Induced by Hepatitis C Virus Multiepitope Long Peptides," Vaccine 24:3153-3164, 2006.
Fytili et al., "Cross-Genotype-reactivity of the Immunodominant HCV CD8 T-Cell Epitope NS3-1073," Vaccine, 2008.

(Continued)

*Primary Examiner* — Bao Li
(74) *Attorney, Agent, or Firm* — Clark & Elbing LLP

(57) ABSTRACT

The invention relates to peptide compositions for use in the preparation of pharmaceutical compositions against hepatitis C virus, as well as corresponding methods.

8 Claims, 15 Drawing Sheets

OTHER PUBLICATIONS

Heile et al., "Evaluation of Hepatitis C Virus Glycoprotein E2 for Vaccine Design: an Endoplasmic Reticulum-Retained Recombinant Protein is Superior to Secreted Recombinant Protein and DNA-Based Vaccine Candidates," J. Virol. 74:6885-6892, 2000.

Himoudi et al., "Comparative Vaccine Studies in HLA-A2.1-Transgenic Mice Reveal a Clustered Organization of Epitopes Presented in Hepatitis C Virus Natural Infection," J. Virol. 76:12735-12746, 2002.

Ibe et al., "Identification and Characterization of a Cytotoxic T Cell Epitope of Hepatitis C Virus Presented by HLA-B*3501 in Acute Hepatitis," J. Gen. Virol. 79:1735-1744, 1998.

Kato et al., "Molecular Cloning of the Human Hepatitis C Virus Genome from Japanese Patients with Non-A, Non-B Hepatitis," Proc. Natl. Acad. Sci. U.S.A. 87:9524-9528, 1990.

Koziel et al., "Hepatitis C Virus (HCV)-Specific Cytotoxic T Lymphocytes Recognize Epitopes in the Core and Envelope Proteins of HCV," J. Virol. 67:7522-7532, 1993.

Lamonaca et al., "Conserved Hepatitis C Virus Sequences are Highly Immunogenic for CD4+ T Cells: Implications for Vaccine Development," Hepatology 30:1088-1098, 1999.

Lechner et al., "Of Successful Immune Responses in Persons Infected with Hepatitis C Virus," J. Exp. Med. 191:1499-1512, 2000.

Leroux-Roels, "Development of Prophylactic and Therapeutic Vaccines Against Hepatitis C Virus," Exp. Rev. Vaccines 4:351-371, 2005.

Manns et al., "The Way Forward in HCV Treatment-Finding the Right Path," Nat. Rev. Drug. Discov. 6:991-1000, 2007.

Martin et al., "A Vector-Based Minigene Vaccine Approach Results in Strong Induction of T-cell Responses Specific of Hepatitis C Virus," Vaccine 26:2471-2481, 2008.

Martin et al., "Genetic Immunization and Comprehensive Screening Approaches in HLA-A2 Transgenic Mice Lead to the Identification of Three Novel Epitopes in Hepatitis C Virus NS3 Antigen," J. Med. Virol. 74:397-405, 2004.

Pancholi et al., "DNA Immunization with Hepatitis C Virus (HCV) Polycistronic Genes or Immunization by HCV DNA Priming-Recombinant Canarypox Virus Boosting Induces Immune Responses and Protection from Recombinant HCV-Vaccinia Virus Infection in HLA-A2.1-Transgenic Mice," J. Virology 77:382-390, 2003. Abstract only.

Pascolo et al., "HLA-A2.1-Restricted Education and Cytolytic Activity of $CD8^+$ T Lymphocytes from $\beta2$ Microglubulin ($\beta2m$) HLA-A2.1 Monochain Transgenic $H-2D^b$ $\beta2m$ Double Knockout Mice," J. Exp. Med. 185:2043-2051, 1997.

Puig et al., "CD4+ Immune Escape and Subsequent T-Cell Failure Following Chimpanzee Immunization Against Hepatitis C Virus," Hepatology 44:736-743, 2006.

Qiao et al., "Hepatitis C Virus-Like Particles Combined with Novel Adjuvant Systems Enhance Virus-Specific Responses," Hepatology 37:52-59, 2003. Abstract only.

Racanelli et al., "Dendritic Cells Transfected with Cytopathic Self-Replicating RNA Induce Crossprinting of CD8+ T Cells and Antiviral Immunity," Immunity 20:47-58, 2004. Abstract only.

Rollier et al., "Control of Heterologous Hepatitis C Virus Infection in Chimpanzees is Associated with the Quality of Vaccine-Induced Peripheral T-Helper Immune Response," J. Virol. 78:187-196, 2004.

Rudikoff et al., "Single Amino Acid Substitution Altering Antigen-Binding Specificity," Proc. Natl. Acad. Sci. U.S.A. 79:1979-1983, 1982.

Shirai et al., "An Epitope in Hepatitis C Virus Core Region Recognized by Cytotoxic T Cells in Mice and Humans," J. Vriol. 68:3334-3342, 1994.

Simon et al., "DNA Vaccination Protects Mice Against Challenge with *Listeria monocytogenes* Expressing the Hepatitis C Virus NS3 Protein," Infect. Immun. 71:6372-6380, 2003.

Spaulding et al., "Analysis of Murine CD8(+) T-cell Clones Specific for the Dengue Virus NS3 Protein: Flavivirus Cross-Reactivity and Influence of Infecting Serotype," J. Virology 73:398-403, 1999.

Sutter et al., "Nonreplicating Vaccinia Vector Efficiently Expresses Recombinant Genes," Proc. Natl. Acad. Sci. U.S.A. 89:10847-10851, 1992.

Tabatabai et al., "Functionally Distinct T-Cell Epitopes within the Hepatitis C Virus Non-Structural 3 Protein," Human Immunology 60:105-115, 1999.

Ward et al., "Cellular Immune Responses Against Hepatitis C Virus: The Evidence Base 2002," Clin. Exp. Immunol. 128:195-203, 2002.

Wedemeyer et al., "Cross-Reactivity Between Hepatitis C Virus and Influenza A Virus Determinant-Specific Cytotoxic T Cells," J. Virology 75:11392-11400, 2001. Abstract only.

Wedemeyer et al., "Oral Immunization with HCV-NS3-Transformed *Salmonella*: Induction of HCV-Specific CTL in a Transgenic Mouse Model," Gastroenterology 121:1158-1166, 2001. Abstract only.

Wertheimer et al., "Novel $CD4^+$ and $CD8^+$ T-cell Determinants Within the NS3 Protein in Subjects with Spontaneously Resolved HCV Infection," Hepatology 37:577-589, 2003.

Wong et al., "Liver-Derived CTL in Hepatitis C Virus Infection: Breadth and Specificity of Responses in a Cohort of Persons with Chronic Infection," J. Immunol. 160:1479-148, 1998.

"Annex 1: Additional Results Submitted by the Inventors" filed with the European Patent Office for European Patent Application No. EP 03752815.5 on Jan. 14, 2008.

International Preliminary Examination Report for PCT/FR03/01478, Oct. 28, 2004 (and English language translation thereof).

International Search Report for PCT/FR03/01478, Nov. 11, 2003.

Substantive prosecution documents from U.S. Appl. No. 10/514,762, filed Nov. 16, 2004 (now U.S. Patent No. 7,393,831).

Substantive prosecution documents from U.S. Appl. No. 11/503,245, filed Aug. 11, 2006.

* cited by examiner

Figure 2

Shimotono:

```
STKVPAAYAAQGYKVRVLNPSVAATLGFGAYMSKAHGIEPNIRTGV
```

1a:

```
---------------L--------------------D-------    50%  (7/14)
---------------L-------------------VD-------    50%  (7/14)
```

1b: /135

```
STKVPAAYAAQGYKVRVLNPSVAATLGFGAYMSKAHGIEPNIRTGV
---------------L-------------------VD-------    29%   (39/135)
---------------L--------------------D-------    28%   (38/135)
---------------L-------------------TD-------     6%   (9/135)
---------------L-----------------Y-TD-------     6%   (8/135)
---------------L----------------------------     4%   (6/135)
---------------L---------S---------TD-------     4%   (5/135)
---------------L----------------Y--D--V----   1,5%   (2/135)
--------------------------------------------   1,5%   (2/135)
---------------L-------------------T--------   1,5%   (2/135)
-N---VE--------L-------------------VD-------   1,5%   (2/135)
---------------L------T------------VD-------   1,5%   (2/135)
---------G-----L--------------------D-------   1,5%   (2/135)
---------------L---------S----------D-------   1,5%   (2/135)
--R------------L--------------------D--L----   1,5%   (2/135)
--------T------L-------------------TD-------   1,5%   (2/135)
---------------L--------------------D--V----   1,5%   (2/135)
---------------L---------S---------VD-S-----   1,5%   (2/135)
---------------L-------------------VD---S---   0,8%   (1/135)
---------------L-----------------Y-TD--V----   0,8%   (1/135)
--------T------L---------S-------Y-MD--L----   0,8%   (1/135)
---------------L---------S---------VD-----    0,8%   (1/135)
---------------L---------S-------Y-VD-------   0,8%   (1/135)
--R------------L-------------------TD-------   0,8%   (1/135)
--R------------L---------S-------Y-VD-------   0,8%   (1/135)
--R------------L----------T------Y-TD-------   0,8%   (1/135)
```

4:

```
STKVPAAYAAQGYKVRVLNPSVAATLGFGAYMSKAHGIEPNIRTGV
-------H-------L-------------V-----Y--D----S--  100%  (1/1)
```

Figure 3A

Shimotono:

APITAYSQQTRGLLGCIITSLTGRDKNQVDGEVQVLSTATQSFLATCVNGVCWTVYHGAGSKT

4: /1
```
------X------FST---------T-ENC--------------G-A----M--------A--  100%(1/1)
```

Figure 4

Shimotono:
NFITGIQYLAGLSTLPGNPAIASLMAFTASITSPLTTQNTLLFNILGGWVAAQLAPP

1a:

```
---S-------------------------AV------SQ---------------A-  50% (7/14)
---S-------------------------AV------GQ---------------A-  43% (6/14)
---S-T-----------------------AV------SQ---------------A-   7% (1/14)
```

1b:

NFITGIQYLAGLSTLPGNPAIASLMAFTASITSPLTTQNTLLFNILGGWVAAQLAPP
```
---S----------------------------------H-----------------35%(48/139)
---S----------------------------------S-----------------18%(25/139)
---S----------------------------------------------------16%(22/139)
---S----------------------------------------------------  6%(9/139)
---S----------------------------------Y-----------------  6%(8/139)
---S----------V-----------------------H-----------------  2%(3/139)
---S-------------------------V--------------------------  2%(3/139)
---S-------------------------V--------S-----------------  2%(3/139)
---S---------------------------------T--M---------------1,5%(2/139)
---S--------------------------V-------Y-------------I---1,5%(2/139)
---S---------------R-P----------------H-----------------1,5%(2/139)
---S---------------------------------I-H------------P---0,8%(1/139)
---S-------A---------------------------------------------A0,8%(1/139)
---S----------------------------S---------S-------------0,8%(1/139)
---S----------------------------S---------W-------------0,8%(1/139)
---S----------------------------------M-----------------0,8%(1/139)
---S---------------M------------------H--M--------------0,8%(1/139)
---S-V--------------------------------------------------0,8%(1/139)
---S-V--------------------------------H-----------------0,8%(1/139)
---S-V--------------------------------Y-----------------0,8%(1/139)
---S-V-----------------------V--------S-----------------0,8%(1/139)
---S------------L---------------------H-----------------0,8%(1/139)
---S---------------------------------A--Y---------------0,8%(1/139)
```

4:

NFITGIQYLAGLSTLPGNPAIASLMAFTASITSPLTTQNTLLFNILGGWVAAQLAPP

```
---S------------------S---AV--------Q-----------S-IRDS 100% (1/1)
```

Figure 5

Shimotono:

KGGRKPARLIVFPDLGVRVCEKMALYDVVSTLPQAVMGPSYGFQ

1a:

```
-------------------------K--L----S-----   57% (8/14)
-------------------------K--P----S-----   21% (3/14)
------------------------TK--L----S-----   21% (3/14)
```

1b:

```
-----------------------------------S-----   68% (97/142)
-----------------------------------------   10% (15/142)
-------------------------------A-----      3% (5/142)
----------------------------V---S-----     2% (3/142)
---Q-------------------------------S-----  1,5% (2/142)
-----A-----------------------------S-----  1,5% (2/142)
------------------------I-------S-----     1,5% (2/142)
-----------E-----------------------S-----  1,5% (2/142)
--------F-----------------------K---S----- 0,8% (1/142)
--------F--------------------------S-----  0,8% (1/142)
-----------------------------R----S---C-   0,8% (1/142)
-----------------------------P---S-----    0,8% (1/142)
-------------------------------H----S----- 0,8% (1/142)
------------------------------SA-----      0,8% (1/142)
-------------------------------S--R--      0,8% (1/142)
-----A-----------------------------------  0,8% (1/142)
-----A----------------N-----------S-----   0,8% (1/142)
------------------------N-------S-----     0,8% (1/142)
-----------E-----------------------------  0,8% (1/142)
-------------------------------H----S----- 0,8% (1/142)
--------------------------HT---S-----      0,8% (1/142)
-----------Y-----------------------S-----  0,8% (1/142)
```

4:

```
-----------Y----S-----R--H--IKKTAL----AA----  100% (1/1)
```

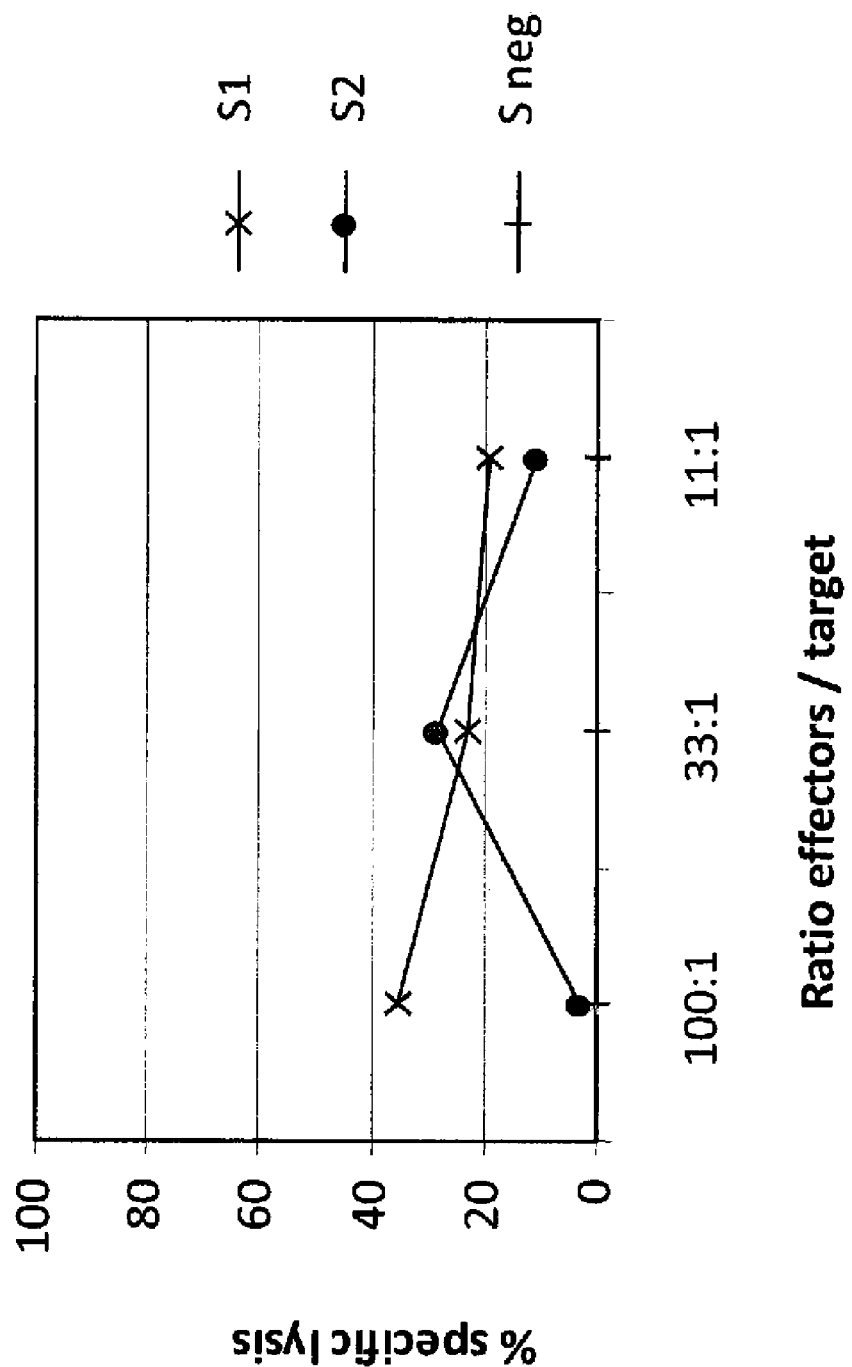

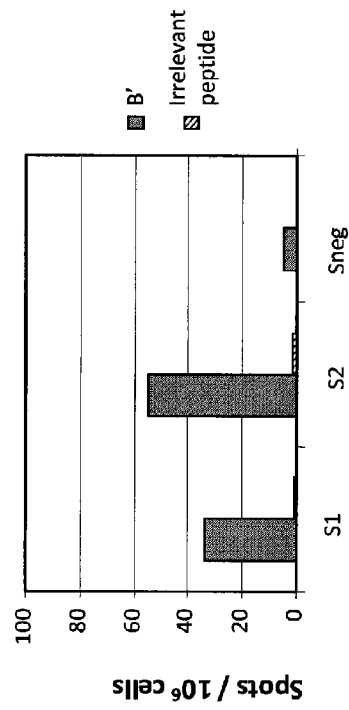
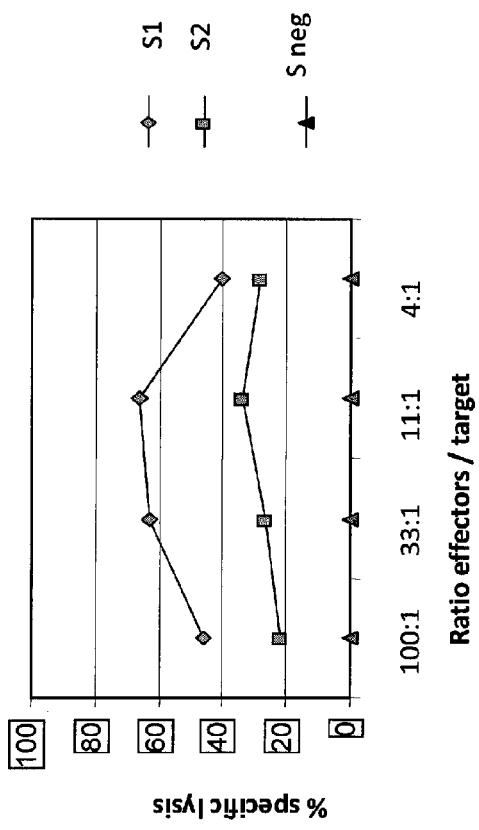
FIGURE 7A
FIGURE 7B

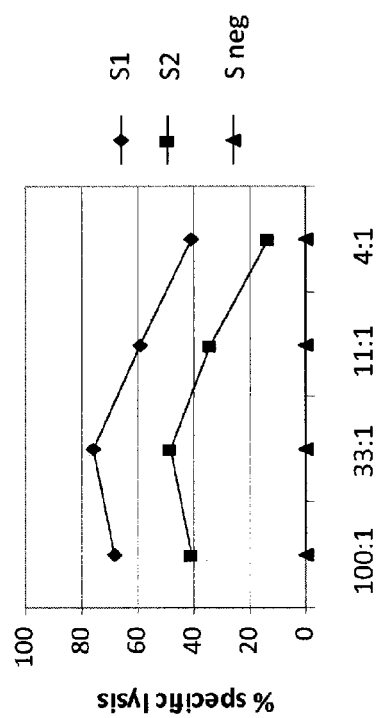
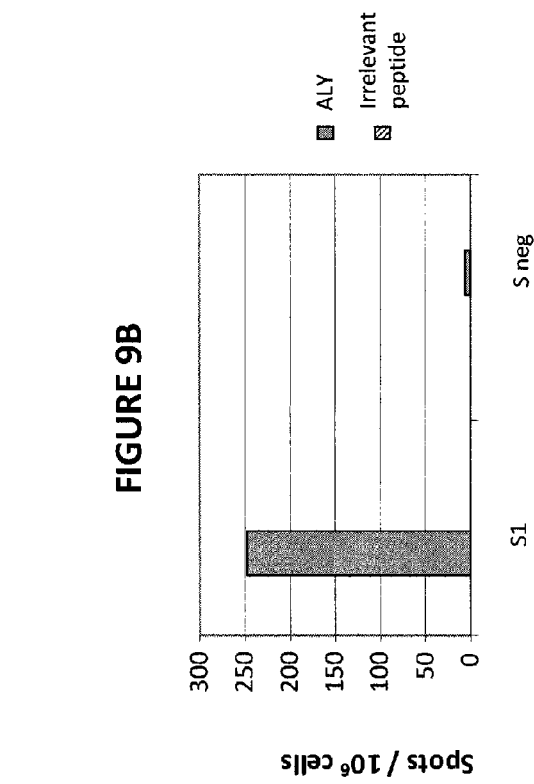
FIGURE 9A
FIGURE 9B

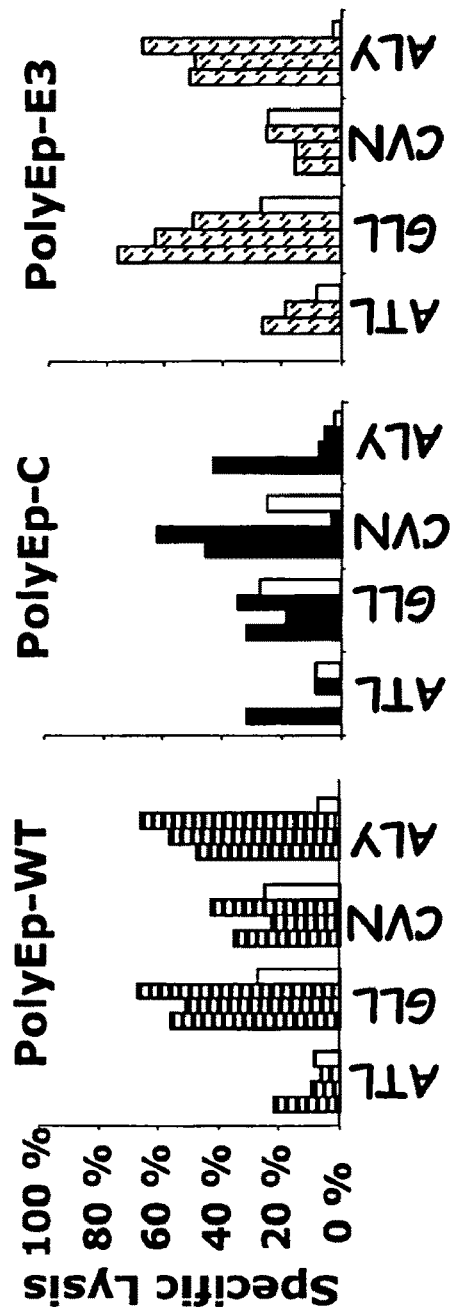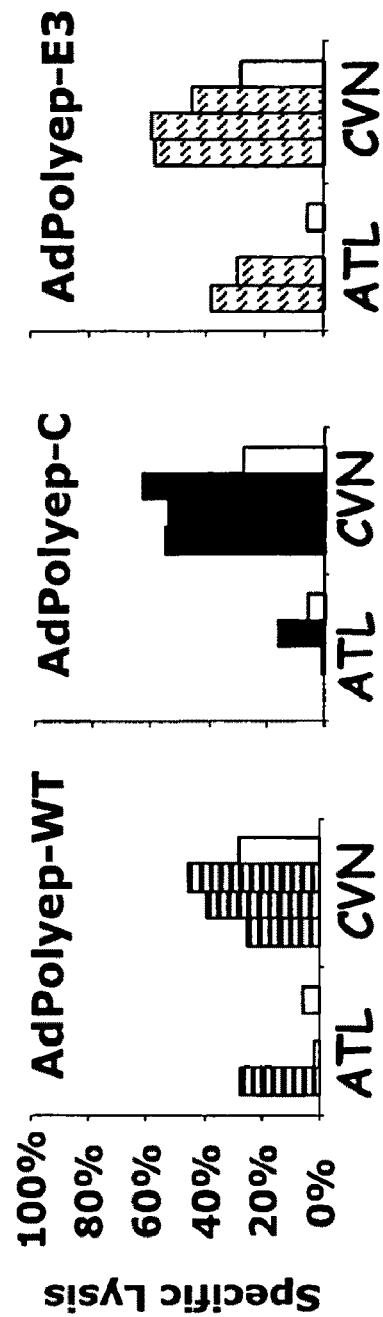
Figure 16A
Figure 16B

SEQUENCE LISTING

<160> NUMBER OF SEQ ID NOS: 248

<210> SEQ ID NO 1
<211> LENGTH: 31

```
<212> TYPE: PRT
<213> ORGANISM: artificial sequence
<220> FEATURE:
<223> OTHER INFORMATION: anti-HCV immunogenic peptide
<220> FEATURE:
<221> NAME/KEY: MISC_FEATURE
<222> LOCATION: (1)..(1)
<223> OTHER INFORMATION: Xaa = Y or H
<220> FEATURE:
<221> NAME/KEY: MISC_FEATURE
<222> LOCATION: (3)..(3)
<223> OTHER INFORMATION: Xaa = A, G, or T
<220> FEATURE:
<221> NAME/KEY: MISC_FEATURE
<222> LOCATION: (9)..(9)
<223> OTHER INFORMATION: Xaa = R or L
<220> FEATURE:
<221> NAME/KEY: MISC_FEATURE
<222> LOCATION: (16)..(16)
<223> OTHER INFORMATION: Xaa = A or T
<220> FEATURE:
<221> NAME/KEY: MISC_FEATURE
<222> LOCATION: (20)..(20)
<223> OTHER INFORMATION: Xaa = G or S
<220> FEATURE:
<221> NAME/KEY: MISC_FEATURE
<222> LOCATION: (23)..(23)
<223> OTHER INFORMATION: Xaa = A, T, or V
<220> FEATURE:
<221> NAME/KEY: MISC_FEATURE
<222> LOCATION: (29)..(29)
<223> OTHER INFORMATION: Xaa = H or Y
<220> FEATURE:
<221> NAME/KEY: MISC_FEATURE
<222> LOCATION: (31)..(31)
<223> OTHER INFORMATION: Xaa = I, T, M or V

<400> SEQUENCE: 1

Xaa Ala Xaa Gln Gly Tyr Lys Val Xaa Val Leu Asn Pro Ser Val Xaa
1               5                   10                  15

Ala Thr Leu Xaa Phe Gly Xaa Tyr Met Ser Lys Ala Xaa Gly Xaa
            20                  25                  30

<210> SEQ ID NO 2
<211> LENGTH: 46
<212> TYPE: PRT
<213> ORGANISM: artificial sequence
<220> FEATURE:
<223> OTHER INFORMATION: anti-HCV immunogenic peptide
<220> FEATURE:
<221> NAME/KEY: MISC_FEATURE
<222> LOCATION: (2)..(2)
<223> OTHER INFORMATION: Xaa = T or N
<220> FEATURE:
<221> NAME/KEY: MISC_FEATURE
<222> LOCATION: (3)..(3)
<223> OTHER INFORMATION: Xaa = K or R
<220> FEATURE:
<221> NAME/KEY: MISC_FEATURE
<222> LOCATION: (6)..(6)
<223> OTHER INFORMATION: Xaa = A or V
<220> FEATURE:
<221> NAME/KEY: MISC_FEATURE
<222> LOCATION: (7)..(7)
<223> OTHER INFORMATION: Xaa = A or E
<220> FEATURE:
<221> NAME/KEY: MISC_FEATURE
<222> LOCATION: (8)..(8)
<223> OTHER INFORMATION: Xaa = Y or H
<220> FEATURE:
<221> NAME/KEY: MISC_FEATURE
<222> LOCATION: (10)..(10)
<223> OTHER INFORMATION: Xaa = A, G, or T
<220> FEATURE:
<221> NAME/KEY: MISC_FEATURE
<222> LOCATION: (16)..(16)
<223> OTHER INFORMATION: Xaa = R or L
```

```
<220> FEATURE:
<221> NAME/KEY: MISC_FEATURE
<222> LOCATION: (23)..(23)
<223> OTHER INFORMATION: Xaa = A or T
<220> FEATURE:
<221> NAME/KEY: MISC_FEATURE
<222> LOCATION: (27)..(27)
<223> OTHER INFORMATION: Xaa = G or S
<220> FEATURE:
<221> NAME/KEY: MISC_FEATURE
<222> LOCATION: (30)..(30)
<223> OTHER INFORMATION: Xaa = A, T, or V
<220> FEATURE:
<221> NAME/KEY: MISC_FEATURE
<222> LOCATION: (36)..(36)
<223> OTHER INFORMATION: Xaa = H or Y
<220> FEATURE:
<221> NAME/KEY: MISC_FEATURE
<222> LOCATION: (38)..(38)
<223> OTHER INFORMATION: Xaa = I, T, M or V
<220> FEATURE:
<221> NAME/KEY: MISC_FEATURE
<222> LOCATION: (39)..(39)
<223> OTHER INFORMATION: Xaa = E or D
<220> FEATURE:
<221> NAME/KEY: MISC_FEATURE
<222> LOCATION: (41)..(41)
<223> OTHER INFORMATION: Xaa = N or S
<220> FEATURE:
<221> NAME/KEY: MISC_FEATURE
<222> LOCATION: (42)..(42)
<223> OTHER INFORMATION: Xaa = I, L or V
<220> FEATURE:
<221> NAME/KEY: MISC_FEATURE
<222> LOCATION: (43)..(43)
<223> OTHER INFORMATION: Xaa = R or S
<220> FEATURE:
<221> NAME/KEY: MISC_FEATURE
<222> LOCATION: (44)..(44)
<223> OTHER INFORMATION: Xaa = T or S

<400> SEQUENCE: 2

Ser Xaa Xaa Val Pro Xaa Xaa Xaa Ala Xaa Gln Gly Tyr Lys Val Xaa
1               5                   10                  15

Val Leu Asn Pro Ser Val Xaa Ala Thr Leu Xaa Phe Gly Xaa Tyr Met
            20                  25                  30

Ser Lys Ala Xaa Gly Xaa Xaa Pro Xaa Xaa Xaa Xaa Gly Val
        35                  40                  45

<210> SEQ ID NO 3
<211> LENGTH: 31
<212> TYPE: PRT
<213> ORGANISM: artificial sequence
<220> FEATURE:
<223> OTHER INFORMATION: anti-HCV immunogenic peptide

<400> SEQUENCE: 3

Tyr Ala Ala Gln Gly Tyr Lys Val Arg Val Leu Asn Pro Ser Val Ala
1               5                   10                  15

Ala Thr Leu Gly Phe Gly Ala Tyr Met Ser Lys Ala His Gly Ile
            20                  25                  30

<210> SEQ ID NO 4
<211> LENGTH: 31
<212> TYPE: PRT
<213> ORGANISM: artificial sequence
<220> FEATURE:
<223> OTHER INFORMATION: anti-HCV immunogenic peptide

<400> SEQUENCE: 4

Tyr Ala Ala Gln Gly Tyr Lys Val Leu Val Leu Asn Pro Ser Val Ala
1               5                   10                  15
```

```
Ala Thr Leu Gly Phe Gly Ala Tyr Met Ser Lys Ala His Gly Ile
            20                  25                  30

<210> SEQ ID NO 5
<211> LENGTH: 31
<212> TYPE: PRT
<213> ORGANISM: artificial sequence
<220> FEATURE:
<223> OTHER INFORMATION: anti-HCV immunogenic peptide

<400> SEQUENCE: 5

Tyr Ala Ala Gln Gly Tyr Lys Val Leu Val Leu Asn Pro Ser Val Ala
1               5                   10                  15

Ala Thr Leu Gly Phe Gly Ala Tyr Met Ser Lys Ala His Gly Val
            20                  25                  30

<210> SEQ ID NO 6
<211> LENGTH: 31
<212> TYPE: PRT
<213> ORGANISM: artificial sequence
<220> FEATURE:
<223> OTHER INFORMATION: anti-HCV immunogenic peptide

<400> SEQUENCE: 6

Tyr Ala Ala Gln Gly Tyr Lys Val Leu Val Leu Asn Pro Ser Val Ala
1               5                   10                  15

Ala Thr Leu Gly Phe Gly Ala Tyr Met Ser Lys Ala His Gly Thr
            20                  25                  30

<210> SEQ ID NO 7
<211> LENGTH: 31
<212> TYPE: PRT
<213> ORGANISM: artificial sequence
<220> FEATURE:
<223> OTHER INFORMATION: anti-HCV immunogenic peptide

<400> SEQUENCE: 7

Tyr Ala Ala Gln Gly Tyr Lys Val Leu Val Leu Asn Pro Ser Val Ala
1               5                   10                  15

Ala Thr Leu Gly Phe Gly Ala Tyr Met Ser Lys Ala Tyr Gly Thr
            20                  25                  30

<210> SEQ ID NO 8
<211> LENGTH: 31
<212> TYPE: PRT
<213> ORGANISM: artificial sequence
<220> FEATURE:
<223> OTHER INFORMATION: anti-HCV immunogenic peptide

<400> SEQUENCE: 8

Tyr Ala Ala Gln Gly Tyr Lys Val Leu Val Leu Asn Pro Ser Val Ala
1               5                   10                  15

Ala Thr Leu Ser Phe Gly Ala Tyr Met Ser Lys Ala His Gly Thr
            20                  25                  30

<210> SEQ ID NO 9
<211> LENGTH: 31
<212> TYPE: PRT
<213> ORGANISM: artificial sequence
<220> FEATURE:
<223> OTHER INFORMATION: anti-HCV immunogenic peptide

<400> SEQUENCE: 9

Tyr Ala Ala Gln Gly Tyr Lys Val Leu Val Leu Asn Pro Ser Val Ala
1               5                   10                  15
```

```
Ala Thr Leu Gly Phe Gly Ala Tyr Met Ser Lys Ala Tyr Gly Ile
            20                  25                  30

<210> SEQ ID NO 10
<211> LENGTH: 31
<212> TYPE: PRT
<213> ORGANISM: artificial sequence
<220> FEATURE:
<223> OTHER INFORMATION: anti-HCV immunogenic peptide

<400> SEQUENCE: 10

Tyr Ala Ala Gln Gly Tyr Lys Val Leu Val Leu Asn Pro Ser Val Thr
1               5                   10                  15

Ala Thr Leu Gly Phe Gly Ala Tyr Met Ser Lys Ala His Gly Val
            20                  25                  30

<210> SEQ ID NO 11
<211> LENGTH: 31
<212> TYPE: PRT
<213> ORGANISM: artificial sequence
<220> FEATURE:
<223> OTHER INFORMATION: anti-HCV immunogenic peptide

<400> SEQUENCE: 11

Tyr Ala Gly Gln Gly Tyr Lys Val Leu Val Leu Asn Pro Ser Val Ala
1               5                   10                  15

Ala Thr Leu Gly Phe Gly Ala Tyr Met Ser Lys Ala His Gly Ile
            20                  25                  30

<210> SEQ ID NO 12
<211> LENGTH: 31
<212> TYPE: PRT
<213> ORGANISM: artificial sequence
<220> FEATURE:
<223> OTHER INFORMATION: anti-HCV immunogenic peptide

<400> SEQUENCE: 12

Tyr Ala Ala Gln Gly Tyr Lys Val Leu Val Leu Asn Pro Ser Val Ala
1               5                   10                  15

Ala Thr Leu Ser Phe Gly Ala Tyr Met Ser Lys Ala His Gly Ile
            20                  25                  30

<210> SEQ ID NO 13
<211> LENGTH: 31
<212> TYPE: PRT
<213> ORGANISM: artificial sequence
<220> FEATURE:
<223> OTHER INFORMATION: anti-HCV immunogenic peptide

<400> SEQUENCE: 13

Tyr Ala Thr Gln Gly Tyr Lys Val Leu Val Leu Asn Pro Ser Val Ala
1               5                   10                  15

Ala Thr Leu Gly Phe Gly Ala Tyr Met Ser Lys Ala His Gly Thr
            20                  25                  30

<210> SEQ ID NO 14
<211> LENGTH: 31
<212> TYPE: PRT
<213> ORGANISM: artificial sequence
<220> FEATURE:
<223> OTHER INFORMATION: anti-HCV immunogenic peptide

<400> SEQUENCE: 14

Tyr Ala Ala Gln Gly Tyr Lys Val Leu Val Leu Asn Pro Ser Val Ala
1               5                   10                  15
```

```
Ala Thr Leu Ser Phe Gly Ala Tyr Met Ser Lys Ala His Gly Val
            20                  25                  30

<210> SEQ ID NO 15
<211> LENGTH: 31
<212> TYPE: PRT
<213> ORGANISM: artificial sequence
<220> FEATURE:
<223> OTHER INFORMATION: anti-HCV immunogenic peptide

<400> SEQUENCE: 15

Tyr Ala Thr Gln Gly Tyr Lys Val Leu Val Leu Asn Pro Ser Val Ala
1               5                   10                  15

Ala Thr Leu Ser Phe Gly Ala Tyr Met Ser Lys Ala Tyr Gly Met
            20                  25                  30

<210> SEQ ID NO 16
<211> LENGTH: 31
<212> TYPE: PRT
<213> ORGANISM: artificial sequence
<220> FEATURE:
<223> OTHER INFORMATION: anti-HCV immunogenic peptide

<400> SEQUENCE: 16

Tyr Ala Ala Gln Gly Tyr Lys Val Leu Val Leu Asn Pro Ser Val Ala
1               5                   10                  15

Ala Thr Leu Ser Phe Gly Ala Tyr Met Ser Lys Ala Tyr Gly Val
            20                  25                  30

<210> SEQ ID NO 17
<211> LENGTH: 31
<212> TYPE: PRT
<213> ORGANISM: artificial sequence
<220> FEATURE:
<223> OTHER INFORMATION: anti-HCV immunogenic peptide

<400> SEQUENCE: 17

Tyr Ala Ala Gln Gly Tyr Lys Val Leu Val Leu Asn Pro Ser Val Ala
1               5                   10                  15

Ala Thr Leu Gly Phe Gly Thr Tyr Met Ser Lys Ala Tyr Gly Thr
            20                  25                  30

<210> SEQ ID NO 18
<211> LENGTH: 31
<212> TYPE: PRT
<213> ORGANISM: artificial sequence
<220> FEATURE:
<223> OTHER INFORMATION: anti-HCV immunogenic peptide

<400> SEQUENCE: 18

His Ala Ala Gln Gly Tyr Lys Val Leu Val Leu Asn Pro Ser Val Ala
1               5                   10                  15

Ala Thr Leu Gly Phe Gly Val Tyr Met Ser Lys Ala Tyr Gly Ile
            20                  25                  30

<210> SEQ ID NO 19
<211> LENGTH: 46
<212> TYPE: PRT
<213> ORGANISM: artificial sequence
<220> FEATURE:
<223> OTHER INFORMATION: anti-HCV immunogenic peptide

<400> SEQUENCE: 19

Ser Thr Lys Val Pro Ala Ala Tyr Ala Ala Gln Gly Tyr Lys Val Arg
1               5                   10                  15

Val Leu Asn Pro Ser Val Ala Ala Thr Leu Gly Phe Gly Ala Tyr Met
            20                  25                  30

Ser Lys Ala His Gly Ile Glu Pro Asn Ile Arg Thr Gly Val
            35                  40                  45

<210> SEQ ID NO 20
<211> LENGTH: 46
<212> TYPE: PRT
<213> ORGANISM: artificial sequence
<220> FEATURE:
<223> OTHER INFORMATION: anti-HCV immunogenic peptide

<400> SEQUENCE: 20

Ser Thr Lys Val Pro Ala Ala Tyr Ala Ala Gln Gly Tyr Lys Val Leu
1               5                   10                  15

Val Leu Asn Pro Ser Val Ala Ala Thr Leu Gly Phe Gly Ala Tyr Met
            20                  25                  30

Ser Lys Ala His Gly Ile Asp Pro Asn Ile Arg Thr Gly Val
            35                  40                  45

<210> SEQ ID NO 21
<211> LENGTH: 46
<212> TYPE: PRT
<213> ORGANISM: artificial sequence
<220> FEATURE:
<223> OTHER INFORMATION: anti-HCV immunogenic peptide

<400> SEQUENCE: 21

Ser Thr Lys Val Pro Ala Ala Tyr Ala Ala Gln Gly Tyr Lys Val Leu
1               5                   10                  15

Val Leu Asn Pro Ser Val Ala Ala Thr Leu Gly Phe Gly Ala Tyr Met
            20                  25                  30

Ser Lys Ala Tyr Gly Val Asp Pro Asn Val Arg Thr Gly Val
            35                  40                  45

<210> SEQ ID NO 22
<211> LENGTH: 46
<212> TYPE: PRT
<213> ORGANISM: artificial sequence
<220> FEATURE:
<223> OTHER INFORMATION: anti-HCV immunogenic peptide

<400> SEQUENCE: 22

Ser Thr Lys Val Pro Ala Ala Tyr Ala Ala Gln Gly Tyr Lys Val Leu
1               5                   10                  15

Val Leu Asn Pro Ser Val Ala Ala Thr Leu Gly Phe Gly Ala Tyr Met
            20                  25                  30

Ser Lys Ala His Gly Thr Asp Pro Asn Ile Arg Thr Gly Val
            35                  40                  45

<210> SEQ ID NO 23
<211> LENGTH: 46
<212> TYPE: PRT
<213> ORGANISM: artificial sequence
<220> FEATURE:
<223> OTHER INFORMATION: anti-HCV immunogenic peptide

<400> SEQUENCE: 23

Ser Thr Lys Val Pro Ala Ala Tyr Ala Ala Gln Gly Tyr Lys Val Leu
1               5                   10                  15

Val Leu Asn Pro Ser Val Ala Ala Thr Leu Gly Phe Gly Ala Tyr Met
            20                  25                  30

```
Ser Lys Ala Tyr Gly Thr Asp Pro Asn Ile Arg Thr Gly Val
        35                  40                  45
```

<210> SEQ ID NO 24
<211> LENGTH: 46
<212> TYPE: PRT
<213> ORGANISM: Artificial Sequence
<220> FEATURE:
<223> OTHER INFORMATION: anti-HCV immunogenic peptide

<400> SEQUENCE: 24

```
Ser Thr Lys Val Pro Ala Ala Tyr Ala Ala Gln Gly Tyr Lys Val Leu
1               5                   10                  15

Val Leu Asn Pro Ser Val Ala Ala Thr Leu Gly Phe Gly Ala Tyr Met
                20                  25                  30

Ser Lys Ala His Gly Ile Glu Pro Asn Ile Arg Thr Gly Val
        35                  40                  45
```

<210> SEQ ID NO 25
<211> LENGTH: 46
<212> TYPE: PRT
<213> ORGANISM: artificial sequence
<220> FEATURE:
<223> OTHER INFORMATION: anti-HCV immunogenic peptide

<400> SEQUENCE: 25

```
Ser Thr Lys Val Pro Ala Ala Tyr Ala Ala Gln Gly Tyr Lys Val Leu
1               5                   10                  15

Val Leu Asn Pro Ser Val Ala Ala Thr Leu Ser Phe Gly Ala Tyr Met
                20                  25                  30

Ser Lys Ala His Gly Thr Asp Pro Asn Ile Arg Thr Gly Val
        35                  40                  45
```

<210> SEQ ID NO 26
<211> LENGTH: 46
<212> TYPE: PRT
<213> ORGANISM: artificial sequence
<220> FEATURE:
<223> OTHER INFORMATION: anti-HCV immunogenic peptide

<400> SEQUENCE: 26

```
Ser Thr Lys Val Pro Ala Ala Tyr Ala Ala Gln Gly Tyr Lys Val Leu
1               5                   10                  15

Val Leu Asn Pro Ser Val Ala Ala Thr Leu Gly Phe Gly Ala Tyr Met
                20                  25                  30

Ser Lys Ala Tyr Gly Ile Asp Pro Asn Val Arg Thr Gly Val
        35                  40                  45
```

<210> SEQ ID NO 27
<211> LENGTH: 46
<212> TYPE: PRT
<213> ORGANISM: artificial sequence
<220> FEATURE:
<223> OTHER INFORMATION: anti-HCV immunogenic peptide

<400> SEQUENCE: 27

```
Ser Thr Lys Val Pro Ala Ala Tyr Ala Ala Gln Gly Tyr Lys Val Leu
1               5                   10                  15

Val Leu Asn Pro Ser Val Ala Ala Thr Leu Gly Phe Gly Ala Tyr Met
                20                  25                  30

Ser Lys Ala His Gly Thr Glu Pro Asn Ile Arg Thr Gly Val
        35                  40                  45
```

```
<210> SEQ ID NO 28
<211> LENGTH: 46
<212> TYPE: PRT
<213> ORGANISM: artificial sequence
<220> FEATURE:
<223> OTHER INFORMATION: anti-HCV immunogenic peptide

<400> SEQUENCE: 28

Ser Asn Lys Val Pro Val Glu Tyr Ala Ala Gln Gly Tyr Lys Val Leu
1               5                   10                  15

Val Leu Asn Pro Ser Val Ala Ala Thr Leu Gly Phe Gly Ala Tyr Met
            20                  25                  30

Ser Lys Ala His Gly Val Asp Pro Asn Ile Arg Thr Gly Val
        35                  40                  45

<210> SEQ ID NO 29
<211> LENGTH: 46
<212> TYPE: PRT
<213> ORGANISM: artificial sequence
<220> FEATURE:
<223> OTHER INFORMATION: anti-HCV immunogenic peptide

<400> SEQUENCE: 29

Ser Thr Lys Val Pro Ala Ala Tyr Ala Ala Gln Gly Tyr Lys Val Leu
1               5                   10                  15

Val Leu Asn Pro Ser Val Thr Ala Thr Leu Gly Phe Gly Ala Tyr Met
            20                  25                  30

Ser Lys Ala His Gly Val Asp Pro Asn Ile Arg Thr Gly Val
        35                  40                  45

<210> SEQ ID NO 30
<211> LENGTH: 46
<212> TYPE: PRT
<213> ORGANISM: artificial sequence
<220> FEATURE:
<223> OTHER INFORMATION: anti-HCV immunogenic peptide

<400> SEQUENCE: 30

Ser Thr Lys Val Pro Ala Ala Tyr Ala Gly Gln Gly Tyr Lys Val Leu
1               5                   10                  15

Val Leu Asn Pro Ser Val Ala Ala Thr Leu Gly Phe Gly Ala Tyr Met
            20                  25                  30

Ser Lys Ala His Gly Ile Asp Pro Asn Ile Arg Thr Gly Val
        35                  40                  45

<210> SEQ ID NO 31
<211> LENGTH: 46
<212> TYPE: PRT
<213> ORGANISM: artificial sequence
<220> FEATURE:
<223> OTHER INFORMATION: anti-HCV immunogenic peptide

<400> SEQUENCE: 31

Ser Thr Lys Val Pro Ala Ala Tyr Ala Ala Gln Gly Tyr Lys Val Leu
1               5                   10                  15

Val Leu Asn Pro Ser Val Ala Ala Thr Leu Ser Phe Gly Ala Tyr Met
            20                  25                  30

Ser Lys Ala His Gly Ile Asp Pro Asn Ile Arg Thr Gly Val
        35                  40                  45

<210> SEQ ID NO 32
<211> LENGTH: 46
<212> TYPE: PRT
<213> ORGANISM: artificial sequence
```

```
<220> FEATURE:
<223> OTHER INFORMATION: anti-HCV immunogenic peptide

<400> SEQUENCE: 32

Ser Thr Arg Val Pro Ala Ala Tyr Ala Ala Gln Gly Tyr Lys Val Leu
1               5                   10                  15

Val Leu Asn Pro Ser Val Ala Ala Thr Leu Gly Phe Gly Ala Tyr Met
            20                  25                  30

Ser Lys Ala His Gly Ile Asp Pro Asn Leu Arg Thr Gly Val
        35                  40                  45

<210> SEQ ID NO 33
<211> LENGTH: 46
<212> TYPE: PRT
<213> ORGANISM: artificial sequence
<220> FEATURE:
<223> OTHER INFORMATION: anti-HCV immunogenic peptide

<400> SEQUENCE: 33

Ser Thr Lys Val Pro Ala Ala Tyr Ala Thr Gln Gly Tyr Lys Val Leu
1               5                   10                  15

Val Leu Asn Pro Ser Val Ala Ala Thr Leu Gly Phe Gly Ala Tyr Met
            20                  25                  30

Ser Lys Ala His Gly Thr Asp Pro Asn Ile Arg Thr Gly Val
        35                  40                  45

<210> SEQ ID NO 34
<211> LENGTH: 46
<212> TYPE: PRT
<213> ORGANISM: artificial sequence
<220> FEATURE:
<223> OTHER INFORMATION: anti-HCV immunogenic peptide

<400> SEQUENCE: 34

Ser Thr Lys Val Pro Ala Ala Tyr Ala Ala Gln Gly Tyr Lys Val Leu
1               5                   10                  15

Val Leu Asn Pro Ser Val Ala Ala Thr Leu Gly Phe Gly Ala Tyr Met
            20                  25                  30

Ser Lys Ala His Gly Ile Asp Pro Asn Val Arg Thr Gly Val
        35                  40                  45

<210> SEQ ID NO 35
<211> LENGTH: 46
<212> TYPE: PRT
<213> ORGANISM: artificial sequence
<220> FEATURE:
<223> OTHER INFORMATION: anti-HCV immunogenic peptide

<400> SEQUENCE: 35

Ser Thr Lys Val Pro Ala Ala Tyr Ala Ala Gln Gly Tyr Lys Val Leu
1               5                   10                  15

Val Leu Asn Pro Ser Val Ala Ala Thr Leu Ser Phe Gly Ala Tyr Met
            20                  25                  30

Ser Lys Ala His Gly Val Asp Pro Ser Ile Arg Thr Gly Val
        35                  40                  45

<210> SEQ ID NO 36
<211> LENGTH: 46
<212> TYPE: PRT
<213> ORGANISM: artificial sequence
<220> FEATURE:
<223> OTHER INFORMATION: anti-HCV immunogenic peptide

<400> SEQUENCE: 36
```

```
Ser Thr Lys Val Pro Ala Ala Tyr Ala Ala Gln Gly Tyr Lys Val Leu
1               5                   10                  15

Val Leu Asn Pro Ser Val Ala Ala Thr Leu Gly Phe Gly Ala Tyr Met
            20                  25                  30

Ser Lys Ala His Gly Val Asp Pro Asn Ile Ser Thr Gly Val
        35                  40                  45

<210> SEQ ID NO 37
<211> LENGTH: 46
<212> TYPE: PRT
<213> ORGANISM: artificial sequence
<220> FEATURE:
<223> OTHER INFORMATION: anti-HCV immunogenic peptide

<400> SEQUENCE: 37

Ser Thr Lys Val Pro Ala Ala Tyr Ala Ala Gln Gly Tyr Lys Val Leu
1               5                   10                  15

Val Leu Asn Pro Ser Val Ala Ala Thr Leu Gly Phe Gly Ala Tyr Met
            20                  25                  30

Ser Lys Ala Tyr Gly Thr Asp Pro Asn Val Arg Thr Gly Val
        35                  40                  45

<210> SEQ ID NO 38
<211> LENGTH: 46
<212> TYPE: PRT
<213> ORGANISM: artificial sequence
<220> FEATURE:
<223> OTHER INFORMATION: anti-HCV immunogenic peptide

<400> SEQUENCE: 38

Ser Thr Lys Val Pro Ala Ala Tyr Ala Thr Gln Gly Tyr Lys Val Leu
1               5                   10                  15

Val Leu Asn Pro Ser Val Ala Ala Thr Leu Ser Phe Gly Ala Tyr Met
            20                  25                  30

Ser Lys Ala Tyr Gly Met Asp Pro Asn Leu Arg Thr Gly Val
        35                  40                  45

<210> SEQ ID NO 39
<211> LENGTH: 46
<212> TYPE: PRT
<213> ORGANISM: Artificial Sequence
<220> FEATURE:
<223> OTHER INFORMATION: anti-HCV immunogenic peptide

<400> SEQUENCE: 39

Ser Thr Lys Val Pro Ala Ala Tyr Ala Ala Gln Gly Tyr Lys Val Leu
1               5                   10                  15

Val Leu Asn Pro Ser Val Ala Ala Thr Leu Ser Phe Gly Ala Tyr Met
            20                  25                  30

Ser Lys Ala His Gly Val Asp Pro Asn Ile Arg Thr Gly Val
        35                  40                  45

<210> SEQ ID NO 40
<211> LENGTH: 46
<212> TYPE: PRT
<213> ORGANISM: artificial sequence
<220> FEATURE:
<223> OTHER INFORMATION: anti-HCV immunogenic peptide

<400> SEQUENCE: 40

Ser Thr Lys Val Pro Ala Ala Tyr Ala Ala Gln Gly Tyr Lys Val Leu
1               5                   10                  15
```

Val Leu Asn Pro Ser Val Ala Ala Thr Leu Ser Phe Gly Ala Tyr Met
            20                  25                  30

Ser Lys Ala Tyr Gly Val Asp Pro Asn Ile Arg Thr Gly Val
        35                  40                  45

<210> SEQ ID NO 41
<211> LENGTH: 46
<212> TYPE: PRT
<213> ORGANISM: artificial sequence
<220> FEATURE:
<223> OTHER INFORMATION: anti-HCV immunogenic peptide

<400> SEQUENCE: 41

Ser Thr Arg Val Pro Ala Ala Tyr Ala Ala Gln Gly Tyr Lys Val Leu
1               5                   10                  15

Val Leu Asn Pro Ser Val Ala Ala Thr Leu Gly Phe Gly Ala Tyr Met
            20                  25                  30

Ser Lys Ala His Gly Thr Asp Pro Asn Ile Arg Thr Gly Val
        35                  40                  45

<210> SEQ ID NO 42
<211> LENGTH: 46
<212> TYPE: PRT
<213> ORGANISM: artificial sequence
<220> FEATURE:
<223> OTHER INFORMATION: anti-HCV immunogenic peptide

<400> SEQUENCE: 42

Ser Thr Arg Val Pro Ala Ala Tyr Ala Ala Gln Gly Tyr Lys Val Leu
1               5                   10                  15

Val Leu Asn Pro Ser Val Ala Ala Thr Leu Ser Phe Gly Ala Tyr Met
            20                  25                  30

Ser Lys Ala Tyr Gly Val Asp Pro Asn Ile Arg Thr Gly Val
        35                  40                  45

<210> SEQ ID NO 43
<211> LENGTH: 46
<212> TYPE: PRT
<213> ORGANISM: artificial sequence
<220> FEATURE:
<223> OTHER INFORMATION: anti-HCV immunogenic peptide

<400> SEQUENCE: 43

Ser Thr Arg Val Pro Ala Ala Tyr Ala Ala Gln Gly Tyr Lys Val Leu
1               5                   10                  15

Val Leu Asn Pro Ser Val Ala Ala Thr Leu Gly Phe Gly Thr Tyr Met
            20                  25                  30

Ser Lys Ala Tyr Gly Thr Asp Pro Asn Ile Arg Thr Gly Val
        35                  40                  45

<210> SEQ ID NO 44
<211> LENGTH: 46
<212> TYPE: PRT
<213> ORGANISM: artificial sequence
<220> FEATURE:
<223> OTHER INFORMATION: anti-HCV immunogenic peptide

<400> SEQUENCE: 44

Ser Thr Lys Val Pro Ala Ala His Ala Ala Gln Gly Tyr Lys Val Leu
1               5                   10                  15

Val Leu Asn Pro Ser Val Ala Ala Thr Leu Gly Phe Gly Val Tyr Met
            20                  25                  30

Ser Lys Ala Tyr Gly Ile Asp Pro Asn Ile Arg Ser Gly Val

<210> SEQ ID NO 45
<211> LENGTH: 45
<212> TYPE: PRT
<213> ORGANISM: artificial sequence
<220> FEATURE:
<223> OTHER INFORMATION: anti-HCV immunogenic peptide
<220> FEATURE:
<221> NAME/KEY: MISC_FEATURE
<222> LOCATION: (2)..(2)
<223> OTHER INFORMATION: Xaa = L or V
<220> FEATURE:
<221> NAME/KEY: MISC_FEATURE
<222> LOCATION: (3)..(3)
<223> OTHER INFORMATION: Xaa = L or F
<220> FEATURE:
<221> NAME/KEY: MISC_FEATURE
<222> LOCATION: (4)..(4)
<223> OTHER INFORMATION: Xaa = G or S
<220> FEATURE:
<221> NAME/KEY: MISC_FEATURE
<222> LOCATION: (5)..(5)
<223> OTHER INFORMATION: Xaa = C or T
<220> FEATURE:
<221> NAME/KEY: MISC_FEATURE
<222> LOCATION: (6)..(6)
<223> OTHER INFORMATION: Xaa = I or V
<220> FEATURE:
<221> NAME/KEY: MISC_FEATURE
<222> LOCATION: (7)..(7)
<223> OTHER INFORMATION: Xaa = I or V
<220> FEATURE:
<221> NAME/KEY: MISC_FEATURE
<222> LOCATION: (15)..(15)
<223> OTHER INFORMATION: Xaa = K, R or T
<220> FEATURE:
<221> NAME/KEY: MISC_FEATURE
<222> LOCATION: (17)..(17)
<223> OTHER INFORMATION: Xaa = Q or E
<220> FEATURE:
<221> NAME/KEY: MISC_FEATURE
<222> LOCATION: (18)..(18)
<223> OTHER INFORMATION: Xaa = V or N
<220> FEATURE:
<221> NAME/KEY: MISC_FEATURE
<222> LOCATION: (19)..(19)
<223> OTHER INFORMATION: Xaa = D, E or C
<220> FEATURE:
<221> NAME/KEY: MISC_FEATURE
<222> LOCATION: (22)..(22)
<223> OTHER INFORMATION: Xaa = V or A
<220> FEATURE:
<221> NAME/KEY: MISC_FEATURE
<222> LOCATION: (24)..(24)
<223> OTHER INFORMATION: Xaa = V, I, E or M
<220> FEATURE:
<221> NAME/KEY: MISC_FEATURE
<222> LOCATION: (25)..(25)
<223> OTHER INFORMATION: Xaa = L or V
<220> FEATURE:
<221> NAME/KEY: MISC_FEATURE
<222> LOCATION: (29)..(29)
<223> OTHER INFORMATION: Xaa = T, K or A
<220> FEATURE:
<221> NAME/KEY: MISC_FEATURE
<222> LOCATION: (30)..(30)
<223> OTHER INFORMATION: Xaa = Q or H
<220> FEATURE:
<221> NAME/KEY: MISC_FEATURE
<222> LOCATION: (31)..(31)
<223> OTHER INFORMATION: Xaa = S or T
<220> FEATURE:
<221> NAME/KEY: MISC_FEATURE
<222> LOCATION: (34)..(34)
<223> OTHER INFORMATION: Xaa = A or G
<220> FEATURE:
<221> NAME/KEY: MISC_FEATURE
<222> LOCATION: (35)..(35)

```
<223> OTHER INFORMATION: Xaa = T or S
<220> FEATURE:
<221> NAME/KEY: MISC_FEATURE
<222> LOCATION: (36)..(36)
<223> OTHER INFORMATION: Xaa = C or A
<220> FEATURE:
<221> NAME/KEY: MISC_FEATURE
<222> LOCATION: (37)..(37)
<223> OTHER INFORMATION: Xaa = V, I or T
<220> FEATURE:
<221> NAME/KEY: MISC_FEATURE
<222> LOCATION: (40)..(40)
<223> OTHER INFORMATION: Xaa = V or A
<220> FEATURE:
<221> NAME/KEY: MISC_FEATURE
<222> LOCATION: (41)..(41)
<223> OTHER INFORMATION: Xaa = C or M
<220> FEATURE:
<221> NAME/KEY: MISC_FEATURE
<222> LOCATION: (45)..(45)
<223> OTHER INFORMATION: Xaa = Y or F

<400> SEQUENCE: 45

Gly Xaa Xaa Xaa Xaa Xaa Xaa Thr Ser Leu Thr Gly Arg Asp Xaa Asn
1               5                   10                  15

Xaa Xaa Xaa Gly Glu Xaa Gln Xaa Xaa Ser Thr Ala Xaa Xaa Xaa Phe
            20                  25                  30

Leu Xaa Xaa Xaa Xaa Asn Gly Xaa Xaa Trp Thr Val Xaa
        35                  40                  45

<210> SEQ ID NO 46
<211> LENGTH: 63
<212> TYPE: PRT
<213> ORGANISM: artificial sequence
<220> FEATURE:
<223> OTHER INFORMATION: anti-HCV immunogenic peptide
<220> FEATURE:
<221> NAME/KEY: MISC_FEATURE
<222> LOCATION: (2)..(2)
<223> OTHER INFORMATION: Xaa = P, S, or H
<220> FEATURE:
<221> NAME/KEY: MISC_FEATURE
<222> LOCATION: (5)..(5)
<223> OTHER INFORMATION: Xaa = A or T
<220> FEATURE:
<221> NAME/KEY: MISC_FEATURE
<222> LOCATION: (7)..(7)
<223> OTHER INFORMATION: Xaa = S, A, T or C
<220> FEATURE:
<221> NAME/KEY: MISC_FEATURE
<222> LOCATION: (8)..(8)
<223> OTHER INFORMATION: Xaa = Q or R
<220> FEATURE:
<221> NAME/KEY: MISC_FEATURE
<222> LOCATION: (13)..(13)
<223> OTHER INFORMATION: Xaa = L or V
<220> FEATURE:
<221> NAME/KEY: MISC_FEATURE
<222> LOCATION: (14)..(14)
<223> OTHER INFORMATION: Xaa = L or F
<220> FEATURE:
<221> NAME/KEY: MISC_FEATURE
<222> LOCATION: (15)..(15)
<223> OTHER INFORMATION: Xaa = G or S
<220> FEATURE:
<221> NAME/KEY: MISC_FEATURE
<222> LOCATION: (16)..(16)
<223> OTHER INFORMATION: Xaa = C or T
<220> FEATURE:
<221> NAME/KEY: MISC_FEATURE
<222> LOCATION: (17)..(17)
<223> OTHER INFORMATION: Xaa = I or V
<220> FEATURE:
<221> NAME/KEY: MISC_FEATURE
<222> LOCATION: (18)..(18)
<223> OTHER INFORMATION: Xaa = I or V
```

-continued

```
<220> FEATURE:
<221> NAME/KEY: MISC_FEATURE
<222> LOCATION: (26)..(26)
<223> OTHER INFORMATION: Xaa = K, R or T
<220> FEATURE:
<221> NAME/KEY: MISC_FEATURE
<222> LOCATION: (28)..(28)
<223> OTHER INFORMATION: Xaa = Q or E
<220> FEATURE:
<221> NAME/KEY: MISC_FEATURE
<222> LOCATION: (29)..(29)
<223> OTHER INFORMATION: Xaa = V or N
<220> FEATURE:
<221> NAME/KEY: MISC_FEATURE
<222> LOCATION: (30)..(30)
<223> OTHER INFORMATION: Xaa = D, E or C
<220> FEATURE:
<221> NAME/KEY: MISC_FEATURE
<222> LOCATION: (33)..(33)
<223> OTHER INFORMATION: Xaa = V or A
<220> FEATURE:
<221> NAME/KEY: MISC_FEATURE
<222> LOCATION: (35)..(35)
<223> OTHER INFORMATION: Xaa = V, I, E or M
<220> FEATURE:
<221> NAME/KEY: MISC_FEATURE
<222> LOCATION: (36)..(36)
<223> OTHER INFORMATION: Xaa = L or V
<220> FEATURE:
<221> NAME/KEY: MISC_FEATURE
<222> LOCATION: (40)..(40)
<223> OTHER INFORMATION: Xaa = T, K or A
<220> FEATURE:
<221> NAME/KEY: MISC_FEATURE
<222> LOCATION: (41)..(41)
<223> OTHER INFORMATION: Xaa =  Q or H
<220> FEATURE:
<221> NAME/KEY: MISC_FEATURE
<222> LOCATION: (42)..(42)
<223> OTHER INFORMATION: Xaa =  S or T
<220> FEATURE:
<221> NAME/KEY: MISC_FEATURE
<222> LOCATION: (45)..(45)
<223> OTHER INFORMATION: Xaa =  A or G
<220> FEATURE:
<221> NAME/KEY: MISC_FEATURE
<222> LOCATION: (46)..(46)
<223> OTHER INFORMATION: Xaa =  T or S
<220> FEATURE:
<221> NAME/KEY: MISC_FEATURE
<222> LOCATION: (47)..(47)
<223> OTHER INFORMATION: Xaa =  C or A
<220> FEATURE:
<221> NAME/KEY: MISC_FEATURE
<222> LOCATION: (48)..(48)
<223> OTHER INFORMATION: Xaa =  V, I or T
<220> FEATURE:
<221> NAME/KEY: MISC_FEATURE
<222> LOCATION: (51)..(51)
<223> OTHER INFORMATION: Xaa =  V or A
<220> FEATURE:
<221> NAME/KEY: MISC_FEATURE
<222> LOCATION: (52)..(52)
<223> OTHER INFORMATION: Xaa =  C or M
<220> FEATURE:
<221> NAME/KEY: MISC_FEATURE
<222> LOCATION: (56)..(56)
<223> OTHER INFORMATION: Xaa =  Y or F
<220> FEATURE:
<221> NAME/KEY: MISC_FEATURE
<222> LOCATION: (61)..(61)
<223> OTHER INFORMATION: Xaa =  S, T or A
<220> FEATURE:
<221> NAME/KEY: MISC_FEATURE
<222> LOCATION: (62)..(62)
<223> OTHER INFORMATION: Xaa =  K or R
<220> FEATURE:
<221> NAME/KEY: MISC_FEATURE
<222> LOCATION: (63)..(63)
<223> OTHER INFORMATION: Xaa =  T or I
```

-continued

<400> SEQUENCE: 46

Ala Xaa Ile Thr Xaa Tyr Xaa Xaa Gln Thr Arg Gly Xaa Xaa Xaa
1               5                   10                  15

Xaa Xaa Thr Ser Leu Thr Gly Arg Asp Xaa Asn Xaa Xaa Xaa Gly Glu
            20                  25                  30

Xaa Gln Xaa Xaa Ser Thr Ala Xaa Xaa Xaa Phe Leu Xaa Xaa Xaa Xaa
        35                  40                  45

Asn Gly Xaa Xaa Trp Thr Val Xaa His Gly Ala Gly Xaa Xaa Xaa
        50                  55                  60

<210> SEQ ID NO 47
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 47

Gly Leu Leu Gly Cys Ile Ile Thr Ser Leu Thr Gly Arg Asp Lys Asn
1               5                   10                  15

Gln Val Asp Gly Glu Val Gln Val Leu Ser Thr Ala Thr Gln Ser Phe
            20                  25                  30

Leu Ala Thr Cys Val Asn Gly Val Cys Trp Thr Val Tyr
        35                  40                  45

<210> SEQ ID NO 48
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 48

Gly Leu Leu Gly Cys Ile Ile Thr Ser Leu Thr Gly Arg Asp Lys Asn
1               5                   10                  15

Gln Val Glu Gly Glu Val Gln Ile Val Ser Thr Ala Ala Gln Thr Phe
            20                  25                  30

Leu Ala Thr Cys Ile Asn Gly Val Cys Trp Thr Val Tyr
        35                  40                  45

<210> SEQ ID NO 49
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 49

Gly Leu Leu Gly Cys Ile Ile Thr Ser Leu Thr Gly Arg Asp Lys Asn
1               5                   10                  15

Gln Val Glu Gly Glu Val Gln Ile Val Ser Thr Ala Thr Gln Thr Phe
            20                  25                  30

Leu Ala Thr Cys Ile Asn Gly Val Cys Trp Thr Val Tyr
        35                  40                  45

<210> SEQ ID NO 50
<211> LENGTH: 45
<212> TYPE: PRT
<213> ORGANISM: artificial sequence
<220> FEATURE:
<223> OTHER INFORMATION: anti-HCV immunogenic peptide

```
<400> SEQUENCE: 50

Gly Leu Leu Gly Cys Ile Ile Thr Ser Leu Thr Gly Arg Asp Lys Asn
1               5                   10                  15

Gln Val Glu Gly Glu Val Gln Val Val Ser Thr Ala Thr Gln Ser Phe
            20                  25                  30

Leu Ala Thr Cys Val Asn Gly Val Cys Trp Thr Val Tyr
        35                  40                  45

<210> SEQ ID NO 51
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 51

Gly Leu Leu Gly Cys Ile Ile Thr Ser Leu Thr Gly Arg Asp Arg Asn
1               5                   10                  15

Gln Val Glu Gly Glu Val Gln Val Val Ser Thr Ala Thr Gln Ser Phe
            20                  25                  30

Leu Ala Thr Cys Val Asn Gly Val Cys Trp Thr Val Tyr
        35                  40                  45

<210> SEQ ID NO 52
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 52

Gly Leu Leu Gly Cys Ile Ile Thr Ser Leu Thr Gly Arg Asp Lys Asn
1               5                   10                  15

Gln Val Glu Gly Glu Val Gln Val Val Ser Thr Ala Thr Gln Ser Phe
            20                  25                  30

Leu Ala Thr Cys Ile Asn Gly Val Cys Trp Thr Val Tyr
        35                  40                  45

<210> SEQ ID NO 53
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 53

Gly Leu Phe Gly Cys Ile Ile Thr Ser Leu Thr Gly Arg Asp Lys Asn
1               5                   10                  15

Gln Val Glu Gly Glu Val Gln Val Val Ser Thr Ala Thr Gln Ser Phe
            20                  25                  30

Leu Ala Thr Cys Val Asn Gly Val Cys Trp Thr Val Tyr
        35                  40                  45

<210> SEQ ID NO 54
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 54

Gly Val Leu Gly Cys Val Ile Thr Ser Leu Thr Gly Arg Asp Lys Asn
1               5                   10                  15
```

Gln Val Glu Gly Glu Val Gln Val Val Ser Thr Ala Thr Gln Ser Phe
            20                  25                  30

Leu Ala Thr Cys Ile Asn Gly Val Cys Trp Thr Val Tyr
        35                  40                  45

<210> SEQ ID NO 55
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 55

Gly Leu Leu Gly Cys Ile Ile Thr Ser Leu Thr Gly Arg Asp Lys Asn
1               5                   10                  15

Gln Val Glu Gly Glu Val Gln Val Val Ser Thr Ala Thr Gln Ser Phe
            20                  25                  30

Leu Ala Thr Cys Val Asn Gly Ala Cys Trp Thr Val Phe
        35                  40                  45

<210> SEQ ID NO 56
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 56

Gly Leu Leu Gly Cys Ile Ile Thr Ser Leu Thr Gly Arg Asp Lys Asn
1               5                   10                  15

Gln Val Glu Gly Glu Val Gln Val Val Ser Thr Ala Thr Gln Ser Phe
            20                  25                  30

Leu Ala Thr Cys Ile Asn Gly Val Cys Trp Thr Val Phe
        35                  40                  45

<210> SEQ ID NO 57
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 57

Gly Val Leu Gly Cys Ile Ile Thr Ser Leu Thr Gly Arg Asp Lys Asn
1               5                   10                  15

Gln Val Glu Gly Glu Val Gln Val Val Ser Thr Ala Thr Gln Ser Phe
            20                  25                  30

Leu Ala Thr Cys Ile Asn Gly Val Cys Trp Thr Val Tyr
        35                  40                  45

<210> SEQ ID NO 58
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 58

Gly Leu Leu Gly Cys Ile Ile Thr Ser Leu Thr Gly Arg Asp Lys Asn
1               5                   10                  15

Gln Val Glu Gly Glu Val Gln Val Val Ser Thr Ala Thr Gln Ser Phe
            20                  25                  30

Leu Ala Thr Cys Val Asn Gly Val Cys Trp Thr Val Phe
            35                  40                  45

<210> SEQ ID NO 59
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 59

Gly Leu Leu Gly Cys Ile Val Thr Ser Leu Thr Gly Arg Asp Lys Asn
1               5                   10                  15

Gln Val Glu Gly Glu Val Gln Val Val Ser Thr Ala Thr Gln Ser Phe
            20                  25                  30

Leu Ala Thr Cys Val Asn Gly Ala Cys Trp Thr Val Phe
            35                  40                  45

<210> SEQ ID NO 60
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 60

Gly Val Leu Gly Cys Ile Ile Thr Ser Leu Thr Gly Arg Asp Lys Asn
1               5                   10                  15

Gln Val Glu Gly Glu Val Gln Val Val Ser Thr Ala Thr Gln Ser Phe
            20                  25                  30

Leu Ala Thr Cys Val Asn Gly Val Cys Trp Thr Val Phe
            35                  40                  45

<210> SEQ ID NO 61
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 61

Gly Leu Leu Gly Cys Ile Ile Thr Ser Leu Thr Gly Arg Asp Lys Asn
1               5                   10                  15

Gln Val Asp Gly Glu Val Gln Val Leu Ser Thr Ala Thr Gln Ser Phe
            20                  25                  30

Leu Ala Thr Cys Ile Asn Gly Val Cys Trp Thr Val Tyr
            35                  40                  45

<210> SEQ ID NO 62
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 62

Gly Leu Leu Gly Cys Ile Ile Thr Ser Leu Thr Gly Arg Asp Lys Asn
1               5                   10                  15

Gln Val Glu Gly Glu Val Gln Val Val Ser Thr Ala Thr Gln Ser Phe
            20                  25                  30

Leu Ala Thr Cys Val Asn Gly Ala Cys Trp Thr Val Tyr
            35                  40                  45

```
<210> SEQ ID NO 63
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 63

Gly Val Leu Gly Cys Ile Ile Thr Ser Leu Thr Gly Arg Asp Lys Asn
1               5                   10                  15

Gln Val Glu Gly Glu Val Gln Val Val Ser Thr Ala Thr His Ser Phe
            20                  25                  30

Leu Ala Thr Cys Ile Asn Gly Val Cys Trp Thr Val Tyr
        35                  40                  45

<210> SEQ ID NO 64
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 64

Gly Leu Leu Gly Cys Ile Ile Thr Ser Leu Thr Gly Arg Asp Lys Asn
1               5                   10                  15

Gln Val Glu Gly Glu Val Gln Val Val Ser Thr Ala Thr Gln Ser Phe
            20                  25                  30

Leu Ala Thr Cys Ile Asn Gly Ala Cys Trp Thr Val Tyr
        35                  40                  45

<210> SEQ ID NO 65
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 65

Gly Leu Leu Gly Cys Ile Ile Thr Ser Leu Thr Gly Arg Asp Lys Asn
1               5                   10                  15

Gln Val Glu Gly Glu Val Gln Val Val Ser Thr Ala Thr Gln Ser Phe
            20                  25                  30

Leu Ala Ser Cys Val Asn Gly Val Cys Trp Thr Val Tyr
        35                  40                  45

<210> SEQ ID NO 66
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 66

Gly Leu Leu Gly Cys Ile Ile Thr Ser Leu Thr Gly Arg Asp Lys Asn
1               5                   10                  15

Gln Val Glu Gly Glu Val Gln Val Val Ser Thr Ala Thr Gln Ser Phe
            20                  25                  30

Leu Ala Thr Cys Thr Asn Gly Val Cys Trp Thr Val Tyr
        35                  40                  45

<210> SEQ ID NO 67
<211> LENGTH: 45
<212> TYPE: PRT
<213> ORGANISM: artificial sequence
```

<220> FEATURE:
<223> OTHER INFORMATION: anti-HCV immunogenic peptide

<400> SEQUENCE: 67

Gly Val Leu Gly Cys Ile Ile Thr Ser Leu Thr Gly Arg Asp Lys Asn
1               5                   10                  15

Gln Val Glu Gly Glu Val Gln Val Val Ser Thr Ala Thr Gln Ser Phe
            20                  25                  30

Leu Ala Thr Cys Val Asn Gly Val Cys Trp Thr Val Tyr
        35                  40                  45

<210> SEQ ID NO 68
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 68

Gly Leu Leu Gly Cys Ile Ile Thr Ser Leu Thr Gly Arg Asp Lys Asn
1               5                   10                  15

Gln Val Glu Gly Glu Val Gln Val Val Ser Thr Ala Lys Gln Ser Phe
            20                  25                  30

Leu Ala Thr Cys Val Asn Gly Val Cys Trp Thr Val Tyr
        35                  40                  45

<210> SEQ ID NO 69
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 69

Gly Leu Leu Gly Cys Ile Ile Thr Ser Leu Thr Gly Arg Asp Lys Asn
1               5                   10                  15

Gln Val Glu Gly Glu Val Gln Val Val Ser Thr Ala Lys Gln Ser Phe
            20                  25                  30

Leu Ala Thr Cys Val Asn Gly Ala Cys Trp Thr Val Tyr
        35                  40                  45

<210> SEQ ID NO 70
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 70

Gly Leu Leu Gly Cys Ile Ile Thr Ser Leu Thr Gly Arg Asp Lys Asn
1               5                   10                  15

Gln Val Glu Gly Glu Val Gln Val Val Ser Thr Ala Thr Gln Thr Phe
            20                  25                  30

Leu Ala Thr Cys Val Asn Gly Val Cys Trp Thr Val Phe
        35                  40                  45

<210> SEQ ID NO 71
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 71

```
Gly Leu Leu Gly Cys Ile Ile Thr Ser Leu Thr Gly Arg Asp Lys Asn
1               5                   10                  15

Gln Val Glu Gly Glu Val Gln Glu Val Ser Thr Ala Thr Gln Ser Phe
            20                  25                  30

Leu Ala Thr Cys Val Asn Gly Val Cys Trp Thr Val Tyr
            35                  40                  45

<210> SEQ ID NO 72
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 72

Gly Leu Phe Gly Cys Ile Val Thr Ser Leu Thr Gly Arg Asp Lys Asn
1               5                   10                  15

Gln Val Glu Gly Glu Ala Gln Val Val Ser Thr Ala Thr Gln Ser Phe
            20                  25                  30

Leu Ala Thr Cys Val Asn Gly Val Cys Trp Thr Val Tyr
            35                  40                  45

<210> SEQ ID NO 73
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 73

Gly Leu Phe Gly Cys Ile Ile Thr Ser Leu Thr Gly Arg Asp Lys Asn
1               5                   10                  15

Gln Val Glu Gly Glu Val Gln Val Val Ser Thr Ala Thr Gln Ser Phe
            20                  25                  30

Leu Ala Thr Cys Ile Asn Gly Val Cys Trp Thr Val Tyr
            35                  40                  45

<210> SEQ ID NO 74
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 74

Gly Leu Phe Gly Cys Ile Val Thr Ser Leu Thr Gly Arg Asp Lys Asn
1               5                   10                  15

Gln Val Glu Gly Glu Ala Gln Val Val Ser Thr Ala Thr Gln Ser Phe
            20                  25                  30

Leu Ala Thr Cys Val Asn Gly Ala Cys Trp Thr Val Tyr
            35                  40                  45

<210> SEQ ID NO 75
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 75

Gly Leu Leu Gly Cys Ile Val Thr Ser Leu Thr Gly Arg Asp Lys Asn
1               5                   10                  15
```

```
Gln Val Glu Gly Glu Val Gln Val Val Ser Thr Ala Thr Gln Ser Phe
            20                  25                  30

Leu Ala Thr Cys Val Asn Gly Val Cys Trp Thr Val Phe
        35                  40                  45

<210> SEQ ID NO 76
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 76

Gly Leu Phe Gly Cys Ile Ile Thr Ser Leu Thr Gly Arg Asp Arg Asn
1               5                   10                  15

Gln Val Glu Gly Glu Val Gln Val Ser Thr Ala Thr Gln Ser Phe
            20                  25                  30

Leu Ala Thr Cys Ile Asn Gly Val Cys Trp Thr Val Tyr
        35                  40                  45

<210> SEQ ID NO 77
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 77

Gly Leu Phe Gly Cys Ile Ile Thr Ser Leu Thr Gly Arg Asp Lys Asn
1               5                   10                  15

Gln Val Glu Gly Glu Val Gln Val Ser Thr Ala Thr Gln Ser Phe
            20                  25                  30

Leu Ala Thr Cys Ile Asn Gly Val Cys Trp Thr Val Tyr
        35                  40                  45

<210> SEQ ID NO 78
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 78

Gly Leu Leu Gly Cys Ile Ile Thr Ser Leu Thr Gly Arg Asp Arg Asn
1               5                   10                  15

Gln Val Glu Gly Glu Val Gln Val Ser Thr Ala Thr Gln Ser Phe
            20                  25                  30

Leu Ala Thr Cys Ile Asn Gly Val Cys Trp Thr Val Phe
        35                  40                  45

<210> SEQ ID NO 79
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 79

Gly Leu Leu Gly Cys Ile Ile Thr Ser Leu Thr Gly Arg Asp Arg Asn
1               5                   10                  15

Gln Val Glu Gly Glu Val Gln Met Val Ser Thr Ala Thr Gln Ser Phe
            20                  25                  30

Leu Ala Thr Cys Val Asn Gly Val Cys Trp Thr Val Tyr
```

```
                35                  40                  45

<210> SEQ ID NO 80
<211> LENGTH: 45
<212> TYPE: PRT
<213> ORGANISM: artificial sequence
<220> FEATURE:
<223> OTHER INFORMATION: anti-HCV immunogenic peptide

<400> SEQUENCE: 80

Gly Leu Phe Ser Thr Ile Ile Thr Ser Leu Thr Gly Arg Asp Thr Asn
1               5                   10                  15

Glu Asn Cys Gly Glu Val Gln Val Leu Ser Thr Ala Thr Gln Ser Phe
            20                  25                  30

Leu Gly Thr Ala Val Asn Gly Val Met Trp Thr Val Tyr
        35                  40                  45

<210> SEQ ID NO 81
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 81

Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Asp Gly Glu
            20                  25                  30

Val Gln Val Leu Ser Thr Ala Thr Gln Ser Phe Leu Ala Thr Cys Val
        35                  40                  45

Asn Gly Val Cys Trp Thr Val Tyr His Gly Ala Gly Ser Lys Thr
    50                  55                  60

<210> SEQ ID NO 82
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 82

Ala Pro Ile Thr Ala Tyr Ala Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Ile Val Ser Thr Ala Ala Gln Thr Phe Leu Ala Thr Cys Ile
        35                  40                  45

Asn Gly Val Cys Trp Thr Val Tyr His Gly Ala Gly Thr Arg Thr
    50                  55                  60

<210> SEQ ID NO 83
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 83

Ala Pro Ile Thr Ala Tyr Thr Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30
```

```
Val Gln Ile Val Ser Thr Ala Thr Gln Thr Phe Leu Ala Thr Cys Ile
            35                  40                  45

Asn Gly Val Cys Trp Thr Val Tyr His Gly Ala Gly Thr Arg Thr
        50                  55                  60
```

<210> SEQ ID NO 84
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 84

```
Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
            35                  40                  45

Asn Gly Val Cys Trp Thr Val Tyr His Gly Ala Gly Ser Lys Thr
        50                  55                  60
```

<210> SEQ ID NO 85
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 85

```
Ala Pro Ile Thr Ala Tyr Ser Gln Gln Thr Arg Gly Leu Leu Gly Cys
1               5                   10                  15

Ile Ile Thr Ser Leu Thr Gly Arg Asp Arg Asn Gln Val Glu Gly Glu
            20                  25                  30

Val Gln Val Val Ser Thr Ala Thr Gln Ser Phe Leu Ala Thr Cys Val
            35                  40                  45

Asn Gly Val Cys Trp Thr Val Tyr His Gly Ala Gly Ser Lys Thr
        50                  55                  60
```

<210> SEQ ID NO 86
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 86

```
Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Ile
            35                  40                  45

Asn Gly Val Cys Trp Thr Val Tyr His Gly Ala Gly Ser Lys Thr
        50                  55                  60
```

<210> SEQ ID NO 87
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 87

Ala Pro Ile Thr Ala Tyr Ser Gln Gln Thr Arg Gly Leu Phe Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Tyr His Gly Ala Gly Ser Lys Thr
    50                  55                  60

<210> SEQ ID NO 88
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 88

Ala Pro Ile Thr Ala Tyr Ser Gln Gln Thr Arg Gly Val Leu Gly Cys
1               5                   10                  15

Val Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Ile
        35                  40                  45

Asn Gly Val Cys Trp Thr Val Tyr His Gly Ala Gly Ser Lys Thr
    50                  55                  60

<210> SEQ ID NO 89
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 89

Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Ala Cys Trp Thr Val Phe His Gly Ala Gly Ser Lys Thr
    50                  55                  60

<210> SEQ ID NO 90
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 90

Ala Pro Ile Thr Ala Tyr Ser Arg Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Tyr His Gly Ala Gly Ser Lys Thr
    50                  55                  60

```
<210> SEQ ID NO 91
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 91

Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Ile
        35                  40                  45

Asn Gly Val Cys Trp Thr Val Phe His Gly Ala Gly Ala Lys Thr
    50                  55                  60

<210> SEQ ID NO 92
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 92

Ala Pro Ile Thr

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Phe His Gly Ala Gly Ser Lys Thr
    50                  55                  60

<210> SEQ ID NO 95
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 95

Ala Pro Ile Thr Ala Tyr Ser Gln Gln Thr Arg Gly Leu Leu Gly Cys
1               5                   10                  15

Ile Val Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Ala Cys Trp Thr Val Phe His Gly Ala Gly Ser Lys Thr
    50                  55                  60

<210> SEQ ID NO 96
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 96

Ala Pro Ile Thr Ala Tyr Ala Gln Gln Thr Arg Gly Val Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Phe His Gly Ala Gly Ser Lys Thr
    50                  55                  60

<210> SEQ ID NO 97
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 97

Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Asp Gly Glu
            20                  25                  30

Val Gln Val Leu Ser Thr Ala Thr Gln Ser Phe Leu Ala Thr Cys Ile
        35                  40                  45

Asn Gly Val Cys Trp Thr Val Tyr His Gly Ala Gly Ser Lys Thr
    50                  55                  60

<210> SEQ ID NO 98
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 98

Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Ala Cys Trp Thr Val Tyr His Gly Ala Gly Ser Lys Thr
    50                  55                  60

<210> SEQ ID NO 99
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 99

Ala Pro Ile Thr Ala Tyr Ser Gln Gln Thr Arg Gly Val Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr His Ser Phe Leu Ala Thr Cys Ile
        35                  40                  45

Asn Gly Val Cys Trp Thr Val Tyr His Gly Ala Gly Ser Lys Thr
    50                  55                  60

<210> SEQ ID NO 100
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 100

Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Ile
        35                  40                  45

Asn Gly Ala Cys Trp Thr Val Tyr His Gly Ala Gly Ser Lys Thr
    50                  55                  60

<210> SEQ ID NO 101
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 101

Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Ser Cys Val
        35                  40                  45

```
Asn Gly Val Cys Trp Thr Val Tyr His Gly Ala Gly Ser Lys Thr
    50                  55                  60

<210> SEQ ID NO 102
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 102

Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Thr
        35                  40                  45

Asn Gly Val Cys Trp Thr Val Tyr His Gly Ala Gly Ser Lys Thr
    50                  55                  60

<210> SEQ ID NO 103
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 103

Ala Pro Ile Thr Ala Tyr Ser Gln Gln Thr Arg Gly Val Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Tyr His Gly Ala Gly Ser Lys Thr
    50                  55                  60

<210> SEQ ID NO 104
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 104

Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Lys Ser Phe Leu Ala Thr Cys Val
        35                  40                  45

Asn Gly Val Cys Trp Thr Val Tyr His Gly Ala Gly Ser Lys Thr
    50                  55                  60

<210> SEQ ID NO 105
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 105

Ala Pro Ile Thr Ala Tyr Cys Gln Gln Thr Arg Gly Leu Leu Gly Cys
```

```
                1               5                  10                 15
Ile Ile Thr Ser Leu Thr Gly Arg Asp Lys Asn Gln Val Glu Gly Glu
                    20                 25                 30

Val Gln Val Val Ser Thr Ala Thr Gln Ser Phe Leu Ala Thr Cys Val
            35                 40                 45

Asn Gly Val Cys Trp Thr Val Tyr His Gly Ala Gly Ser Lys Thr
        50                 55                 60

<210> SEQ ID NO 106
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 106

Ala Pro Ile Thr Ala Tyr Ser Gln Gln Thr Arg Gly Leu Leu Gly Cys
1               5                  10                 15

Ile Ile Thr Ser Leu Thr Gly Arg Asp Lys Asn Gln Val Glu Gly Glu
                    20                 25                 30

Val Gln Val Val Ser Thr Ala Lys Gln Ser Phe Leu Ala Thr Cys Val
            35                 40                 45

Asn Gly Ala Cys Trp Thr Val Tyr His Gly Ala Gly Ser Lys Thr
        50                 55                 60

<210> SEQ ID NO 107
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 107

Ala Pro Ile Thr Ala Tyr Ser Gln Gln Thr Arg Gly Leu Leu Gly Cys
1               5                  10                 15

Ile Ile Thr Ser Leu Thr Gly Arg Asp Lys Asn Gln Val Glu Gly Glu
                    20                 25                 30

Val Gln Val Val Ser Thr Ala Thr Gln Ser Phe Leu Ala Thr Cys Val
            35                 40                 45

Asn Gly Val Cys Trp Thr Val Tyr His Gly Ala Gly Thr Lys Thr
        50                 55                 60

<210> SEQ ID NO 108
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 108

Ala Pro Ile Thr Ala Tyr Ser Gln Gln Thr Arg Gly Leu Leu Gly Cys
1               5                  10                 15

Ile Ile Thr Ser Leu Thr Gly Arg Asp Lys Asn Gln Val Glu Gly Glu
                    20                 25                 30

Val Gln Val Val Ser Thr Ala Thr Gln Thr Phe Leu Ala Thr Cys Val
            35                 40                 45

Asn Gly Val Cys Trp Thr Val Phe His Gly Ala Gly Ser Lys Thr
        50                 55                 60

<210> SEQ ID NO 109
<211> LENGTH: 63
```

```
<212> TYPE: PRT
<213> ORGANISM: artificial sequence
<220> FEATURE:
<223> OTHER INFORMATION: anti-HCV immunogenic peptide

<400> SEQUENCE: 109

Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Ala Cys Trp Thr Val Tyr His Gly Ala Gly Thr Lys Thr
    50                  55                  60

<210> SEQ ID NO 110
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 110

Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Phe His Gly Ala Gly Thr Lys Thr
    50                  55                  60

<210> SEQ ID NO 111
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 111

Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Glu Val Ser Thr Ala Thr Gln Ser Phe Leu Ala Thr Cys Val
        35                  40                  45

Asn Gly Val Cys Trp Thr Val Tyr His Gly Ala Gly Ser Lys Ile
    50                  55                  60

<210> SEQ ID NO 112
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 112

Ala Pro Ile Thr Ala Tyr Ser Gln Gln Thr Arg Gly Leu Phe Gly Cys
1               5                   10                  15

Ile Val Thr Ser Leu Thr Gly Arg Asp Lys Asn Gln Val Glu Gly Glu
            20                  25                  30

Ala Gln Val Val Ser Thr Ala Thr Gln Ser Phe Leu Ala Thr Cys Val
```

```
                35                  40                  45

Asn Gly Val Cys Trp Thr Val Tyr His Gly Ala Gly Ser Lys Thr
    50                  55                  60

<210> SEQ ID NO 113
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 113

Ala Pro Ile Thr Ala Tyr Ser Gln Gln Thr Arg Gly Leu Phe Gly Cys
1               5                  10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Ile
        35                  40                  45

Asn Gly Val Cys Trp Thr Val Tyr His Gly Ala Gly Ser Lys Thr
    50                  55                  60

<210> SEQ ID NO 114
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 114

Ala Pro Ile Thr Ala Tyr Ser Gln Gln Thr Arg Gly Leu Ala Gly Cys
1               5                  10                  15

Ile Val Thr Ser Leu Thr Gly Arg Asp Lys Asn Gln Val Glu Gly Glu
            20                  25                  30

Ala Gln Val Val Ser Thr Ala Thr Gln Ser Phe Leu Ala Thr Cys Val
        35                  40                  45

Asn Gly Ala Cys Trp Thr Val Tyr His Gly Ala Gly Ser Lys Thr
    50                  55                  60

<210> SEQ ID NO 115
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 115

Ala Pro Ile Thr Ala Tyr Ser Gln Gln Thr Arg Gly Val Leu Gly Cys
1               5                  10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Phe His Gly Ala Gly Ser Lys Thr
    50                  55                  60

<210> SEQ ID NO 116
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 116
```

Ala Pro Ile Thr Thr Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Tyr His Gly Ala Gly Thr Lys Thr
    50                  55                  60

<210> SEQ ID NO 117
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 117

Ala Ser Ile Thr Ala Tyr Ser Gln Gln Thr Arg Gly Val Leu Gly Cys
1               5                   10                  15

Ile Val Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Ile
        35                  40                  45

Asn Gly Val Cys Trp Thr Val Tyr His Gly Ala Gly Ser Lys Thr
    50                  55                  60

<210> SEQ ID NO 118
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 118

Ala Ser Ile Thr Ala Tyr Ser Gln Gln Thr Arg Gly Leu Leu Gly Cys
1               5                   10                  15

Ile Val Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Phe His Gly Ala Gly Ser Lys Thr
    50                  55                  60

<210> SEQ ID NO 119
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 119

Ala Pro Ile Thr Ala Tyr Ala Gln Gln Thr Arg Gly Leu Leu Gly Cys
1               5                   10                  15

Ile Val Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Phe His Gly Ala Gly Ser Lys Thr
    50                  55                  60

```
<210> SEQ ID NO 120
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 120

Ala Pro Ile Thr Ala Tyr Ala Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Ile
        35                  40                  45

Asn Gly Val Cys Trp Thr Val Tyr His Gly Ala Gly Ser Lys Thr
    50                  55                  60

<210> SEQ ID NO 121
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 121

Ala Pro Ile Thr Ala Tyr Ala Gln Gln Thr Arg Gly Leu Phe Gly Cys
1               5                   10                  15

Ile Ile Thr Ser Leu Thr Gly Arg Asp Arg Asn Gln Val Glu Gly Glu
            20                  25                  30

Val Gln Val Val Ser Thr Ala Thr Gln Ser Phe Leu Ala Thr Cys Ile
        35                  40                  45

Asn Gly Val Cys Trp Thr Val Tyr His Gly Ala Gly Ser Lys Thr
    50                  55                  60

<210> SEQ ID NO 122
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 122

Ala Pro Ile Thr Ala Tyr Ala Gln Gln Thr Arg Gly Leu Phe Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Ile
        35                  40                  45

Asn Gly Val Cys Trp Thr Val Tyr His Gly Ala Gly Ser Lys Thr
    50                  55                  60

<210> SEQ ID NO 123
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 123

Ala Pro Ile Thr Ala Tyr Ser Gln Gln Thr Arg Gly Leu Leu Gly Cys
1               5                   10                  15

Ile Ile Thr Ser Leu Thr Gly Arg Asp Arg Asn Gln Val Glu Gly Glu
            20                  25                  30
```

```
Val Gln Val Val Ser Thr Ala Thr Gln Ser Phe Leu Ala Thr Cys Ile
         35                  40                  45

Asn Gly Val Cys Trp Thr Val Phe His Gly Ala Gly Ser Lys Thr
     50                  55                  60

<210> SEQ ID NO 124
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 124

Ala Pro Ile Thr Ala Tyr Ser Gln Gln Thr Arg Gly Leu Leu Gly Cys
1               5                   10                  15

Ile Ile Thr Ser Leu Thr Gly Arg Asp Arg Asn Gln Val Glu Gly Glu
            20                  25                  30

Val Gln Val Val Ser Thr Ala Thr Gln Ser Phe Leu Ala Thr Cys Val
         35                  40                  45

Asn Gly Val Cys Trp Thr Val Tyr His Gly Ala Gly Ala Lys Thr
     50                  55                  60

<210> SEQ ID NO 125
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 125

Ala His Ile Thr Ala Tyr Ser Gln Gln Thr Arg Gly Leu Leu Gly Cys
1               5                   10                  15

Ile Ile Thr Ser Leu Thr Gly Arg Asp Arg Asn Gln Val Glu Gly Glu
            20                  25                  30

Val Gln Met Val Ser Thr Ala Thr Gln Ser Phe Leu Ala Thr Cys Val
         35                  40                  45

Asn Gly Val Cys Trp Thr Val Tyr His Gly Ala Gly Ser Lys Thr
     50                  55                  60

<210> SEQ ID NO 126
<211> LENGTH: 63
<212> TYPE: PRT
<213> ORGANISM: artificial sequence
<220> FEATURE:
<223> OTHER INFORMATION: anti-HCV immunogenic peptide

<400> SEQUENCE: 126

Ala Pro Ile Thr Ala Tyr Ser Gln Gln Thr Arg Gly Leu Phe Ser Thr
1               5                   10                  15

Ile Ile Thr Ser Leu Thr Gly Arg Asp Thr Asn Glu Asn Cys Gly Glu
            20                  25                  30

Val Gln Val Leu Ser Thr Ala Thr Gln Ser Phe Leu Gly Thr Cys Val
         35                  40                  45

Asn Gly Val Met Trp Thr Val Tyr His Gly Ala Gly Ala Lys Thr
     50                  55                  60

<210> SEQ ID NO 127
<211> LENGTH: 32
<212> TYPE: PRT
<213> ORGANISM: artificial sequence
<220> FEATURE:
<223> OTHER INFORMATION: anti-HCV immunogenic peptide
```

```
<220> FEATURE:
<221> NAME/KEY: MISC_FEATURE
<222> LOCATION: (2)..(2)
<223> OTHER INFORMATION: Xaa = L or P
<220> FEATURE:
<221> NAME/KEY: MISC_FEATURE
<222> LOCATION: (4)..(4)
<223> OTHER INFORMATION: Xaa = A or S
<220> FEATURE:
<221> NAME/KEY: MISC_FEATURE
<222> LOCATION: (7)..(7)
<223> OTHER INFORMATION: Xaa = A or S
<220> FEATURE:
<221> NAME/KEY: MISC_FEATURE
<222> LOCATION: (8)..(8)
<223> OTHER INFORMATION: Xaa = A or S
<220> FEATURE:
<221> NAME/KEY: MISC_FEATURE
<222> LOCATION: (9)..(9)
<223> OTHER INFORMATION: Xaa = I or V
<220> FEATURE:
<221> NAME/KEY: MISC_FEATURE
<222> LOCATION: (14)..(14)
<223> OTHER INFORMATION: Xaa = T, S or A
<220> FEATURE:
<221> NAME/KEY: MISC_FEATURE
<222> LOCATION: (15)..(15)
<223> OTHER INFORMATION: Xaa = T or I
<220> FEATURE:
<221> NAME/KEY: MISC_FEATURE
<222> LOCATION: (16)..(16)
<223> OTHER INFORMATION: Xaa = Q, S or G
<220> FEATURE:
<221> NAME/KEY: MISC_FEATURE
<222> LOCATION: (17)..(17)
<223> OTHER INFORMATION: Xaa = N, Q, H, S, Y or T
<220> FEATURE:
<221> NAME/KEY: MISC_FEATURE
<222> LOCATION: (20)..(20)
<223> OTHER INFORMATION: Xaa = L or M
<220> FEATURE:
<221> NAME/KEY: MISC_FEATURE
<222> LOCATION: (24)..(24)
<223> OTHER INFORMATION: Xaa = L or W
<220> FEATURE:
<221> NAME/KEY: MISC_FEATURE
<222> LOCATION: (30)..(30)
<223> OTHER INFORMATION: Xaa = A or S
<220> FEATURE:
<221> NAME/KEY: MISC_FEATURE
<222> LOCATION: (32)..(32)
<223> OTHER INFORMATION: Xaa = L, P or I

<400> SEQUENCE: 127

Ser Xaa Met Xaa Phe Thr Xaa Xaa Xaa Thr Ser Pro Leu Xaa Xaa Xaa
1               5                   10                  15

Xaa Thr Leu Xaa Phe Asn Ile Xaa Gly Gly Trp Val Ala Xaa Gln Xaa
            20                  25                  30

<210> SEQ ID NO 128
<211> LENGTH: 57
<212> TYPE: PRT
<213> ORGANISM: artificial sequence
<220> FEATURE:
<223> OTHER INFORMATION: anti-HCV immunogenic peptide
<220> FEATURE:
<221> NAME/KEY: MISC_FEATURE
<222> LOCATION: (4)..(4)
<223> OTHER INFORMATION: Xaa = T or S
<220> FEATURE:
<221> NAME/KEY: MISC_FEATURE
<222> LOCATION: (6)..(6)
<223> OTHER INFORMATION: Xaa = I, T or V
<220> FEATURE:
<221> NAME/KEY: MISC_FEATURE
<222> LOCATION: (11)..(11)
<223> OTHER INFORMATION: Xaa = G or A
```

```
<220> FEATURE:
<221> NAME/KEY: MISC_FEATURE
<222> LOCATION: (19)..(19)
<223> OTHER INFORMATION: Xaa = P or L
<220> FEATURE:
<221> NAME/KEY: MISC_FEATURE
<222> LOCATION: (21)..(21)
<223> OTHER INFORMATION: Xaa = I or M
<220> FEATURE:
<221> NAME/KEY: MISC_FEATURE
<222> LOCATION: (22)..(22)
<223> OTHER INFORMATION: Xaa = A, V or R
<220> FEATURE:
<221> NAME/KEY: MISC_FEATURE
<222> LOCATION: (24)..(24)
<223> OTHER INFORMATION: Xaa = L or P
<220> FEATURE:
<221> NAME/KEY: MISC_FEATURE
<222> LOCATION: (26)..(26)
<223> OTHER INFORMATION: Xaa = A or S
<220> FEATURE:
<221> NAME/KEY: MISC_FEATURE
<222> LOCATION: (29)..(29)
<223> OTHER INFORMATION: Xaa = A or S
<220> FEATURE:
<221> NAME/KEY: MISC_FEATURE
<222> LOCATION: (30)..(30)
<223> OTHER INFORMATION: Xaa = A or S
<220> FEATURE:
<221> NAME/KEY: MISC_FEATURE
<222> LOCATION: (31)..(31)
<223> OTHER INFORMATION: Xaa = I or V
<220> FEATURE:
<221> NAME/KEY: MISC_FEATURE
<222> LOCATION: (36)..(36)
<223> OTHER INFORMATION: Xaa = T, S or A
<220> FEATURE:
<221> NAME/KEY: MISC_FEATURE
<222> LOCATION: (37)..(37)
<223> OTHER INFORMATION: Xaa = T or I
<220> FEATURE:
<221> NAME/KEY: MISC_FEATURE
<222> LOCATION: (38)..(38)
<223> OTHER INFORMATION: Xaa = Q, S or G
<220> FEATURE:
<221> NAME/KEY: MISC_FEATURE
<222> LOCATION: (39)..(39)
<223> OTHER INFORMATION: Xaa = N, Q, H, S, Y or T
<220> FEATURE:
<221> NAME/KEY: MISC_FEATURE
<222> LOCATION: (42)..(42)
<223> OTHER INFORMATION: Xaa = L or M
<220> FEATURE:
<221> NAME/KEY: MISC_FEATURE
<222> LOCATION: (46)..(46)
<223> OTHER INFORMATION: Xaa = L or W
<220> FEATURE:
<221> NAME/KEY: MISC_FEATURE
<222> LOCATION: (52)..(52)
<223> OTHER INFORMATION: Xaa = A or S
<220> FEATURE:
<221> NAME/KEY: MISC_FEATURE
<222> LOCATION: (54)..(54)
<223> OTHER INFORMATION: Xaa = L, P or I
<220> FEATURE:
<221> NAME/KEY: MISC_FEATURE
<222> LOCATION: (55)..(55)
<223> OTHER INFORMATION: Xaa = A or R
<220> FEATURE:
<221> NAME/KEY: MISC_FEATURE
<222> LOCATION: (56)..(56)
<223> OTHER INFORMATION: Xaa = P, A or D
<220> FEATURE:
<221> NAME/KEY: MISC_FEATURE
<222> LOCATION: (57)..(57)
<223> OTHER INFORMATION: Xaa = P, A or S

<400> SEQUENCE: 128

Asn Phe Ile Xaa Gly Xaa Gln Tyr Leu Ala Xaa Leu Ser Thr Leu Pro
```

```
                1               5              10              15
Gly Asn Xaa Ala Xaa Xaa Ser Xaa Met Xaa Phe Thr Xaa Xaa Xaa Thr
                20                  25                  30

Ser Pro Leu Xaa Xaa Xaa Xaa Thr Leu Xaa Phe Asn Ile Xaa Gly Gly
            35                  40                  45

Trp Val Ala Xaa Gln Xaa Xaa Xaa Xaa
            50                  55
```

```
<210> SEQ ID NO 129
<211> LENGTH: 32
<212> TYPE: PRT
<213> ORGANISM: artificial sequence
<220> FEATURE:
<223> OTHER INFORMATION: anti-HCV immunogenic peptide

<400> SEQUENCE: 129

Ser Leu Met Ala Phe Thr Ala Ser Ile Thr Ser Pro Leu Thr Thr Gln
1               5                   10                  15

Asn Thr Leu Leu Phe Asn Ile Leu Gly Gly Trp Val Ala Ala Gln Leu
                20                  25                  30

<210> SEQ ID NO 130
<211> LENGTH: 32
<212> TYPE: PRT
<213> ORGANISM: artificial sequence
<220> FEATURE:
<223> OTHER INFORMATION: anti-HCV immunogenic peptide

<400> SEQUENCE: 130

Ser Leu Met Ala Phe Thr Ala Ala Val Thr Ser Pro Leu Thr Thr Ser
1               5                   10                  15

Gln Thr Leu Leu Phe Asn Ile Leu Gly Gly Trp Val Ala Ala Gln Leu
                20                  25                  30

<210> SEQ ID NO 131
<211> LENGTH: 32
<212> TYPE: PRT
<213> ORGANISM: artificial sequence
<220> FEATURE:
<223> OTHER INFORMATION: anti-HCV immunogenic peptide

<400> SEQUENCE: 131

Ser Leu Met Ala Phe Thr Ala Ala Val Thr Ser Pro Leu Thr Thr Gly
1               5                   10                  15

Gln Thr Leu Leu Phe Asn Ile Leu Gly Gly Trp Val Ala Ala Gln Leu
                20                  25                  30

<210> SEQ ID NO 132
<211> LENGTH: 32
<212> TYPE: PRT
<213> ORGANISM: artificial sequence
<220> FEATURE:
<223> OTHER INFORMATION: anti-HCV immunogenic peptide

<400> SEQUENCE: 132

Ser Leu Met Ala Phe Thr Ala Ser Ile Thr Ser Pro Leu Thr Thr Gln
1               5                   10                  15

His Thr Leu Leu Phe Asn Ile Leu Gly Gly Trp Val Ala Ala Gln Leu
                20                  25                  30

<210> SEQ ID NO 133
<211> LENGTH: 32
<212> TYPE: PRT
<213> ORGANISM: artificial sequence
```

```
<220> FEATURE:
<223> OTHER INFORMATION: anti-HCV immunogenic peptide

<400> SEQUENCE: 133

Ser Leu Met Ala Phe Thr Ala Ser Ile Thr Ser Pro Leu Thr Thr Gln
1               5                   10                  15

Ser Thr Leu Leu Phe Asn Ile Leu Gly Gly Trp Val Ala Ala Gln Leu
            20                  25                  30

<210> SEQ ID NO 134
<211> LENGTH: 32
<212> TYPE: PRT
<213> ORGANISM: artificial sequence
<220> FEATURE:
<223> OTHER INFORMATION: anti-HCV immunogenic peptide

<400> SEQUENCE: 134

Ser Leu Met Ala Phe Thr Ala Ser Ile Thr Ser Pro Leu Thr Thr Gln
1               5                   10                  15

Tyr Thr Leu Leu Phe Asn Ile Leu Gly Gly Trp Val Ala Ala Gln Leu
            20                  25                  30

<210> SEQ ID NO 135
<211> LENGTH: 32
<212> TYPE: PRT
<213> ORGANISM: artificial sequence
<220> FEATURE:
<223> OTHER INFORMATION: anti-HCV immunogenic peptide

<400> SEQUENCE: 135

Ser Leu Met Ala Phe Thr Ala Ser Val Thr Ser Pro Leu Thr Thr Gln
1               5                   10                  15

Asn Thr Leu Leu Phe Asn Ile Leu Gly Gly Trp Val Ala Ala Gln Leu
            20                  25                  30

<210> SEQ ID NO 136
<211> LENGTH: 32
<212> TYPE: PRT
<213> ORGANISM: artificial sequence
<220> FEATURE:
<223> OTHER INFORMATION: anti-HCV immunogenic peptide

<400> SEQUENCE: 136

Ser Leu Met Ala Phe Thr Ala Ser Val Thr Ser Pro Leu Thr Thr Gln
1               5                   10                  15

Ser Thr Leu Leu Phe Asn Ile Leu Gly Gly Trp Val Ala Ala Gln Leu
            20                  25                  30

<210> SEQ ID NO 137
<211> LENGTH: 32
<212> TYPE: PRT
<213> ORGANISM: artificial sequence
<220> FEATURE:
<223> OTHER INFORMATION: anti-HCV immunogenic peptide

<400> SEQUENCE: 137

Ser Leu Met Ala Phe Thr Ala Ser Ile Thr Ser Pro Leu Thr Thr Gln
1               5                   10                  15

Thr Thr Leu Met Phe Asn Ile Leu Gly Gly Trp Val Ala Ala Gln Leu
            20                  25                  30

<210> SEQ ID NO 138
<211> LENGTH: 32
<212> TYPE: PRT
<213> ORGANISM: artificial sequence
```

<220> FEATURE:
<223> OTHER INFORMATION: anti-HCV immunogenic peptide

<400> SEQUENCE: 138

Ser Leu Met Ala Phe Thr Ala Ser Val Thr Ser Pro Leu Thr Thr Gln
1               5                   10                  15

Tyr Thr Leu Leu Phe Asn Ile Leu Gly Gly Trp Val Ala Ala Gln Ile
            20                  25                  30

<210> SEQ ID NO 139
<211> LENGTH: 32
<212> TYPE: PRT
<213> ORGANISM: artificial sequence
<220> FEATURE:
<223> OTHER INFORMATION: anti-HCV immunogenic peptide

<400> SEQUENCE: 139

Ser Pro Met Ala Phe Thr Ala Ser Ile Thr Ser Pro Leu Thr Thr Gln
1               5                   10                  15

His Thr Leu Leu Phe Asn Ile Leu Gly Gly Trp Val Ala Ala Gln Leu
            20                  25                  30

<210> SEQ ID NO 140
<211> LENGTH: 32
<212> TYPE: PRT
<213> ORGANISM: artificial sequence
<220> FEATURE:
<223> OTHER INFORMATION: anti-HCV immunogenic peptide

<400> SEQUENCE: 140

Ser Leu Met Ala Phe Thr Ala Ser Ile Thr Ser Pro Leu Thr Ile Gln
1               5                   10                  15

His Thr Leu Leu Phe Asn Ile Leu Gly Gly Trp Val Ala Ala Gln Pro
            20                  25                  30

<210> SEQ ID NO 141
<211> LENGTH: 32
<212> TYPE: PRT
<213> ORGANISM: artificial sequence
<220> FEATURE:
<223> OTHER INFORMATION: anti-HCV immunogenic peptide

<400> SEQUENCE: 141

Ser Leu Met Ala Phe Thr Ser Ser Ile Thr Ser Pro Leu Thr Thr Gln
1               5                   10                  15

Ser Thr Leu Leu Phe Asn Ile Leu Gly Gly Trp Val Ala Ala Gln Leu
            20                  25                  30

<210> SEQ ID NO 142
<211> LENGTH: 32
<212> TYPE: PRT
<213> ORGANISM: artificial sequence
<220> FEATURE:
<223> OTHER INFORMATION: anti-HCV immunogenic peptide

<400> SEQUENCE: 142

Ser Leu Met Ala Phe Thr Ala Ser Ile Thr Ser Pro Leu Ser Thr Gln
1               5                   10                  15

Asn Thr Leu Leu Phe Asn Ile Trp Gly Gly Trp Val Ala Ala Gln Leu
            20                  25                  30

<210> SEQ ID NO 143
<211> LENGTH: 32
<212> TYPE: PRT
<213> ORGANISM: artificial sequence -continued

```
<220> FEATURE:
<223> OTHER INFORMATION: anti-HCV immunogenic peptide

<400> SEQUENCE: 143

Ser Leu Met Ala Phe Thr Ala Ser Ile Thr Ser Pro Leu Thr Thr Gln
1               5                   10                  15

Asn Thr Leu Met Phe Asn Ile Leu Gly Gly Trp Val Ala Ala Gln Leu
            20                  25                  30

<210> SEQ ID NO 144
<211> LENGTH: 32
<212> TYPE: PRT
<213> ORGANISM: artificial sequence
<220> FEATURE:
<223> OTHER INFORMATION: anti-HCV immunogenic peptide

<400> SEQUENCE: 144

Ser Leu Met Ala Phe Thr Ala Ser Ile Thr Ser Pro Leu Thr Thr Gln
1               5                   10                  15

His Thr Leu Met Phe Asn Ile Leu Gly Gly Trp Val Ala Ala Gln Leu
            20                  25                  30

<210> SEQ ID NO 145
<211> LENGTH: 32
<212> TYPE: PRT
<213> ORGANISM: artificial sequence
<220> FEATURE:
<223> OTHER INFORMATION: anti-HCV immunogenic peptide

<400> SEQUENCE: 145

Ser Leu Met Ala Phe Thr Ala Ser Ile Thr Ser Pro Leu Ala Thr Gln
1               5                   10                  15

Tyr Thr Leu Leu Phe Asn Ile Leu Gly Gly Trp Val Ala Ala Gln Leu
            20                  25                  30

<210> SEQ ID NO 146
<211> LENGTH: 32
<212> TYPE: PRT
<213> ORGANISM: artificial sequence
<220> FEATURE:
<223> OTHER INFORMATION: anti-HCV immunogenic peptide

<400> SEQUENCE: 146

Ser Leu Met Ser Phe Thr Ala Ala Val Thr Ser Pro Leu Thr Thr Gln
1               5                   10                  15

Gln Thr Leu Leu Phe Asn Ile Leu Gly Gly Trp Val Ala Ser Gln Ile
            20                  25                  30

<210> SEQ ID NO 147
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 147

Asn Phe Ile Thr Gly Ile Gln Tyr Leu Ala Gly Leu Ser Thr Leu Pro
1               5                   10                  15

Gly Asn Pro Ala Ile Ala Ser Leu Met Ala Phe Thr Ala Ser Ile Thr
            20                  25                  30

Ser Pro Leu Thr Thr Gln Asn Thr Leu Leu Phe Asn Ile Leu Gly Gly
        35                  40                  45

Trp Val Ala Ala Gln Leu Ala Pro Pro
    50                  55
```

<210> SEQ ID NO 148
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 148

Asn Phe Ile Ser Gly Ile Gln Tyr Leu Ala Gly Leu Ser Thr Leu Pro
1               5                   10                  15

Gly Asn Pro Ala Ile Ala Ser Leu Met Ala Phe Thr Ala Ala Val Thr
            20                  25                  30

Ser Pro Leu Thr Thr Ser Gln Thr Leu Leu Phe Asn Ile Leu Gly Gly
        35                  40                  45

Trp Val Ala Ala Gln Leu Ala Ala Pro
    50                  55

<210> SEQ ID NO 149
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 149

Asn Phe Ile Ser Gly Ile Gln Tyr Leu Ala Gly Leu Ser Thr Leu Pro
1               5                   10                  15

Gly Asn Pro Ala Ile Ala Ser Leu Met Ala Phe Thr Ala Ala Val Thr
            20                  25                  30

Ser Pro Leu Thr Thr Gly Gln Thr Leu Leu Phe Asn Ile Leu Gly Gly
        35                  40                  45

Trp Val Ala Ala Gln Leu Ala Ala Pro
    50                  55

<210> SEQ ID NO 150
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 150

Asn Phe Ile Ser Gly Thr Gln Tyr Leu Ala Gly Leu Ser Thr Leu Pro
1               5                   10                  15

Gly Asn Pro Ala Ile Ala Ser Leu Met Ala Phe Thr Ala Ala Val Thr
            20                  25                  30

Ser Pro Leu Thr Thr Ser Gln Thr Leu Leu Phe Asn Ile Leu Gly Gly
        35                  40                  45

Trp Val Ala Ala Gln Leu Ala Ala Pro
    50                  55

<210> SEQ ID NO 151
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 151

Asn Phe Ile Ser Gly Ile Gln Tyr Leu Ala Gly Leu Ser Thr Leu Pro
1               5                   10                  15

Gly Asn Pro Ala Ile Ala Ser Leu Met Ala Phe Thr Ala Ser Ile Thr
            20                  25                  30

Ser Pro Leu Thr Thr Gln His Thr Leu Leu Phe Asn Ile Leu Gly Gly
        35                  40                  45

Trp Val Ala Ala Gln Leu Ala Pro Pro
    50                  55

<210> SEQ ID NO 152
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 152

Asn Phe Ile Ser Gly Ile Gln Tyr Leu Ala Gly Leu Ser Thr Leu Pro
1               5                   10                  15

Gly Asn Pro Ala Ile Ala Ser Leu Met Ala Phe Thr Ala Ser Ile Thr
            20                  25                  30

Ser Pro Leu Thr Thr Gln Ser Thr Leu Leu Phe Asn Ile Leu Gly Gly
        35                  40                  45

Trp Val Ala Ala Gln Leu Ala Pro Pro
    50                  55

<210> SEQ ID NO 153
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 153

Asn Phe Ile Ser Gly Ile Gln Tyr Leu Ala Gly Leu Ser Thr Leu Pro
1               5                   10                  15

Gly Asn Pro Ala Ile Ala Ser Leu Met Ala Phe Thr Ala Ser Ile Thr
            20                  25                  30

Ser Pro Leu Thr Thr Gln Asn Thr Leu Leu Phe Asn Ile Leu Gly Gly
        35                  40                  45

Trp Val Ala Ala Gln Leu Ala Pro Pro
    50                  55

<210> SEQ ID NO 154
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 154

Asn Phe Ile Ser Gly Ile Gln Tyr Leu Ala Gly Leu Ser Thr Leu Pro
1               5                   10                  15

Gly Asn Pro Ala Ile Ala Ser Leu Met Ala Phe Thr Ala Ser Ile Thr
            20                  25                  30

Ser Pro Leu Thr Thr Gln Tyr Thr Leu Leu Phe Asn Ile Leu Gly Gly
        35                  40                  45

Trp Val Ala Ala Gln Leu Ala Pro Pro
    50                  55

<210> SEQ ID NO 155
<211> LENGTH: 57
<212> TYPE: PRT
<213> ORGANISM: artificial sequence

```
<220> FEATURE:
<223> OTHER INFORMATION: anti-HCV immunogenic peptide

<400> SEQUENCE: 155

Asn Phe Ile Ser Gly Ile Gln Tyr Leu Ala Gly Leu Ser Thr Leu Pro
1               5                   10                  15

Gly Asn Pro Ala Ile Val Ser Leu Met Ala Phe Thr Ala Ser Ile Thr
            20                  25                  30

Ser Pro Leu Thr Thr Gln His Thr Leu Leu Phe Asn Ile Leu Gly Gly
        35                  40                  45

Trp Val Ala Ala Gln Leu Ala Pro Pro
    50                  55

<210> SEQ ID NO 156
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 156

Asn Phe Ile Ser Gly Ile Gln Tyr Leu Ala Gly Leu Ser Thr Leu Pro
1               5                   10                  15

Gly Asn Pro Ala Ile Ala Ser Leu Met Ala Phe Thr Ala Ser Val Thr
            20                  25                  30

Ser Pro Leu Thr Thr Gln Asn Thr Leu Leu Phe Asn Ile Leu Gly Gly
        35                  40                  45

Trp Val Ala Ala Gln Leu Ala Pro Pro
    50                  55

<210> SEQ ID NO 157
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 157

Asn Phe Ile Ser Gly Ile Gln Tyr Leu Ala Gly Leu Ser Thr Leu Pro
1               5                   10                  15

Gly Asn Pro Ala Ile Ala Ser Leu Met Ala Phe Thr Ala Ser Val Thr
            20                  25                  30

Ser Pro Leu Thr Thr Gln Ser Thr Leu Leu Phe Asn Ile Leu Gly Gly
        35                  40                  45

Trp Val Ala Ala Gln Leu Ala Pro Pro
    50                  55

<210> SEQ ID NO 158
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 158

Asn Phe Ile Ser Gly Ile Gln Tyr Leu Ala Gly Leu Ser Thr Leu Pro
1               5                   10                  15

Gly Asn Pro Ala Ile Ala Ser Leu Met Ala Phe Thr Ala Ser Ile Thr
            20                  25                  30

Ser Pro Leu Thr Thr Gln Thr Thr Leu Met Phe Asn Ile Leu Gly Gly
        35                  40                  45
```

Trp Val Ala Ala Gln Leu Ala Pro Pro
    50                  55

<210> SEQ ID NO 159
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 159

Asn Phe Ile Ser Gly Ile Gln Tyr Leu Ala Gly Leu Ser Thr Leu Pro
1               5                   10                  15

Gly Asn Pro Ala Ile Ala Ser Leu Met Ala Phe Thr Ala Ser Val Thr
            20                  25                  30

Ser Pro Leu Thr Thr Gln Tyr Thr Leu Leu Phe Asn Ile Leu Gly Gly
        35                  40                  45

Trp Val Ala Ala Gln Ile Ala Pro Pro
    50                  55

<210> SEQ ID NO 160
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 160

Asn Phe Ile Ser Gly Ile Gln Tyr Leu Ala Gly Leu Ser Thr Leu Pro
1               5                   10                  15

Gly Asn Pro Ala Ile Arg Ser Pro Met Ala Phe Thr Ala Ser Ile Thr
            20                  25                  30

Ser Pro Leu Thr Thr Gln His Thr Leu Leu Phe Asn Ile Leu Gly Gly
        35                  40                  45

Trp Val Ala Ala Gln Leu Ala Pro Pro
    50                  55

<210> SEQ ID NO 161
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 161

Asn Phe Ile Ser Gly Ile Gln Tyr Leu Ala Gly Leu Ser Thr Leu Pro
1               5                   10                  15

Gly Asn Pro Ala Ile Ala Ser Leu Met Ala Phe Thr Ala Ser Ile Thr
            20                  25                  30

Ser Pro Leu Thr Ile Gln His Thr Leu Leu Phe Asn Ile Leu Gly Gly
        35                  40                  45

Trp Val Ala Ala Gln Pro Ala Pro Pro
    50                  55

<210> SEQ ID NO 162
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 162

Asn Phe Ile Ser Gly Ile Gln Tyr Leu Ala Ala Leu Ser Thr Leu Pro

```
                1               5                  10                 15
Gly Asn Pro Ala Ile Ala Ser Leu Met Ala Phe Thr Ala Ser Ile Thr
                20                  25                 30

Ser Pro Leu Thr Thr Gln Asn Thr Leu Leu Phe Asn Ile Leu Gly Gly
            35                  40                 45

Trp Val Ala Ala Gln Leu Ala Pro Ala
        50                  55

<210> SEQ ID NO 163
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 163

Asn Phe Ile Ser Gly Ile Gln Tyr Leu Ala Gly Leu Ser Thr Leu Pro
1               5                  10                 15

Gly Asn Pro Ala Ile Ala Ser Leu Met Ala Phe Thr Ser Ser Ile Thr
                20                  25                 30

Ser Pro Leu Thr Thr Gln Ser Thr Leu Leu Phe Asn Ile Leu Gly Gly
            35                  40                 45

Trp Val Ala Ala Gln Leu Ala Pro Pro
        50                  55

<210> SEQ ID NO 164
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 164

Asn Phe Ile Ser Gly Ile Gln Tyr Leu Ala Gly Leu Ser Thr Leu Pro
1               5                  10                 15

Gly Asn Pro Ala Ile Ala Ser Leu Met Ala Phe Thr Ala Ser Ile Thr
                20                  25                 30

Ser Pro Leu Ser Thr Gln Asn Thr Leu Leu Phe Asn Ile Trp Gly Gly
            35                  40                 45

Trp Val Ala Ala Gln Leu Ala Pro Pro
        50                  55

<210> SEQ ID NO 165
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 165

Asn Phe Ile Ser Gly Ile Gln Tyr Leu Ala Gly Leu Ser Thr Leu Pro
1               5                  10                 15

Gly Asn Pro Ala Ile Ala Ser Leu Met Ala Phe Thr Ala Ser Ile Thr
                20                  25                 30

Ser Pro Leu Thr Thr Gln Asn Thr Leu Met Phe Asn Ile Leu Gly Gly
            35                  40                 45

Trp Val Ala Ala Gln Leu Ala Pro Pro
        50                  55

<210> SEQ ID NO 166
<211> LENGTH: 57
```

```
<212> TYPE: PRT
<213> ORGANISM: artificial sequence
<220> FEATURE:
<223> OTHER INFORMATION: anti-HCV immunogenic peptide

<400> SEQUENCE: 166

Asn Phe Ile Ser Gly Ile Gln Tyr Leu Ala Gly Leu Ser Thr Leu Pro
1               5                   10                  15

Gly Asn Pro Ala Met Ala Ser Leu Met Ala Phe Thr Ala Ser Ile Thr
            20                  25                  30

Ser Pro Leu Thr Thr Gln His Thr Leu Met Phe Asn Ile Leu Gly Gly
        35                  40                  45

Trp Val Ala Ala Gln Leu Ala Pro Pro
    50                  55

<210> SEQ ID NO 167
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 167

Asn Phe Ile Ser Gly Val Gln Tyr Leu Ala Gly Leu Ser Thr Leu Pro
1               5                   10                  15

Gly Asn Pro Ala Ile Ala Ser Leu Met Ala Phe Thr Ala Ser Ile Thr
            20                  25                  30

Ser Pro Leu Thr Thr Gln Asn Thr Leu Leu Phe Asn Ile Leu Gly Gly
        35                  40                  45

Trp Val Ala Ala Gln Leu Ala Pro Pro
    50                  55

<210> SEQ ID NO 168
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 168

Asn Phe Ile Ser Gly Val Gln Tyr Leu Ala Gly Leu Ser Thr Leu Pro
1               5                   10                  15

Gly Asn Pro Ala Ile Ala Ser Leu Met Ala Phe Thr Ala Ser Ile Thr
            20                  25                  30

Ser Pro Leu Thr Thr Gln His Thr Leu Leu Phe Asn Ile Leu Gly Gly
        35                  40                  45

Trp Val Ala Ala Gln Leu Ala Pro Pro
    50                  55

<210> SEQ ID NO 169
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 169

Asn Phe Ile Ser Gly Val Gln Tyr Leu Ala Gly Leu Ser Thr Leu Pro
1               5                   10                  15

Gly Asn Pro Ala Ile Ala Ser Leu Met Ala Phe Thr Ala Ser Ile Thr
            20                  25                  30

Ser Pro Leu Thr Thr Gln Tyr Thr Leu Leu Phe Asn Ile Leu Gly Gly
```

Trp Val Ala Ala Gln Leu Ala Pro Pro
    50                  55

<210> SEQ ID NO 170
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 170

Asn Phe Ile Ser Gly Val Gln Tyr Leu Ala Gly Leu Ser Thr Leu Pro
1               5                   10                  15

Gly Asn Pro Ala Ile Ala Ser Leu Met Ala Phe Thr Ala Ser Val Thr
            20                  25                  30

Ser Pro Leu Thr Thr Gln Ser Thr Leu Leu Phe Asn Ile Leu Gly Gly
        35                  40                  45

Trp Val Ala Ala Gln Leu Ala Pro Pro
    50                  55

<210> SEQ ID NO 171
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 171

Asn Phe Ile Ser Gly Ile Gln Tyr Leu Ala Gly Leu Ser Thr Leu Pro
1               5                   10                  15

Gly Asn Leu Ala Ile Ala Ser Leu Met Ala Phe Thr Ala Ser Ile Thr
            20                  25                  30

Ser Pro Leu Thr Thr Gln His Thr Leu Leu Phe Asn Ile Leu Gly Gly
        35                  40                  45

Trp Val Ala Ala Gln Leu Ala Pro Pro
    50                  55

<210> SEQ ID NO 172
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 172

Asn Phe Ile Ser Gly Ile Gln Tyr Leu Ala Gly Leu Ser Thr Leu Pro
1               5                   10                  15

Gly Asn Pro Ala Ile Ala Ser Leu Met Ala Phe Thr Ala Ser Ile Thr
            20                  25                  30

Ser Pro Leu Ala Thr Gln Tyr Thr Leu Leu Phe Asn Ile Leu Gly Gly
        35                  40                  45

Trp Val Ala Ala Gln Leu Ala Pro Pro
    50                  55

<210> SEQ ID NO 173
<211> LENGTH: 57
<212> TYPE: PRT
<213> ORGANISM: artificial sequence
<220> FEATURE:
<223> OTHER INFORMATION: anti-HCV immunogenic peptide

<400> SEQUENCE: 173

```
Asn Phe Ile Ser Gly Ile Gln Tyr Leu Ala Gly Leu Ser Thr Leu Pro
 1               5                  10                  15

Gly Asn Pro Ala Ile Ala Ser Leu Met Ser Phe Thr Ala Ala Val Thr
             20                  25                  30

Ser Pro Leu Thr Thr Gln Gln Thr Leu Leu Phe Asn Ile Leu Gly Gly
         35                  40                  45

Trp Val Ala Ser Gln Ile Arg Asp Ser
         50                  55

<210> SEQ ID NO 174
<211> LENGTH: 29
<212> TYPE: PRT
<213> ORGANISM: artificial sequence
<220> FEATURE:
<223> OTHER INFORMATION: anti-HCV immunogenic peptide

```
<210> SEQ ID NO 175
<211> LENGTH: 44
<212> TYPE: PRT
<213> ORGANISM: artificial sequence
<220> FEATURE:
<223> OTHER INFORMATION: anti-HCV immunogenic peptide
<220> FEATURE:
<221> NAME/KEY: MISC_FEATURE
<222> LOCATION: (4)..(4)
<223> OTHER INFORMATION: Xaa = R or Q
<220> FEATURE:
<221> NAME/KEY: MISC_FEATURE
<222> LOCATION: (6)..(6)
<223> OTHER INFORMATION: Xaa = P or A
<220> FEATURE:
<221> NAME/KEY: MISC_FEATURE
<222> LOCATION: (9)..(9)
<223> OTHER INFORMATION: Xaa = L or F
<220> FEATURE:
<221> NAME/KEY: MISC_FEATURE
<222> LOCATION: (12)..(12)
<223> OTHER INFORMATION: Xaa = F or Y
<220> FEATURE:
<221> NAME/KEY: MISC_FEATURE
<222> LOCATION: (14)..(14)
<223> OTHER INFORMATION: Xaa = D or E
<220> FEATURE:
<221> NAME/KEY: MISC_FEATURE
<222> LOCATION: (17)..(17)
<223> OTHER INFORMATION: Xaa = V or S
<220> FEATURE:
<221> NAME/KEY: MISC_FEATURE
<222> LOCATION: (23)..(23)
<223> OTHER INFORMATION: Xaa = M or R
<220> FEATURE:
<221> NAME/KEY: MISC_FEATURE
<222> LOCATION: (26)..(26)
<223> OTHER INFORMATION: Xaa = Y or H
<220> FEATURE:
<221> NAME/KEY: MISC_FEATURE
<222> LOCATION: (27)..(27)
<223> OTHER INFORMATION: Xaa = D or N
<220> FEATURE:
<221> NAME/KEY: MISC_FEATURE
<222> LOCATION: (29)..(29)
<223> OTHER INFORMATION: Xaa = V or I
<220> FEATURE:
<221> NAME/KEY: MISC_FEATURE
<222> LOCATION: (30)..(30)
<223> OTHER INFORMATION: Xaa = S, T or K
<220> FEATURE:
<221> NAME/KEY: MISC_FEATURE
<222> LOCATION: (31)..(31)
<223> OTHER INFORMATION: Xaa =  T, K, I or N
<220> FEATURE:
<221> NAME/KEY: MISC_FEATURE
<222> LOCATION: (32)..(32)
<223> OTHER INFORMATION: Xaa =  L or T
<220> FEATURE:
<221> NAME/KEY: MISC_FEATURE
<222> LOCATION: (33)..(33)
<223> OTHER INFORMATION: Xaa =  P or A
<220> FEATURE:
<221> NAME/KEY: MISC_FEATURE
<222> LOCATION: (34)..(34)
<223> OTHER INFORMATION: Xaa =  Q, L, H, R, K or P
<220> FEATURE:
<221> NAME/KEY: MISC_FEATURE
<222> LOCATION: (35)..(35)
<223> OTHER INFORMATION: Xaa =  A, T, V or P
<220> FEATURE:
<221> NAME/KEY: MISC_FEATURE
<222> LOCATION: (39)..(39)
<223> OTHER INFORMATION: Xaa =  P, S or A
<220> FEATURE:
<221> NAME/KEY: MISC_FEATURE
<222> LOCATION: (40)..(40)
<223> OTHER INFORMATION: Xaa =  S or  A
```

```
<220> FEATURE:
<221> NAME/KEY: MISC_FEATURE
<222> LOCATION: (42)..(42)
<223> OTHER INFORMATION: Xaa = G or R
<220> FEATURE:
<221> NAME/KEY: MISC_FEATURE
<222> LOCATION: (43)..(43)
<223> OTHER INFORMATION: Xaa = F or C

<400> SEQUENCE: 175

Lys Gly Gly Xaa Lys Xaa Ala Arg Xaa Ile Val Xaa Pro Xaa Leu Gly
1               5                   10                  15

Xaa Arg Val Cys Glu Lys Xaa Ala Leu Xaa Xaa Val Xaa Xaa Xaa Xaa
            20                  25                  30

Xaa Xaa Xaa Val Met Gly Xaa Xaa Tyr Xaa Xaa Gln
        35                  40

<210> SEQ ID NO 176
<211> LENGTH: 29
<212> TYPE: PRT
<213> ORGANISM: artificial sequence
<220> FEATURE:
<223> OTHER INFORMATION: anti-HCV immunogenic peptide

<400> SEQUENCE: 176

Arg Lys Pro Ala Arg Leu Ile Val Phe Pro Asp Leu Gly Val Arg Val
1               5                   10                  15

Cys Glu Lys Met Ala Leu Tyr Asp Val Val Ser Thr Leu
            20                  25

<210> SEQ ID NO 177
<211> LENGTH: 29
<212> TYPE: PRT
<213> ORGANISM: artificial sequence
<220> FEATURE:
<223> OTHER INFORMATION: anti-HCV immunogenic peptide

<400> SEQUENCE: 177

Arg Lys Pro Ala Arg Leu Ile Val Phe Pro Asp Leu Gly Val Arg Val
1               5                   10                  15

Cys Glu Lys Met Ala Leu Tyr Asp Val Val Ser Lys Leu
            20                  25

<210> SEQ ID NO 178
<211> LENGTH: 29
<212> TYPE: PRT
<213> ORGANISM: artificial sequence
<220> FEATURE:
<223> OTHER INFORMATION: anti-HCV immunogenic peptide

<400> SEQUENCE: 178

Arg Lys Pro Ala Arg Leu Ile Val Phe Pro Asp Leu Gly Val Arg Val
1               5                   10                  15

Cys Glu Lys Met Ala Leu Tyr Asp Val Val Thr Lys Leu
            20                  25

<210> SEQ ID NO 179
<211> LENGTH: 29
<212> TYPE: PRT
<213> ORGANISM: artificial sequence
<220> FEATURE:
<223> OTHER INFORMATION: anti-HCV immunogenic peptide

<400> SEQUENCE: 179

Gln Lys Pro Ala Arg Leu Ile Val Phe Pro Asp Leu Gly Val Arg Val
1               5                   10                  15
```

```
Cys Glu Lys Met Ala Leu Tyr Asp Val Val Ser Thr Leu
            20                  25
```

<210> SEQ ID NO 180
<211> LENGTH: 29
<212> TYPE: PRT
<213> ORGANISM: artificial sequence
<220> FEATURE:
<223> OTHER INFORMATION: anti-HCV immunogenic peptide

<400> SEQUENCE: 180

```
Arg Lys Ala Ala Arg Leu Ile Val Phe Pro Asp Leu Gly Val Arg Val
1               5                   10                  15

Cys Glu Lys Met Ala Leu Tyr Asp Val Val Ser Thr Leu
            20                  25
```

<210> SEQ ID NO 181
<211> LENGTH: 29
<212> TYPE: PRT
<213> ORGANISM: artificial sequence
<220> FEATURE:
<223> OTHER INFORMATION: anti-HCV immunogenic peptide

<400> SEQUENCE: 181

```
Arg Lys Pro Ala Arg Leu Ile Val Phe Pro Asp Leu Gly Val Arg Val
1               5                   10                  15

Cys Glu Lys Met Ala Leu Tyr Asp Val Val Ser Ile Leu
            20                  25
```

<210> SEQ ID NO 182
<211> LENGTH: 29
<212> TYPE: PRT
<213> ORGANISM: artificial sequence
<220> FEATURE:
<223> OTHER INFORMATION: anti-HCV immunogenic peptide

<400> SEQUENCE: 182

```
Arg Lys Pro Ala Arg Leu Ile Val Phe Pro Glu Leu Gly Val Arg Val
1               5                   10                  15

Cys Glu Lys Met Ala Leu Tyr Asp Val Val Ser Thr Leu
            20                  25
```

<210> SEQ ID NO 183
<211> LENGTH: 29
<212> TYPE: PRT
<213> ORGANISM: artificial sequence
<220> FEATURE:
<223> OTHER INFORMATION: anti-HCV immunogenic peptide

<400> SEQUENCE: 183

```
Arg Lys Pro Ala Arg Phe Ile Val Phe Pro Asp Leu Gly Val Arg Val
1               5                   10                  15

Cys Glu Lys Met Ala Leu Tyr Asp Val Val Ser Thr Leu
            20                  25
```

<210> SEQ ID NO 184
<211> LENGTH: 29
<212> TYPE: PRT
<213> ORGANISM: artificial sequence
<220> FEATURE:
<223> OTHER INFORMATION: anti-HCV immunogenic peptide

<400> SEQUENCE: 184

```
Arg Lys Ala Ala Arg Leu Ile Val Phe Pro Asp Leu Gly Val Arg Val
1               5                   10                  15
```

```
Cys Glu Lys Met Ala Leu Tyr Asn Val Val Ser Thr Leu
            20                  25

<210> SEQ ID NO 185
<211> LENGTH: 29
<212> TYPE: PRT
<213> ORGANISM: artificial sequence
<220> FEATURE:
<223> OTHER INFORMATION: anti-HCV immunogenic peptide

<400> SEQUENCE: 185

Arg Lys Pro Ala Arg Leu Ile Val Phe Pro Asp Leu Gly Val Arg Val
1               5                   10                  15

Cys Glu Lys Met Ala Leu Tyr Asp Val Val Ser Asn Leu
            20                  25

<210> SEQ ID NO 186
<211> LENGTH: 29
<212> TYPE: PRT
<213> ORGANISM: artificial sequence
<220> FEATURE:
<223> OTHER INFORMATION: anti-HCV immunogenic peptide

<400> SEQUENCE: 186

Arg Lys Pro Ala Arg Leu Ile Val Tyr Pro Asp Leu Gly Val Arg Val
1               5                   10                  15

Cys Glu Lys Met Ala Leu Tyr Asp Val Val Ser Thr Leu
            20                  25

<210> SEQ ID NO 187
<211> LENGTH: 29
<212> TYPE: PRT
<213> ORGANISM: artificial sequence
<220> FEATURE:
<223> OTHER INFORMATION: anti-HCV immunogenic peptide

<400> SEQUENCE: 187

Arg Lys Pro Ala Arg Leu Ile Val Tyr Pro Asp Leu Gly Ser Arg Val
1               5                   10                  15

Cys Glu Lys Arg Ala Leu His Asp Val Ile Lys Lys Thr
            20                  25

<210> SEQ ID NO 188
<211> LENGTH: 44
<212> TYPE: PRT
<213> ORGANISM: artificial sequence
<220> FEATURE:
<223> OTHER INFORMATION: anti-HCV immunogenic peptide

<400> SEQUENCE: 188

Lys Gly Gly Arg Lys Pro Ala Arg Leu Ile Val Phe Pro Asp Leu Gly
1               5                   10                  15

Val Arg Val Cys Glu Lys Met Ala Leu Tyr Asp Val Val Ser Thr Leu
            20                  25                  30

Pro Gln Ala Val Met Gly Pro Ser Tyr Gly Phe Gln
        35                  40

<210> SEQ ID NO 189
<211> LENGTH: 44
<212> TYPE: PRT
<213> ORGANISM: artificial sequence
<220> FEATURE:
<223> OTHER INFORMATION: anti-HCV immunogenic peptide

<400> SEQUENCE: 189
```

```
Lys Gly Gly Arg Lys Pro Ala Arg Leu Ile Val Phe Pro Asp Leu Gly
1               5                   10                  15

Val Arg Val Cys Glu Lys Met Ala Leu Tyr Asp Val Val Ser Lys Leu
            20                  25                  30

Pro Leu Ala Val Met Gly Ser Ser Tyr Gly Phe Gln
        35                  40
```

<210> SEQ ID NO 190
<211> LENGTH: 44
<212> TYPE: PRT
<213> ORGANISM: artificial sequence
<220> FEATURE:
<223> OTHER INFORMATION: anti-HCV immunogenic peptide

<400> SEQUENCE: 190

```
Lys Gly Gly Arg Lys Pro Ala Arg Leu Ile Val Phe Pro Asp Leu Gly
1               5                   10                  15

Val Arg Val Cys Glu Lys Met Ala Leu Tyr Asp Val Val Ser Lys Leu
            20                  25                  30

Pro Pro Ala Val Met Gly Ser Ser Tyr Gly Phe Gln
        35                  40
```

<210> SEQ ID NO 191
<211> LENGTH: 44
<212> TYPE: PRT
<213> ORGANISM: artificial sequence
<220> FEATURE:
<223> OTHER INFORMATION: anti-HCV immunogenic peptide

<400> SEQUENCE: 191

```
Lys Gly Gly Arg Lys Pro Ala Arg Leu Ile Val Phe Pro Asp Leu Gly
1               5                   10                  15

Val Arg Val Cys Glu Lys Met Ala Leu Tyr Asp Val Val Thr Lys Leu
            20                  25                  30

Pro Leu Ala Val Met Gly Ser Ser Tyr Gly Phe Gln
        35                  40
```

<210> SEQ ID NO 192
<211> LENGTH: 44
<212> TYPE: PRT
<213> ORGANISM: artificial sequence
<220> FEATURE:
<223> OTHER INFORMATION: anti-HCV immunogenic peptide

<400> SEQUENCE: 192

```
Lys Gly Gly Arg Lys Pro Ala Arg Leu Ile Val Phe Pro Asp Leu Gly
1               5                   10                  15

Val Arg Val Cys Glu Lys Met Ala Leu Tyr Asp Val Val Ser Thr Leu
            20                  25                  30

Pro Gln Ala Val Met Gly Ser Ser Tyr Gly Phe Gln
        35                  40
```

<210> SEQ ID NO 193
<211> LENGTH: 44
<212> TYPE: PRT
<213> ORGANISM: artificial sequence
<220> FEATURE:
<223> OTHER INFORMATION: anti-HCV immunogenic peptide

<400> SEQUENCE: 193

```
Lys Gly Gly Arg Lys Pro Ala Arg Leu Ile Val Phe Pro Asp Leu Gly
1               5                   10                  15
```

```
Val Arg Val Cys Glu Lys Met Ala Leu Tyr Asp Val Ser Thr Leu
            20                  25                  30

Pro Gln Ala Val Met Gly Ala Ser Tyr Gly Phe Gln
        35                  40

<210> SEQ ID NO 194
<211> LENGTH: 44
<212> TYPE: PRT
<213> ORGANISM: artificial sequence
<220> FEATURE:
<223> OTHER INFORMATION: anti-HCV immunogenic peptide

<400> SEQUENCE: 194

Lys Gly Gly Arg Lys Pro Ala Arg Leu Ile Val Phe Pro Asp Leu Gly
1               5                   10                  15

Val Arg Val Cys Glu Lys Met Ala Leu Tyr Asp Val Ser Thr Leu
            20                  25                  30

Pro Gln Val Val Met Gly Ser Ser Tyr Gly Phe Gln
        35                  40

<210> SEQ ID NO 195
<211> LENGTH: 44
<212> TYPE: PRT
<213> ORGANISM: artificial sequence
<220> FEATURE:
<223> OTHER INFORMATION: anti-HCV immunogenic peptide

<400> SEQUENCE: 195

Lys Gly Gly Gln Lys Pro Ala Arg Leu Ile Val Phe Pro Asp Leu Gly
1               5                   10                  15

Val Arg Val Cys Glu Lys Met Ala Leu Tyr Asp Val Ser Thr Leu
            20                  25                  30

Pro Gln Ala Val Met Gly Ser Ser Tyr Gly Phe Gln
        35                  40

<210> SEQ ID NO 196
<211> LENGTH: 44
<212> TYPE: PRT
<213> ORGANISM: artificial sequence
<220> FEATURE:
<223> OTHER INFORMATION: anti-HCV immunogenic peptide

<400> SEQUENCE: 196

Lys Gly Gly Arg Lys Ala Ala Arg Leu Ile Val Phe Pro Asp Leu Gly
1               5                   10                  15

Val Arg Val Cys Glu Lys Met Ala Leu Tyr Asp Val Ser Thr Leu
            20                  25                  30

Pro Gln Ala Val Met Gly Ser Ser Tyr Gly Phe Gln
        35                  40

<210> SEQ ID NO 197
<211> LENGTH: 44
<212> TYPE: PRT
<213> ORGANISM: artificial sequence
<220> FEATURE:
<223> OTHER INFORMATION: anti-HCV immunogenic peptide

<400> SEQUENCE: 197

Lys Gly Gly Arg Lys Pro Ala Arg Leu Ile Val Phe Pro Asp Leu Gly
1               5                   10                  15

Val Arg Val Cys Glu Lys Met Ala Leu Tyr Asp Val Ser Ile Leu
            20                  25                  30

Pro Gln Ala Val Met Gly Ser Ser Tyr Gly Phe Gln
```

<210> SEQ ID NO 198
<211> LENGTH: 44
<212> TYPE: PRT
<213> ORGANISM: artificial sequence
<220> FEATURE:
<223> OTHER INFORMATION: anti-HCV immunogenic peptide

<400> SEQUENCE: 198

Lys Gly Gly Arg Lys Pro Ala Arg Leu Ile Val Phe Pro Glu Leu Gly
1               5                   10                  15

Val Arg Val Cys Glu Lys Met Ala Leu Tyr Asp Val Val Ser Thr Leu
            20                  25                  30

Pro Gln Ala Val Met Gly Ser Ser Tyr Gly Phe Gln
        35                  40

<210> SEQ ID NO 199
<211> LENGTH: 44
<212> TYPE: PRT
<213> ORGANISM: artificial sequence
<220> FEATURE:
<223> OTHER INFORMATION: anti-HCV immunogenic peptide

<400> SEQUENCE: 199

Lys Gly Gly Arg Lys Pro Ala Arg Phe Ile Val Phe Pro Asp Leu Gly
1               5                   10                  15

Val Arg Val Cys Glu Lys Met Ala Leu Tyr Asp Val Val Ser Thr Leu
            20                  25                  30

Pro Lys Ala Val Met Gly Ser Ser Tyr Gly Phe Gln
        35                  40

<210> SEQ ID NO 200
<211> LENGTH: 44
<212> TYPE: PRT
<213> ORGANISM: artificial sequence
<220> FEATURE:
<223> OTHER INFORMATION: anti-HCV immunogenic peptide

<400> SEQUENCE: 200

Lys Gly Gly Arg Lys Pro Ala Arg Phe Ile Val Phe Pro Asp Leu Gly
1               5                   10                  15

Val Arg Val Cys Glu Lys Met Ala Leu Tyr Asp Val Val Ser Thr Leu
            20                  25                  30

Pro Gln Ala Val Met Gly Ser Ser Tyr Gly Phe Gln
        35                  40

<210> SEQ ID NO 201
<211> LENGTH: 44
<212> TYPE: PRT
<213> ORGANISM: artificial sequence
<220> FEATURE:
<223> OTHER INFORMATION: anti-HCV immunogenic peptide

<400> SEQUENCE: 201

Lys Gly Gly Arg Lys Pro Ala Arg Leu Ile Val Phe Pro Asp Leu Gly
1               5                   10                  15

Val Arg Val Cys Glu Lys Met Ala Leu Tyr Asp Val Val Ser Thr Leu
            20                  25                  30

Pro Arg Ala Val Met Gly Ser Ser Tyr Gly Cys Gln
        35                  40

<210> SEQ ID NO 202

```
<211> LENGTH: 44
<212> TYPE: PRT
<213> ORGANISM: artificial sequence
<220> FEATURE:
<223> OTHER INFORMATION: anti-HCV immunogenic peptide

<400> SEQUENCE: 202

Lys Gly Gly Arg Lys Pro Ala Arg Leu Ile Val Phe Pro Asp Leu Gly
1               5                   10                  15

Val Arg Val Cys Glu Lys Met Ala Leu Tyr Asp Val Val Ser Thr Leu
            20                  25                  30

Pro Gln Pro Val Met G

<223> OTHER INFORMATION: anti-HCV immunogenic peptide

<400> SEQUENCE: 206

Lys Gly Gly Arg Lys Ala Ala Arg Leu Ile Val Phe Pro Asp Leu Gly
1               5                   10                  15

Val Arg Val Cys Glu Lys Met Ala Leu Tyr Asp Val Val Ser Thr Leu
            20                  25                  30

Pro Gln Ala Val Met Gly Pro Ser Tyr Gly Phe Gln
        35                  40

<210> SEQ ID NO 207
<211> LENGTH: 44
<212> TYPE: PRT
<213> ORGANISM: artificial sequence
<220> FEATURE:
<223> OTHER INFORMATION: anti-HCV immunogenic peptide

<400> SEQUENCE: 207

Lys Gly Gly Arg Lys Ala Ala Arg Leu Ile Val Phe Pro Asp Leu Gly
1               5                   10                  15

Val Arg Val Cys Glu Lys Met Ala Leu Tyr Asn Val Val Ser Thr Leu
            20                  25                  30

Pro Gln Ala Val Met Gly Ser Ser Tyr Gly Phe Gln
        35                  40

<210> SEQ ID NO 208
<211> LENGTH: 44
<212> TYPE: PRT
<213> ORGANISM: artificial sequence
<220> FEATURE:
<223> OTHER INFORMATION: anti-HCV immunogenic peptide

<400> SEQUENCE: 208

Lys Gly Gly Arg Lys Pro Ala Arg Leu Ile Val Phe Pro Asp Leu Gly
1               5                   10                  15

Val Arg Val Cys Glu Lys Met Ala Leu Tyr Asp Val Val Ser Asn Leu
            20                  25                  30

Pro Gln Ala Val Met Gly Ser Ser Tyr Gly Phe Gln
        35                  40

<210> SEQ ID NO 209
<211> LENGTH: 44
<212> TYPE: PRT
<213> ORGANISM: artificial sequence
<220> FEATURE:
<223> OTHER INFORMATION: anti-HCV immunogenic peptide

<400> SEQUENCE: 209

Lys Gly Gly Arg Lys Pro Ala Arg Leu Ile Val Phe Pro Glu Leu Gly
1               5                   10                  15

Val Arg Val Cys Glu Lys Met Ala Leu Tyr Asp Val Val Ser Thr Leu
            20                  25                  30

Pro Gln Ala Val Met Gly Pro Ser Tyr Gly Phe Gln
        35                  40

<210> SEQ ID NO 210
<211> LENGTH: 44
<212> TYPE: PRT
<213> ORGANISM: artificial sequence
<220> FEATURE:
<223> OTHER INFORMATION: anti-HCV immunogenic peptide

<400> SEQUENCE: 210

-continued

```
Lys Gly Gly Arg Lys Pro Ala Arg Leu Ile Val Phe Pro Asp Leu Gly
1               5                   10                  15

Val Arg Val Cys Glu Lys Met Ala Leu Tyr Asp Val Ser Thr Leu
            20                  25                  30

Pro His Thr Val Met Gly Ser Ser Tyr Gly Phe Gln
        35                  40
```

<210> SEQ ID NO 211
<211> LENGTH: 44
<212> TYPE: PRT
<213> ORGANISM: artificial sequence
<220> FEATURE:
<223> OTHER INFORMATION: anti-HCV immunogenic peptide

<400> SEQUENCE: 211

```
Lys Gly Gly Arg Lys Pro Ala Arg Leu Ile Val Tyr Pro Asp Leu Gly
1               5                   10                  15

Val Arg Val Cys Glu Lys Met Ala Leu Tyr Asp Val Ser Thr Leu
            20                  25                  30

Pro Gln Ala Val Met Gly Ser Ser Tyr Gly Phe Gln
        35                  40
```

<210> SEQ ID NO 212
<211> LENGTH: 44
<212> TYPE: PRT
<213> ORGANISM: artificial sequence
<220> FEATURE:
<223> OTHER INFORMATION: anti-HCV immunogenic peptide

<400> SEQUENCE: 212

```
Lys Gly Gly Arg Lys Pro Ala Arg Leu Ile Val Tyr Pro Asp Leu Gly
1               5                   10                  15

Ser Arg Val Cys Glu Lys Arg Ala Leu His Asp Val Ile Lys Lys Thr
            20                  25                  30

Ala Leu Ala Val Met Gly Ala Ala Tyr Gly Phe Gln
        35                  40
```

<210> SEQ ID NO 213
<211> LENGTH: 10
<212> TYPE: PRT
<213> ORGANISM: artificial sequence
<220> FEATURE:
<223> OTHER INFORMATION: anti-HCV immunogenic peptide
<220> FEATURE:
<221> NAME/KEY: MISC_FEATURE
<222> LOCATION: (2)..(2)
<223> OTHER INFORMATION: Xaa = L or V
<220> FEATURE:
<221> NAME/KEY: MISC_FEATURE
<222> LOCATION: (3)..(3)
<223> OTHER INFORMATION: Xaa = L or F
<220> FEATURE:
<221> NAME/KEY: MISC_FEATURE
<222> LOCATION: (4)..(4)
<223> OTHER INFORMATION: Xaa = G or S
<220> FEATURE:
<221> NAME/KEY: MISC_FEATURE
<222> LOCATION: (5)..(5)
<223> OTHER INFORMATION: Xaa = C or T
<220> FEATURE:
<221> NAME/KEY: MISC_FEATURE
<222> LOCATION: (6)..(6)
<223> OTHER INFORMATION: Xaa = I or V
<220> FEATURE:
<221> NAME/KEY: MISC_FEATURE
<222> LOCATION: (7)..(7)
<223> OTHER INFORMATION: Xaa = I or V

<400> SEQUENCE: 213

```
Gly Xaa Xaa Xaa Xaa Xaa Thr Ser Leu
1               5                   10

<210> SEQ ID NO 214
<211> LENGTH: 10
<212> TYPE: PRT
<213> ORGANISM: artificial sequence
<220> FEATURE:
<223> OTHER INFORMATION: anti-HCV immunogenic peptide

<400> SEQUENCE: 214

Gly Leu Leu Gly Cys Ile Ile Thr Ser Leu
1               5                   10

<210> SEQ ID NO 215
<211> LENGTH: 10
<212> TYPE: PRT
<213> ORGANISM: artificial sequence
<220> FEATURE:
<223> OTHER INFORMATION: anti-HCV immunogenic peptide

<400> SEQUENCE: 215

Gly Leu Phe Gly Cys Ile Ile Thr Ser Leu
1               5                   10

<210> SEQ ID NO 216
<211> LENGTH: 10
<212> TYPE: PRT
<213> ORGANISM: artificial sequence
<220> FEATURE:
<223> OTHER INFORMATION: anti-HCV immunogenic peptide

<400> SEQUENCE: 216

Gly Val Leu Gly Cys Val Ile Thr Ser Leu
1               5                   10

<210> SEQ ID NO 217
<211> LENGTH: 10
<212> TYPE: PRT
<213> ORGANISM: artificial sequence
<220> FEATURE:
<223> OTHER INFORMATION: anti-HCV immunogenic peptide

<400> SEQUENCE: 217

Gly Val Leu Gly Cys Ile Ile Thr Ser Leu
1               5                   10

<210> SEQ ID NO 218
<211> LENGTH: 10
<212> TYPE: PRT
<213> ORGANISM: artificial sequence
<220> FEATURE:
<223> OTHER INFORMATION: anti-HCV immunogenic peptide

<400> SEQUENCE: 218

Gly Leu Leu Gly Cys Ile Val Thr Ser Leu
1               5                   10

<210> SEQ ID NO 219
<211> LENGTH: 10
<212> TYPE: PRT
<213> ORGANISM: artificial sequence
<220> FEATURE:
<223> OTHER INFORMATION: anti-HCV immunogenic peptide

<400> SEQUENCE: 219

Gly Leu Phe Gly Cys Ile Val Thr Ser Leu
```

```
<210> SEQ ID NO 220
<211> LENGTH: 10
<212> TYPE: PRT
<213> ORGANISM: artificial sequence
<220> FEATURE:
<223> OTHER INFORMATION: anti-HCV immunogenic peptide

<400> SEQUENCE: 220

Gly Leu Phe Ser Thr Ile Ile Thr Ser Leu
1               5                   10

<210> SEQ ID NO 221
<211> LENGTH: 9
<212> TYPE: PRT
<213> ORGANISM: artificial sequence
<220> FEATURE:
<223> OTHER INFORMATION: anti-HCV immunogenic peptide
<220> FEATURE:
<221> NAME/KEY: MISC_FEATURE
<222> LOCATION: (4)..(4)
<223> OTHER INFORMATION: Xaa = T, S or A
<220> FEATURE:
<221> NAME/KEY: MISC_FEATURE
<222> LOCATION: (5)..(5)
<223> OTHER INFORMATION: Xaa = T or I
<220> FEATURE:
<221> NAME/KEY: MISC_FEATURE
<222> LOCATION: (6)..(6)
<223> OTHER INFORMATION: Xaa = Q, S or G
<220> FEATURE:
<221> NAME/KEY: MISC_FEATURE
<222> LOCATION: (7)..(7)
<223> OTHER INFORMATION: Xaa = N, Q, H, S, Y or T

<400> SEQUENCE: 221

Ser Pro Leu Xaa Xaa Xaa Xaa Thr Leu
1               5

<210> SEQ ID NO 222
<211> LENGTH: 9
<212> TYPE: PRT
<213> ORGANISM: artificial sequence
<220> FEATURE:
<223> OTHER INFORMATION: anti-HCV immunogenic peptide

<400> SEQUENCE: 222

Ser Pro Leu Thr Thr Gln Asn Thr Leu
1               5

<210> SEQ ID NO 223
<211> LENGTH: 9
<212> TYPE: PRT
<213> ORGANISM: artificial sequence
<220> FEATURE:
<223> OTHER INFORMATION: anti-HCV immunogenic peptide

<400> SEQUENCE: 223

Ser Pro Leu Thr Thr Ser Gln Thr Leu
1               5

<210> SEQ ID NO 224
<211> LENGTH: 9
<212> TYPE: PRT
<213> ORGANISM: artificial sequence
<220> FEATURE:
<223> OTHER INFORMATION: anti-HCV immunogenic peptide

<400> SEQUENCE: 224
```

```
Ser Pro Leu Thr Thr Gly Gln Thr Leu
1               5

<210> SEQ ID NO 225
<211> LENGTH: 9
<212> TYPE: PRT
<213> ORGANISM: artificial sequence
<220> FEATURE:
<223> OTHER INFORMATION: anti-HCV immunogenic peptide

<400> SEQUENCE: 225

Ser Pro Leu Thr Thr Gln His Thr Leu
1               5

<210> SEQ ID NO 226
<211> LENGTH: 9
<212> TYPE: PRT
<213> ORGANISM: artificial sequence
<220> FEATURE:
<223> OTHER INFORMATION: anti-HCV immunogenic peptide

<400> SEQUENCE: 226

Ser Pro Leu Thr Thr Gln Ser Thr Leu
1               5

<210> SEQ ID NO 227
<211> LENGTH: 9
<212> TYPE: PRT
<213> ORGANISM: artificial sequence
<220> FEATURE:
<223> OTHER INFORMATION: anti-HCV immunogenic peptide

<400> SEQUENCE: 227

Ser Pro Leu Thr Thr Gln Tyr Thr Leu
1               5

<210> SEQ ID NO 228
<211> LENGTH: 9
<212> TYPE: PRT
<213> ORGANISM: artificial sequence
<220> FEATURE:
<223> OTHER INFORMATION: anti-HCV immunogenic peptide

<400> SEQUENCE: 228

Ser Pro Leu Thr Thr Gln Thr Thr Leu
1               5

<210> SEQ ID NO 229
<211> LENGTH: 9
<212> TYPE: PRT
<213> ORGANISM: artificial sequence
<220> FEATURE:
<223> OTHER INFORMATION: anti-HCV immunogenic peptide

<400> SEQUENCE: 229

Ser Pro Leu Thr Ile Gln His Thr Leu
1               5

<210> SEQ ID NO 230
<211> LENGTH: 9
<212> TYPE: PRT
<213> ORGANISM: artificial sequence
<220> FEATURE:
<223> OTHER INFORMATION: anti-HCV immunogenic peptide

<400> SEQUENCE: 230

Ser Pro Leu Ser Thr Gln Asn Thr Leu
1               5
```

<210> SEQ ID NO 231
<211> LENGTH: 9
<212> TYPE: PRT
<213> ORGANISM: artificial sequence
<220> FEATURE:
<223> OTHER INFORMATION: anti-HCV immunogenic peptide

<400> SEQUENCE: 231

Ser Pro Leu Ala Thr Gln Tyr Thr Leu
1               5

<210> SEQ ID NO 232
<211> LENGTH: 9
<212> TYPE: PRT
<213> ORGANISM: artificial sequence
<220> FEATURE:
<223> OTHER INFORMATION: anti-HCV immunogenic peptide

<400> SEQUENCE: 232

Ser Pro Leu Thr Thr Gln Gln Thr Leu
1               5

<210> SEQ ID NO 233
<211> LENGTH: 16
<212> TYPE: PRT
<213> ORGANISM: artificial sequence
<220> FEATURE:
<223> OTHER INFORMATION: anti-HCV immunogenic peptide

<400> SEQUENCE: 233

Arg Tyr Met Ile Leu Gly Leu Leu Ala Leu Ala Ala Val Cys Ser Ala
1               5                   10                  15

<210> SEQ ID NO 234
<211> LENGTH: 137
<212> TYPE: PRT
<213> ORGANISM: artificial sequence
<220> FEATURE:
<223> OTHER INFORMATION: anti-HCV immunogenic peptide

<400> SEQUENCE: 234

Gly Leu Leu Gly Cys Ile Ile Thr Ser Leu Thr Gly Arg Asp Lys Asn
1               5                   10                  15

Gln Val Glu Gly Glu Val Gln Ile Val Ser Thr Ala Thr Gln Thr Phe
            20                  25                  30

Leu Ala Thr Cys Ile Asn Gly Val Cys Trp Thr Val Tyr Tyr Ala Ala
        35                  40                  45

Gln Gly Tyr Lys Val Arg Val Leu Asn Pro Ser Val Ala Ala Thr Leu
    50                  55                  60

Gly Phe Gly Ala Tyr Met Ser Lys Ala His Gly Ile Ser Leu Met Ala
65                  70                  75                  80

Phe Thr Ala Ser Ile Thr Ser Pro Leu Thr Thr Gln Asn Thr Leu Leu
                85                  90                  95

Phe Asn Ile Leu Gly Gly Trp Val Ala Ala Gln Leu Arg Lys Pro Ala
            100                 105                 110

Arg Leu Ile Val Phe Pro Asp Leu Gly Val Arg Val Cys Glu Lys Met
        115                 120                 125

Ala Leu Tyr Asp Val Val Ser Thr Leu
    130                 135

<210> SEQ ID NO 235
<211> LENGTH: 417

```
<212> TYPE: DNA
<213> ORGANISM: artificial sequence
<220> FEATURE:
<223> OTHER INFORMATION: polyEp-WT coding sequence

<400> SEQUENCE: 235
atgggcctgc ttggctgtat catcactagc ctcacaggtc gggacaagaa ccaggtcgat      60
ggggaggttc aggtgctctc caccgcaacg caatctttcc tggcgacctg cgtcaatggc     120
gtgtgttgga ccgtctacta tgcagcccaa gggtacaagg tgcgcgtcct aaacccgtcc     180
gttgccgcca cattgggctt tggagcgtat atgtccaagg cacatggcat ctcactgatg     240
gcattcacag cctctatcac cagtccgctc accacccaga tacccctcct attcaacatc     300 ttaggggggat gggtggctgc tcaactccgc aagccagctc gccttatcgt attcccagac     360
ctgggggtac gtgtatgcga aagatggcc ctttacgacg tggtctccac cctttag         417

<210> SEQ ID NO 236
<211> LENGTH: 417
<212> TYPE: DNA
<213> ORGANISM: artificial sequence
<220> FEATURE:
<223> OTHER INFORMATION: polyEp-C coding sequence

<400> SEQUENCE: 236
atgggactgc tgggctgcat catcaccagc ctcaccggca gagacaagaa tcaggtggac      60
ggcgaggtgc aggtgctgag caccgccaca cagagcttcc tggccacctg cgtgaacggc     120
gtgtgctgga ccgtgtacta cgccgcccag ggctacaagg tgagagtgct gaacccccagc    180 gtggccgcta ccctgggctt cggcgcctac atgagcaagg cccacggcat cagcctcatg     240
gccttcaccg ccagcatcac aagccctctc accacccaga cacccctgct gttcaacatc     300
ctgggcggct gggtggccgc tcagctgaga aagcccgcca gactcatcgt gttccccgac     360
ctgggcgtga gagtgtgcga aagatggcc ctgtacgacg tggtgagcac cctgtga        417

<210> SEQ ID NO 237
<211> LENGTH: 465
<212> TYPE: DNA
<213> ORGANISM: artificial sequence
<220> FEATURE:
<223> OTHER INFORMATION: polyEp-E3 coding sequence

<400> SEQUENCE: 237
atgaggtaca tgattttagg cttgctcgcc cttgcggcag tctgcagcgc tggcctgctt      60
ggctgtatca tcactagcct cacaggtcgg gacaagaacc aggtcgatgg ggaggttcag     120
gtgctctcca ccgcaacgca atctttcctg gcgacctgcg tcaatggcgt gtgttggacc     180
gtctactatg cagcccaagg gtacaaggtg cgcgtcctaa acccgtccgt tgccgccaca     240
ttgggctttg gagcgtatat gtccaaggca catggcatct cactgatggc attcacagcc     300
tctatcacca gtccgctcac cacccagaat accctcctat tcaacatctt agggggatgg     360
gtggctgctc aactccgcaa gccagctcgc cttatcgtat tcccagacct ggggggtacgt    420 gtatgcgaga agatggccct ttacgacgtg gtctccaccc tttag                     465

<210> SEQ ID NO 238
<211> LENGTH: 9
<212> TYPE: PRT
<213> ORGANISM: Artificial Sequence
<220> FEATURE:
<223> OTHER INFORMATION: Synthetic Construct

<400> SEQUENCE: 238
```

```
Phe Leu Ala Thr Cys Val Asn Gly Val
1               5

<210> SEQ ID NO 239
<211> LENGTH: 9
<212> TYPE: PRT
<213> ORGANISM: Artificial Sequence
<220> FEATURE:
<223> OTHER INFORMATION: Synthetic Construct

<400> SEQUENCE: 239

Leu Leu Gly Cys Ile Ile Thr Ser Leu
1               5

<210> SEQ ID NO 240
<211> LENGTH: 9
<212> TYPE: PRT
<213> ORGANISM: Artificial Sequence
<220> FEATURE:
<223> OTHER INFORMATION: Synthetic Construct

<400> SEQUENCE: 240

Phe Leu Leu Leu Ala Asp Ala Arg Val
1               5

<210> SEQ ID NO 241
<211> LENGTH: 10
<212> TYPE: PRT
<213> ORGANISM: Artificial Sequence
<220> FEATURE:
<223> OTHER INFORMATION: Synthetic Construct

<400> SEQUENCE: 241

Ile Leu Ala Gly Tyr Ala Gly Ala Gly Val
1               5                   10

<210> SEQ ID NO 242
<211> LENGTH: 9
<212> TYPE: PRT
<213> ORGANISM: Artificial Sequence
<220> FEATURE:
<223> OTHER INFORMATION: Synthetic Construct

<400> SEQUENCE: 242

Ala Thr Leu Gly Phe Gly Ala Tyr Met
1               5

<210> SEQ ID NO 243
<211> LENGTH: 9
<212> TYPE: PRT
<213> ORGANISM: Artificial Sequence
<220> FEATURE:
<223> OTHER INFORMATION: Synthetic Construct

<400> SEQUENCE: 243

Ala Leu Tyr Asp Val Val Ser Thr Leu
1               5

<210> SEQ ID NO 244
<211> LENGTH: 9
<212> TYPE: PRT
<213> ORGANISM: Artificial Sequence
<220> FEATURE:
<223> OTHER INFORMATION: Synthetic Construct

<400> SEQUENCE: 244

Asp Leu Met Gly Tyr Ile Pro Leu Val
```

-continued

```
<210> SEQ ID NO 245
<211> LENGTH: 9
<212> TYPE: PRT
<213> ORGANISM: Artificial Sequence
<220> FEATURE:
<223> OTHER INFORMATION: Synthetic Construct

<400> SEQUENCE: 245

Cys Val Asn Gly Val Cys Trp Thr Val
1               5

<210> SEQ ID NO 246
<211> LENGTH: 10
<212> TYPE: PRT
<213> ORGANISM: Artificial Sequence
<220> FEATURE:
<223> OTHER INFORMATION: Synthetic Construct

<400> SEQUENCE: 246

Leu Leu Phe Asn Ile Leu Gly Gly Trp Val
1               5                   10

<210> SEQ ID NO 247
<211> LENGTH: 9
<212> TYPE: PRT
<213> ORGANISM: Artificial Sequence
<220> FEATURE:
<223> OTHER INFORMATION: Synthetic Construct

<400> SEQUENCE: 247

Ser Leu Met Ala Phe Thr Ala Ser Ile
1               5

<210> SEQ ID NO 248
<211> LENGTH: 10
<212> TYPE: PRT
<213> ORGANISM: Artificial Sequence
<220> FEATURE:
<223> OTHER INFORMATION: Synthetic Construct

<400> SEQUENCE: 248

Arg Leu Ile Val Phe Pro Asp Leu Gly Val
1               5                   10
```

PEPTIDE COMPOSITIONS AND THEIR USE IN PARTICULAR IN THE PREPARATION OF PHARMACEUTICAL COMPOSITIONS ACTIVE AGAINST THE HEPATITIS C VIRUS

CROSS-REFERENCE TO RELATED APPLICATIONS

This application is a continuation of, and claims priority from U.S. Ser. No. 11/503,245, filed Aug. 11, 2006, now abandoned which is a continuation-in-part of U.S. Ser. No. 10/514,762, filed Nov. 16, 2004 (now U.S. Pat. No. 7,393, 831), which claims priority under 35 U.S.C. 371 from PCT/FR03/001478, filed May 15, 2003, which claims priority from French application no. 02/06111, filed May 17, 2002. The contents of each of the prior applications are incorporated herein by reference.

A subject of the present invention is novel peptide compositions and their use in particular in the preparation of pharmaceutical compositions active against the hepatitis C virus.

A subject of the present invention is a peptide composition useful in particular in prophylactic and therapeutic vaccination directed against the hepatitis C virus.

Hepatitis C is the main cause of hepatitis acquired by transfusion. Hepatitis C can also be transmitted by other percutaneous routes, for example by injection of drugs by intravenous route. The risk of contamination to health professionals is moreover not negligible.

Hepatitis C differs from the other forms of liver diseases associated with viruses, such as hepatitis A, B or D. Infections by the hepatitis C virus (HCV) are mostly chronic, resulting in liver diseases, such as hepatitis, cirrhosis and carcinoma in a large number of cases (5 to 20%).

Although the risk of transmission of the virus by transfusion has diminished due to the establishment of screening tests in the 1990s, the frequency of hepatitis C remains high. By way of example, a recent study indicates that today there are still 10,000 to 15,000 new cases of infection per year in France (S. Deuffic et al., Hepatology 1999; 29: 1596-1601). At present, approximately 170 million people world-wide are chronically infected by HCV. Populations at high risk are chiefly hospital staff and intravenous-drug users, but asymptomatic blood donors exist who do not belong to these high-risk groups and in whom circulating anti-HCV antibodies have been found. For the latter, the infection route has not yet been identified.

HCV was the first hepatotropic virus isolated by means of molecular biology techniques. The sequences of the viral genome were cloned before the viral particle was visualized.

HCV belongs to a novel group of the Flaviviridae family, the hepaciviruses. This is a virus with a single positive RNA strand, of 9.5 kb, which is replicated by a copy of complementary RNA and the translation product of which is a precursor of a single polyprotein of approximately 3,000 amino acids. The 5' end of the HCV genome corresponds to a non-translated region adjacent to the genes which code for the structural proteins, the core protein of the nucleocapsid, the two envelope glycoproteins, E1 and E2, and a small protein called p7. The non-translated 5' region and the core gene are relatively well preserved in the different genotypes. The envelope proteins E1 and E2 are encoded by more variable regions from one isolate to another. The protein p7 is an extremely hydrophobic protein the function of which is not known. The 3' end of the HCV genome contains the genes which code for the non-structural proteins (NS2, NS3, NS4, NS5) and for a non-coding 3' region possessing a well-preserved domain (Major M E, Feinstone S M, Hepatology, June 1997, 25(6): 1527-1538).

Therapy for the treatment of hepatitis C which is the current focus of attention is a dual therapy using pegylated interferon and ribavirin (Maims M P et al., The Lancet, 22 Sep. 2001, Vol. 358, 958-965). Whilst this therapy is particularly effective in the case of patients infected by viral strains belonging to genotypes 2 and 3, it only has a limited effect on genotypes 1a, 1b and 4 (Manns M P, above).

It is therefore necessary to develop a vaccine composition targeting these poorly-responsive genotypes as a priority.

Several studies today show that the control of an infection caused by HCV, either naturally ("spontaneous resolution"), or after treatment ("therapeutic resolution") is associated with the induction or potentialization of cell-mediated immune responses involving the T-CD4$^+$ and T-CD8$^+$ lymphocytes (CERNY A et al., J. Clin. Invest., 95: 521-530 (1995)).

The object of vaccines based on the use of peptides is generally to induce immune responses mediated by the T-CD4+ and/or T-CD8+ lymphocytes.

The molecules of the major histocompatibility complex (MHC) are described as class I or class II. Class I molecules are expressed on virtually all of the nucleated cells and can be the target of CD8$^+$ cytotoxic T lymphocytes (CTLs). The CTLs recognize the peptides or epitopes which are presented in association with the MHC molecules of class I.

For example, the class I molecule HLA-A2.1 indicates that the binding site of the peptide is created by bringing together the domains $\alpha_1$ and $\alpha_2$ of the heavy chain of class I (Bjorkman et al., Nature, 329: 506 (1987)).

Certain authors have concluded the immunogenic power of peptide preparations on the basis of their good binding scores on HLA molecules, as in the Patent Application WO01/21189.

Such a deduction is not evident and can lead:
either to the selection of peptides having no immunogenic power, although having a high binding score, as demonstrated by the Applicant in Example 1 of the present Application with the FLAT peptide,
or to the elimination of peptides which are in fact very immunogenic, as shown with the CIN peptide in Brinster C. et al. (Hepatology, Vol. 34, N°6, 2001, 1206-1217). In fact, although the CIN peptide has an average, or even low (335), binding score, it is nevertheless capable of inducing a strong response mediated by cytotoxic T lymphocytes.

The Applicant has now unexpectedly found that a novel peptide composition containing at least two peptides chosen from the A to D peptides had a strong immunogenic power and had an effect on the ability of the cells originating from patients infected by viral strains of genotype 1a, 1b and 4 to induce specific immune responses. These patients preferably, but not limitatively, have an HLA of type HLA-A2.1.

Thus, a subject of the present invention is the peptide compositions comprising at least two compounds chosen from:
an A peptide having at least the following amino acid sequence SEQ ID NO: 1: $X_1AX_2QGYKVX_3VLNPSVX_4ATLX_5FGX_6YM\ SKAX_7GX_8$,
in which $X_1$ is Y or H, $X_2$ is A, G or T, $X_3$ is R or L, $X_4$ is A or T, $X_5$ is G or S, $X_6$ is A, T or V, $X_7$ is H or Y and $X_8$ is I, T, M or V,
a B peptide having at least the following amino acid sequence SEQ ID NO: 45: $GX_{18}X_{19}X_{20}X_{21}X_{22}X_{23}TSLTGRDX_{24}NX_{25}X_{26}X_{27}$ $GEX_{28}QX_{29}X_{30}STAX_{31}X_{32}X_{33}FLX_{34}$
$X_{35}X_{36}X_{37}NGX_{38}X_{39}WTVX_{40}$ in which $X_{18}$ is L or V, $X_{19}$ is L or F, $X_{20}$ is G or S, $X_{21}$ is C or T, $X_{22}$ is I or V, $X_{23}$ is I or V, $X_{24}$ is K, R or T, $X_{25}$ is Q or E, $X_{26}$ is V or N, $X_{27}$ is D, E or C, $X_{28}$ is V or A, $X_{29}$ is V, I, E or M, $X_{30}$ is L or V, $X_{31}$ is T, K or A, $X_{32}$ is Q or H, $X_{33}$ is S or T, $X_{34}$ is A or G, $X_{35}$ is T or S, $X_{36}$ is C or A, $X_{37}$ is V, I or T, $X_{38}$ is V or A, $X_{39}$ is C or M and $X_{40}$ is Y or F, a C peptide having at least the following amino acid sequence SEQ ID NO: 127: $SX_{47}M$ $X_{48}FTX_{49}X_{50}X_{51}TSPLX_{52}X_{53}X_{54}X_{55}TLX_{56}$ $FNIX_{57}GGWVAX_{58}QX_{59}$ in which $X_{47}$ is L or P, $X_{48}$ is A or S, $X_{49}$ is A or S, $X_{50}$ is A or S, $X_{51}$ is I or V, $X_{52}$ is T, S or A, $X_{53}$ is T or I, $X_{54}$ is Q, S or G, $X_{55}$ is N, Q, H, S, Y or T, $X_{56}$ is L or M, $X_{57}$ is L or W, $X_{58}$ is A or S and $X_{59}$ is L, P or I, and a D peptide having at least the following amino acid sequence SEQ ID NO: 174: $X_{69}KCX_{70}ARX_{71}IVX_{72}PX_{73}LGX_{74}RVCEKX_{75}$ $ALX_{76}X_{77}VX_{78}X_{79}X_{80}X_{81}$ in which $X_{69}$ is R or Q, $X_{70}$ is P or A, $X_{71}$ is L or F, $X_{72}$ is F or Y, $X_{73}$ is D or E, $X_{74}$ is V or S, $X_{75}$ is M or R, $X_{76}$ is Y or H, $X_{77}$ is D or N, $X_{78}$ is V or I, $X_{79}$ is 5, T or K, $X_{80}$ is T, K, I or N and $X_{81}$ is L or T, a B' epitope having the following sequence SEQ ID NO: 213: $GX_{18}X_{19}X_{20}X_{21}X_{22}X_{23}TSL$ in which $X_{18}$ is L or V, $X_{19}$ is L or F, $X_{20}$ is G or S, $X_{21}$ is C or T, $X_{22}$ is I or V and $X_{23}$ is I or V, and a C' epitope having the following sequence SEQ ID NO: 221: $SPLX_{52}X_{53}X_{54}X_{55}TL$ in which $X_{52}$ is T, S or A, $X_{53}$ is T or I, $X_{54}$ is Q, S or G and $X_{55}$ is N, Q, H, S, Y or T, as well as the pharmaceutical compositions containing them and their use, in particular as vaccine, for the preparation of a medicament intended for the inhibition or prevention of an infection caused by the hepatitis C virus, and as a diagnostic composition.

A particular subject of the invention is a peptide composition as defined above, characterized in that it comprises at least two peptides chosen from the A, B, C, D peptides.

A subject is also the particular A, B, C, D peptides, the nucleotide sequences coding for said peptides and the microorganisms or host cells cotransformed by these vectors.

Finally a subject is the antibodies directed against the compositions of the invention and a process for detection and/or quantification of the hepatitis C virus in a biological sample using said antibodies.

The peptide compositions of the invention, having a strong immunogenic power against the genotypes 1a, 1b and 4 of the hepatitis C virus, therefore contain at least two peptides chosen from the A to D peptides as defined above.

The A peptide is included in the non-structural protein 3 (NS3) between positions 1244 and 1274 of the polyprotein encoded by the HCV virus.

The B peptide is also included in the protein NS3 between positions 1038 and 1082 of the viral polyprotein.

The C peptide is included in the non-structural protein NS4 between positions 1789 and 1821 of said viral polyprotein.

As for the D peptide, it is included in the non-structural protein NS5b between positions 2573 and 2601 of said viral polyprotein.

Of course, by peptide is meant the peptide as such, as well as its homologues having at least 60%, preferably at least 70%, still more preferably at least 80%, better at least 90% and still better 95% homology with the peptide of interest.

The A to D peptides were obtained from the strain HCV-JA (Kato L., et al., (1990), Proc. Natl. Acad. Sci. USA, 87(24), 9524-9528) otherwise called the Shimotohno strain. They contain known epitopes but, as indicated previously, these epitopes do not necessarily have a high binding score.

The binding score is obtained by prediction, using software, of the ability of known or potential epitope sequences (peptide sequences) to bind to the HLA molecule of interest. This score can be included in a range from negative values to the value of approximately 1000 and by high binding score is meant a binding score greater than or equal to 600.

On the other hand, unexpectedly, the combination of the A to D peptides of the invention makes it possible to induce specific cytotoxic T lymphocytes capable of a vigour and effectiveness greater than that obtained with each of the peptides used separately and/or each of the individual epitopes contained in these peptides used alone or in combination as well as stimulating a higher production of γ-interferon.

Moreover, these peptides are capable of inducing specific T lymphocytes having cross-reactivity.

According to one embodiment of the invention, the compositions of the invention contain two peptides according to the following combinations: A and B peptides, A and C peptides, A and D peptides, B and C peptides, B and D peptides and C and D peptides.

The preferred compositions contain the A and B, A and C, B and D, and C and D peptides, the compositions containing the A and B, C and D, and B and D peptides being more preferred.

According to another embodiment, the compositions of the invention contain three peptides according to the following combinations: A, B and D peptides, A, C and D peptides, and B, C and D peptides, the compositions comprising the A, B and C, A, C and D, and B, C and D peptides being particularly preferred.

According to yet another embodiment, the compositions of the invention contain the four A, B, C, D peptides.

The A peptide in the compositions of the invention has at least the amino acid sequence SEQ ID NO: 1 as described above.

According to one embodiment of the invention, the A peptide has at most the 46 amino acids as described in the following sequence SEQ ID NO: 2: $SX_9X_{10}VPX_{11}X_{12}X_1AX_2QGYKVX_3VLNPSVX_4ATLX_5$ $FGX_6YMSKAX_7GX_8X_{13}PX_{14}X_{15}X_{16}X_{17}GV$, in which $X_1$ to $X_8$ are as defined previously, and $X_9$ is T or N, $X_{10}$ is K or R, $X_{11}$ is A or V, $X_{12}$ is A or E, $X_{13}$ is E or D, $X_{14}$ is N or S, $X_{15}$ is I, L or V, $X_{16}$ is R or S and $X_{17}$ is T or S.

In this case, the A peptide is situated between positions 1237 and 1282 of the viral polyprotein.

According to yet another embodiment, the A peptide is chosen from the following peptides:

the peptides having at least sequence SEQ ID NO: 3, which corresponds to sequence SEQ ID NO: 1 in which $X_1$ is Y, $X_2$ is A, $X_3$ is R, $X_4$ is A, $X_5$ is G, $X_6$ is A, $X_7$ is H and $X_8$ is I, and at most sequence SEQ ID NO: 19 which corresponds to sequence SEQ ID NO: 2 in which $X_1$ to $X_8$ are as defined for sequence SEQ ID NO: 3 and $X_9$ is T, $X_{10}$ is K, $X_{11}$ is A, $X_{12}$ is A, $X_{13}$ is E, $X_{14}$ is N, $X_{15}$ is I, $X_{16}$ is R and $X_{17}$ is T, the peptides having at least sequence SEQ ID NO: 4 which corresponds to sequence SEQ ID NO: 1 in which $X_1$ is Y, $X_2$ is A, $X_3$ is L, $X_4$ is A, $X_5$ is G, $X_6$ is A, $X_7$ is H and $X_8$ is I, and at most a sequence chosen from the following sequences:

i) sequence SEQ ID NO: 20 which corresponds to sequence SEQ ID NO: 2 in which $X_1$ to $X_8$ are as defined for sequence SEQ ID NO: 4 and $X_9$ is T, $X_{10}$ is K, $X_{11}$ is A, $X_{12}$ is A, $X_{13}$ is D, $X_{14}$ is N, $X_{15}$ is I, $X_{16}$ is R and $X_{17}$ is T, ii) sequence SEQ ID NO: 24 which corresponds to sequence SEQ ID NO: 2 in which $X_1$ to $X_8$ are as defined for sequence SEQ ID NO: 4 and $X_9$ is T, $X_{10}$ is K, $X_{11}$ is A, $X_{12}$ is A, $X_{13}$ is E, $X_{14}$ is N, $X_{15}$ is I, $X_{16}$ is R and $X_{17}$ is T, iii) sequence SEQ ID NO: 32 which corresponds to sequence SEQ ID NO: 2 in which $X_1$ to $X_8$ are as defined for sequence SEQ ID NO: 4 and $X_9$ is T, $X_{10}$ is R, $X_{11}$ is A, $X_{12}$ is A, $X_{13}$ is D, $X_{14}$ is N, $X_{15}$ is L, $X_{16}$ is R and $X_{17}$ is T, and iv) sequence SEQ ID NO: 34 which corresponds to sequence SEQ ID NO: 2 in which $X_1$ to $X_8$ are as defined for sequence SEQ ID NO: 4 and $X_9$ is T, $X_{10}$ is K, $X_{11}$ is A, $X_{12}$ is A, $X_{13}$ is D, $X_{14}$ is N, $X_{15}$ is V, $X_{16}$ is R and $X_{17}$ is T, the peptides having at least sequence SEQ ID NO: 5 which corresponds to sequence SEQ ID NO: 1 in which $X_1$ is Y, $X_2$ is A, $X_3$ is L, $X_4$ is A, $X_5$ is G, $X_6$ is A, $X_7$ is H and $X_8$ is V, and at most a sequence chosen from the following sequences:

i) sequence SEQ ID NO: 21 which corresponds to sequence SEQ ID NO: 2 in which $X_1$ to $X_8$ are as defined for sequence SEQ ID NO: 5 and $X_9$ is T, $X_{10}$ is K, $X_{11}$ is A, $X_{12}$ is A, $X_{13}$ is D, $X_{14}$ is N, $X_{15}$ is I, $X_{16}$ is R and $X_{17}$ is T, ii) sequence SEQ ID NO: 28 which corresponds to sequence SEQ ID NO: 2 in which $X_1$ to $X_8$ are as defined for sequence SEQ ID NO: 5 and $X_9$ is N, $X_{10}$ is K, $X_{11}$ is V, $X_{12}$ is E, $X_{13}$ is D, $X_{14}$ is N, $X_{15}$ is I, $X_{16}$ is R and $X_{17}$ is T, and iii) sequence SEQ ID NO: 36 which corresponds to sequence SEQ ID NO: 2 in which $X_1$ to $X_8$ are as defined for sequence SEQ ID NO: 5 and $X_9$ is T, $X_{10}$ is K, $X_{11}$ is A, $X_{12}$ is A, $X_{13}$ is D, $X_{14}$ is N, $X_{15}$ is I, $X_{16}$ is S and $X_{17}$ is T, the peptides having at least sequence SEQ ID NO: 6 which corresponds to sequence SEQ ID NO: 1 in which $X_1$ is Y, $X_2$ is A, $X_3$ is L, $X_4$ is A, $X_5$ is G, $X_6$ is A, $X_7$ is H and $X_8$ is T, and at most a sequence chosen from the following sequences:

i) sequence SEQ ID NO: 22 which corresponds to sequence SEQ ID NO: 2 in which $X_1$ to $X_8$ are as defined for sequence SEQ ID NO: 6 and $X_9$ is T, $X_{10}$ is K, $X_{11}$ is A, $X_{12}$ is A, $X_{13}$ is D, $X_{14}$ is N, $X_{15}$ is I, $X_{16}$ is R and $X_{17}$ is T, ii) sequence SEQ ID NO: 27 which corresponds to sequence SEQ ID NO: 2 in which $X_1$ to $X_8$ are as defined for sequence SEQ ID NO: 6 and $X_9$ is T, $X_{10}$ is K, $X_{11}$ is A, $X_{12}$ is A, $X_{13}$ is E, $X_{14}$ is N, $X_{15}$ is I, $X_{16}$ is R and $X_{17}$ is T, and iii) sequence SEQ ID NO: 41 which corresponds to sequence SEQ ID NO: 2 in which $X_1$ to $X_8$ are as defined for sequence SEQ ID NO: 6 and $X_9$ is T, $X_{10}$ is R, $X_{11}$ is A, $X_{12}$ is A, $X_{13}$ is D, $X_{14}$ is N, $X_{15}$ is I, $X_{16}$ is R and $X_{17}$ is T, the peptides having at least sequence SEQ ID NO: 7 which corresponds to sequence SEQ ID NO: 1 in which $X_1$ is Y, $X_2$ is A, $X_3$ is L, $X_4$ is A, $X_5$ is G, $X_6$ is A, $X_7$ is Y and $X_8$ is T, and at most a sequence chosen from the following sequences:

i) sequence SEQ ID NO: 23 which corresponds to sequence SEQ ID NO: 2 in which $X_1$ to $X_8$ are as defined for sequence SEQ ID NO: 7 and $X_9$ is T, $X_{10}$ is K, $X_{11}$ is A, $X_{12}$ is A, $X_{13}$ is D, $X_{14}$ is N, $X_{15}$ is I, $X_{16}$ is R and $X_{17}$ is T, and ii) sequence SEQ ID NO: 37 which corresponds to sequence SEQ ID NO: 2 in which $X_1$ to $X_8$ are as defined for sequence SEQ ID NO: 7 and $X_9$ is T, $X_{10}$ is K, $X_{11}$ is A, $X_{12}$ is A, $X_{13}$ is D, $X_{14}$ is N, $X_{15}$ is V, $X_{16}$ is R and $X_{17}$ is T, the peptides having at least sequence SEQ ID NO: 8 which corresponds to sequence SEQ ID NO: 1 in which $X_1$ is Y, $X_2$ is A, $X_3$ is L, $X_4$ is A, $X_5$ is S, $X_6$ is A, $X_7$ is H and $X_8$ is T, and at most sequence SEQ ID NO: 25 which corresponds to sequence SEQ ID NO: 2 in which $X_1$ to $X_8$ are as defined for sequence SEQ ID NO: 8 and $X_9$ is T, $X_{10}$ is K, $X_{11}$ is A, $X_{12}$ is A, $X_{13}$ is D, $X_{14}$ is N, $X_{15}$ is I, $X_{16}$ is R and $X_{17}$ is T, the peptides having at least sequence SEQ ID NO: 9 which corresponds to sequence SEQ ID NO: 1 in which $X_1$ is Y, $X_2$ is A, $X_3$ is L, $X_4$ is A, $X_5$ is G, $X_6$ is A, $X_7$ is Y and $X_8$ is I, and at most sequence SEQ ID NO: 26 which corresponds to sequence SEQ ID NO: 2 in which $X_1$ to $X_8$ are as defined for sequence SEQ ID NO: 9 and $X_9$ is T, $X_{10}$ is K, $X_{11}$ is A, $X_{12}$ is A, $X_{13}$ is D, $X_{14}$ is N, $X_{15}$ is V, $X_{16}$ is R and $X_{17}$ is T, the peptides having at least sequence SEQ ID NO: 10 which corresponds to sequence SEQ ID NO: 1 in which $X_1$ is Y, $X_2$ is A, $X_3$ is L, $X_4$ is T, $X_5$ is G, $X_6$ is A, $X_7$ is H and $X_8$ is V, and at most sequence SEQ ID NO: 29 which corresponds to sequence SEQ ID NO: 2 in which $X_1$ to $X_8$ are as defined for sequence SEQ ID NO: 10 and $X_9$ is T, $X_{10}$ is K, $X_{11}$ is A, $X_{12}$ is A, $X_{13}$ is D, $X_{14}$ is N, $X_{15}$ is I, $X_{16}$ is R and $X_{17}$ is T, the peptides having at least sequence SEQ ID NO: 11 which corresponds to sequence SEQ ID NO: 1 in which $X_1$ is Y, $X_2$ is G, $X_3$ is L, $X_4$ is A, $X_5$ is G, $X_6$ is A, $X_7$ is H and $X_8$ is I, and at most sequence SEQ ID NO: 30 which corresponds to sequence SEQ ID NO: 2 in which $X_1$ to $X_8$ are as defined for sequence SEQ ID NO: 11 and $X_9$ is T, $X_{10}$ is K, $X_{11}$ is A, $X_{12}$ is A, $X_{13}$ is D, $X_{14}$ is N, $X_{15}$ is I, $X_{16}$ is R and $X_{17}$ is T, the peptides having at least sequence SEQ ID NO: 12 which corresponds to sequence SEQ ID NO: 1 in which $X_1$ is Y, $X_2$ is A, $X_3$ is L, $X_4$ is A, $X_5$ is S, $X_6$ is A, $X_7$ is H and $X_8$ is I, and at most sequence SEQ ID NO: 31 which corresponds to sequence SEQ ID NO: 2 in which $X_1$ to $X_8$ are as defined for sequence SEQ ID NO: 12 and $X_9$ is T, $X_{10}$ is K, $X_{11}$ is A, $X_{12}$ is A, $X_{13}$ is D, $X_{14}$ is N, $X_{15}$ is I, $X_{16}$ is R and $X_{17}$ is T, the peptides having at least sequence SEQ ID NO: 13 which corresponds to sequence SEQ ID NO: 1 in which $X_1$ is Y, $X_2$ is T, $X_3$ is L, $X_4$ is A, $X_5$ is G, $X_6$ is A, $X_7$ is H and $X_8$ is T, and at most sequence SEQ ID NO: 33 which corresponds to sequence SEQ ID NO: 2 in which $X_1$ to $X_8$ are as defined for sequence SEQ ID NO: 13 and $X_9$ is T, $X_{10}$ is K, $X_{11}$ is A, $X_{12}$ is A, $X_{13}$ is D, $X_{14}$ is N, $X_{15}$ is I, $X_{16}$ is R and $X_{17}$ is T, the peptides having at least sequence SEQ ID NO: 14 which corresponds to sequence SEQ ID NO: 1 in which $X_1$ is Y, $X_2$ is A, $X_3$ is L, $X_4$ is A, $X_5$ is S, $X_6$ is A, $X_7$ is H and $X_8$ is V, and at most a sequence chosen from the following sequences:

i) sequence SEQ ID NO: 35 which corresponds to sequence SEQ ID NO: 2 in which $X_1$ to $X_8$ are as defined for sequence SEQ ID NO: 14 and $X_9$ is T, $X_{10}$ is K, $X_{11}$ is A, $X_{12}$ is A, $X_{13}$ is D, $X_{14}$ is S, $X_{15}$ is I, $X_{16}$ is R and $X_{17}$ is T, and ii) sequence SEQ ID NO: 39 which corresponds to sequence SEQ ID NO: 2 in which $X_1$ to $X_8$ are as defined for sequence SEQ ID NO: 14 and $X_9$ is T, $X_{10}$ is K, $X_{11}$ is A, $X_{12}$ is A, $X_{13}$ is D, $X_{14}$ is N, $X_{15}$ is I, $X_{16}$ is R and $X_{17}$ is T, the peptides having at least sequence SEQ ID NO: 15 which corresponds to sequence SEQ ID NO: 1 in which $X_1$ is Y, $X_2$ is T, $X_3$ is L, $X_4$ is A, $X_5$ is S, $X_6$ is A, $X_7$ is Y and $X_8$ is M, and at most sequence SEQ ID NO: 38 which corresponds to sequence SEQ ID NO: 2 in which $X_1$ to $X_8$ are as defined for sequence SEQ ID NO: 15 and $X_9$ is T, $X_{10}$ is K, $X_{11}$ is A, $X_{12}$ is A, $X_{13}$ is D, $X_{14}$ is N, $X_{15}$ is L, $X_{16}$ is R and $X_{17}$ is T, the peptides having at least sequence SEQ ID NO: 16 which corresponds to sequence SEQ ID NO: 1 in which $X_1$ is Y, $X_2$ is A, $X_3$ is L, $X_4$ is A, $X_5$ is S, $X_6$ is A, $X_7$ is Y and $X_8$ is V, and at most a sequence chosen from the following sequences:

i) sequence SEQ ID NO: 40 which corresponds to sequence SEQ ID NO: 2 in which $X_1$ to $X_8$ are as defined for sequence SEQ ID NO: 16 and $X_9$ is T, $X_{10}$ is K, $X_1$, is A, $X_{12}$ is A, $X_{13}$ is D, $X_{14}$ is N, $X_{15}$ is I, $X_{16}$ is R and $X_{17}$ is T, and ii) sequence SEQ ID NO: 42 which corresponds to sequence SEQ ID NO: 2 in which $X_1$ to $X_8$ are as defined for sequence SEQ ID NO: 16 and $X_9$ is T, $X_{10}$ is R, $X_{11}$ is A, $X_{12}$ is A, $X_{13}$ is D, $X_{14}$ is N, $X_{15}$ is I, $X_{16}$ is R and $X_{17}$ is T, the peptides having at least sequence SEQ ID NO: 17 which corresponds to sequence SEQ ID NO: 1 in which $X_1$ is Y, $X_2$ is A, $X_3$ is L, $X_4$ is A, $X_5$ is G, $X_6$ is T, $X_7$ is Y and $X_8$ is T, and at most sequence SEQ ID NO: 43 which corresponds to sequence SEQ ID NO: 2 in which $X_1$ to $X_8$ are as defined for sequence SEQ ID NO: 17 and $X_9$ is T, $X_{10}$ is R, $X_{11}$ is A, $X_{12}$ is A, $X_{13}$ is D, $X_{14}$ is N, $X_{15}$ is I, $X_{16}$ is R and $X_{17}$ is T, and the peptides having at least sequence SEQ ID NO: 18 which corresponds to sequence SEQ ID NO: 1 in which $X_1$ is H, $X_2$ is A, $X_3$ is L, $X_4$ is A, $X_5$ is G, $X_6$ is V, $X_7$ is Y and $X_8$ is I, and at most sequence SEQ ID NO: 44 which corresponds to sequence SEQ ID NO: 2 in which $X_1$ to $X_8$ are as defined for sequence SEQ ID NO: 18 and $X_9$ is T, $X_{10}$ is K, $X_{11}$ is A, $X_{12}$ is A, $X_{13}$ is D, $X_{14}$ is N, $X_{15}$ is I, $X_{16}$ is R and $X_{17}$ is S.

Preferably, the A peptide is chosen from the peptides of sequences SEQ ID NO: 3 to 18, the peptide of sequence SEQ ID NO: 3 being particularly preferred.

The B peptide in the compositions of the invention has at least the amino acid sequence SEQ ID NO: 45 as described above.

According to one embodiment, the B peptide has at most the 63 amino acids as described in the following sequence SEQ ID NO: 46: $AX_{41}ITX_{42}YX_{43}X_{44}QTRGX_{18}X_{19}X_{20}X_{21}X_{22}X_{23}TSLTGRDX_{24}NX_{25}X_{26}X_{27}GEX_{28}QX_{29}X_{30}STAX_{31}X_{32}X_{33}FLX_{34}X_{35}X_{36}X_{37}NGX_{38}X_{39}WTVX_{40}HGAGX_{45}X_{46}X_{47}$ in which $X_{18}$ to $X_{40}$ are as defined above and $X_{41}$ is P, S or H, $X_{42}$ is A or T, $X_{43}$ is S, A, T or C, $X_{44}$ is Q or R, $X_{45}$ is S, T or A, $X_{46}$ is K or R and $X_{47}$ is T or I.

In this case, the B peptide is situated between positions 1027 and 1089 of the viral polyprotein.

According to yet another embodiment the B peptide is chosen from the following peptides:

the peptides having at least sequence SEQ ID NO: 47 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is D, $X_{28}$ is V, $X_{29}$ is V, $X_{30}$ is L, $X_{31}$ is T, $X_{32}$ is Q, $X_{33}$ is S, $X_{34}$ is A, $X_{35}$ is T, $X_{36}$ is C, $X_{37}$ is V, $X_{38}$ is V, $X_{39}$ is C and $X_{40}$ is Y, and at most sequence SEQ ID NO: 81 which corresponds to sequence SEQ ID NO: 46 in which $X_{18}$ to $X_{40}$ are as defined for sequence SEQ ID NO: 47 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 48 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is I, $X_{30}$ is V, $X_{31}$ is A, $X_{32}$ is Q, $X_{33}$ is T, $X_{34}$ is A, $X_{35}$ is T, $X_{36}$ is C, $X_{37}$ is I, $X_{38}$ is V, $X_{39}$ is C and $X_{40}$ is Y, and at most sequence SEQ ID NO: 82 which corresponds to sequence SEQ ID NO: 46 in which $X_{18}$ to $X_{40}$ are as defined for sequence SEQ ID NO: 48 and $X_{41}$ is P, $X_{42}$ is A, $X_{43}$ is A, $X_{44}$ is Q, $X_{45}$ is T, $X_{46}$ is R and $X_{47}$ is T, the peptides having at least sequence SEQ ID NO: 49 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is I, $X_{30}$ is V, $X_{31}$ is T, $X_{32}$ is Q, $X_{33}$ is T, $X_{34}$ is A, $X_{35}$ is T, $X_{36}$ is C, $X_{37}$ is I, $X_{38}$ is V, $X_{39}$ is C and $X_{40}$ is Y, and at most sequence SEQ ID NO: 83 which corresponds to sequence SEQ ID NO: 46 in which $X_{18}$ to $X_{40}$ are as defined for sequence SEQ ID NO: 49 and $X_{41}$ is P, $X_{42}$ is A, $X_{43}$ is T, $X_{44}$ is Q, $X_{45}$ is T, $X_{46}$ is R and $X_{47}$ is T, the peptides having at least sequence SEQ ID NO: 50 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is V, $X_{39}$ is C and $X_{40}$ is Y, and at most a sequence chosen from the following sequences:

i) sequence SEQ ID NO: 84 which corresponds to sequence SEQ ID NO: 46 in which $X_{18}$ to $X_{40}$ are as defined for sequence SEQ ID NO: 50 and $X_{41}$ is P, $X_{42}$ is A, $X_{43}$ is S, $X_{44}$ is Q, $X_{45}$ is S, $X_{46}$ is K and $X_{47}$ is T, ii) sequence SEQ ID NO: 90 which corresponds to sequence SEQ ID NO: 46 in which $X_{18}$ to $X_{40}$ are as defined for sequence SEQ ID NO: 50 and $X_{41}$ is P, $X_{42}$ is A, $X_{43}$ is S, $X_{44}$ is R, $X_{45}$ is S, $X_{46}$ is K and $X_{47}$ is T, iii) sequence SEQ ID NO: 105 which corresponds to sequence SEQ ID NO: 46 in which $X_{18}$ to $X_{40}$ are as defined for sequence SEQ ID NO: 50 and $X_{41}$ is P, $X_{42}$ is A, $X_{43}$ is C, $X_{44}$ is Q, $X_{45}$ is S, $X_{46}$ is K and $X_{47}$ is T, iv) sequence SEQ ID NO: 107 which corresponds to sequence SEQ ID NO: 46 in which $X_{18}$ to $X_{40}$ are as defined for sequence SEQ ID NO: 50 and $X_{41}$ is P, $X_{42}$ is A, $X_{43}$ is S, $X_{44}$ is Q, $X_{45}$ is T, $X_{46}$ is K and $X_{47}$ is T, and v) sequence SEQ ID NO: 116 which corresponds to sequence SEQ ID NO: 46 in which $X_{18}$ to $X_{40}$ are as defined for sequence SEQ ID NO: 50 and $X_{41}$ is P, $X_{42}$ is T, $X_{43}$ is S, $X_{44}$ is Q, $X_{45}$ is T, $X_{46}$ is K and $X_{47}$ is T, the peptides having at least sequence SEQ ID NO: 51 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is R, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is V, $X_{39}$ is C and $X_{40}$ is Y, and at most a sequence chosen from the following sequences:

i) sequence SEQ ID NO: 85 which corresponds to sequence SEQ ID NO: 46 in which $X_{18}$ to $X_{40}$ are as defined for sequence SEQ ID NO: 51 and $X_{41}$ is P, $X_{42}$ is A, $X_{43}$ is S, $X_{44}$ is Q, $X_{45}$ is S, $X_{46}$ is K and $X_{47}$ is T, and ii) sequence SEQ ID NO: 124 which corresponds to sequence SEQ ID NO: 46 in which $X_{18}$ to $X_{40}$ are as defined for sequence SEQ ID NO: 51 and $X_{41}$ is P, $X_{42}$ is A, $X_{43}$ is S, $X_{44}$ is Q, $X_{45}$ is A, $X_{46}$ is K and $X_{47}$ is T, the peptides having at least sequence SEQ ID NO: 52 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is I, $X_{38}$ is V, $X_{39}$ is C and $X_{40}$ is Y, and at most a sequence chosen from the following sequences:

i) sequence SEQ ID NO: 86 which corresponds to sequence SEQ ID NO: 46 in which $X_{18}$ to $X_{40}$ are as defined for sequence SEQ ID NO: 52 and $X_{41}$ is P, $X_{42}$ is A, $X_{43}$ is S, $X_{44}$ is Q, $X_{45}$ is S, $X_{46}$ is K and $X_{47}$ is T, and ii) sequence SEQ ID NO: 120 which corresponds to sequence SEQ ID NO: 46 in which $X_{18}$ to $X_{40}$ are as defined for sequence SEQ ID NO: 52 and $X_{41}$ is P, $X_{42}$ is A, $X_{43}$ is A, $X_{44}$ is Q, $X_{45}$ is S, $X_{46}$ is K and $X_{47}$ is T, the peptides having at least sequence SEQ ID NO: 53 which corresponds to sequence SEQ ID NO: 45 in which $X_{18}$ is L, $X_{19}$ is F, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is V, $X_{39}$ is C and $X_{40}$ is Y, and at most sequence SEQ ID NO: 87 which corresponds to sequence SEQ ID NO: 46 in which $X_{18}$ to $X_{40}$ are as defined for sequence SEQ ID NO: 53 and $X_{41}$ is P, $X_{42}$ is A, $X_{43}$ is S, $X_{44}$ is Q, $X_{45}$ is $X_{46}$ is K and $X_{47}$ is T, the peptides having at least sequence SEQ ID NO: 54 which corresponds to sequence SEQ ID NO: 45 in which $X_{18}$ is V, $X_{19}$ is L, $X_{20}$ is G, $X_{21}$ is C, $X_{22}$ is V, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is I, $X_{38}$ is V, $X_{39}$ is C and $X_{40}$ is Y, and at most a sequence chosen from the following sequences:

i) sequence SEQ ID NO: 88 which corresponds to sequence SEQ ID NO: 46 in which $X_{18}$ to $X_{40}$ are as defined for sequence SEQ ID NO: 54 and $X_{41}$ is P, $X_{42}$ is A, $X_{43}$ is S, $X_{44}$ is Q, $X_{45}$ is S, $X_{46}$ is K and $X_{47}$ is T, and ii) sequence SEQ ID NO: 117 which corresponds to sequence SEQ ID NO: 46 in which $X_{18}$ to $X_{40}$ are as defined for sequence SEQ ID NO: 54 and $X_{41}$ is S, $X_{42}$ is A, $X_{43}$ is S, $X_{44}$ is Q, $X_{45}$ is S, $X_{46}$ is K and $X_{47}$ is T, the peptides having at least sequence SEQ ID NO: 55 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is A, $X_{39}$ is C and $X_{40}$ is F, and at most sequence SEQ ID NO: 89 which corresponds to sequence SEQ ID NO: 46 in which $X_{18}$ to $X_{40}$ are as defined for sequence SEQ ID NO: 55 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 56 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is I, $X_{38}$ is V, $X_{39}$ is C and $X_{40}$ is F, and at most a sequence chosen from the following sequences:

i) sequence SEQ ID NO: 91 which corresponds to sequence SEQ ID NO: 46 in which $X_{18}$ to $X_{40}$ are as defined for sequence SEQ ID NO: 56 and $X_{41}$ is P, $X_{42}$ is A, $X_{43}$ is S, $X_{44}$ is Q, $X_{45}$ is A, $X_{46}$ is K and $X_{47}$ is T, and ii) sequence SEQ ID NO: 92 which corresponds to sequence SEQ ID NO: 46 in which $X_{18}$ to $X_{40}$ are as defined for sequence SEQ ID NO: 56 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 57 which corresponds to sequence SEQ ID NO: 45 in which $X_{18}$ is V, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is I, $X_{38}$ is V, $X_{39}$ is C and $X_{40}$ is Y, and at most sequence SEQ ID NO: 93 which corresponds to sequence SEQ ID NO: 46 in which $X_{18}$ to $X_{40}$ are as defined for sequence SEQ ID NO: 57 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 58 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is V, $X_{39}$ is C and $X_{40}$ is F, and at most a sequence chosen from the following sequences:

i) sequence SEQ ID NO: 94 which corresponds to sequence SEQ ID NO: 46 in which $X_{18}$ to $X_{40}$ are as defined for sequence SEQ ID NO: 58 and $X_{41}$ is P, $X_{42}$ is A, $X_{43}$ is A, $X_{44}$ is Q, $X_{45}$ is S, $X_{46}$ is K and $X_{47}$ is T, and ii) sequence SEQ ID NO: 110 which corresponds to sequence SEQ ID NO: 46 in which $X_{18}$ to $X_{40}$ are as defined for sequence SEQ ID NO: 58 and $X_{41}$ is P, $X_{42}$ is A, $X_{43}$ is S, $X_{44}$ is Q, $X_{45}$ is T, $X_{46}$ is K and $X_{47}$ is T, the peptides having at least sequence SEQ ID NO: 59 which corresponds to sequence SEQ ID NO: 45 in which $X_{18}$ is L, $X_{19}$ is L, $X_{20}$ is G, $X_{21}$ is C, $X_{22}$ is I, $X_{23}$ is V, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is A, $X_{39}$ is C and $X_{40}$ is F, and at most sequence SEQ ID NO: 95 which corresponds to sequence SEQ ID NO: 46 in which $X_{18}$ to $X_{40}$ are as defined for sequence SEQ ID NO: 59 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 60 which corresponds to sequence SEQ ID NO: 45 in which $X_{18}$ is V, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is V, $X_{39}$ is C and $X_{40}$ is F, and at most a sequence chosen from the following sequences:

i) sequence SEQ ID NO: 96 which corresponds to sequence SEQ ID NO: 46 in which $X_{18}$ to $X_{40}$ are as defined for sequence SEQ ID NO: 60 and $X_{41}$ is P, $X_{42}$ is A, $X_{43}$ is A, $X_{44}$ is Q, $X_{45}$ is S, $X_{46}$ is K and $X_{47}$ is T, and ii) sequence SEQ ID NO: 115 which corresponds to sequence SEQ ID NO: 46 in which $X_{18}$ to $X_{40}$ are as defined for sequence SEQ ID NO: 60 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 61 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is D, $X_{28}$ is V, $X_{29}$ is V, $X_{30}$ is L, $X_{31}$ is T, $X_{32}$ is Q, $X_{33}$ is S, $X_{34}$ is A, $X_{35}$ is T, $X_{36}$ is C, $X_{37}$ is I, $X_{38}$ is V, $X_{39}$ is C and $X_{40}$ is Y, and at most sequence SEQ ID NO: 97 which corresponds to sequence SEQ ID NO: 46 in which $X_{18}$ to $X_{40}$ are as defined for sequence SEQ ID NO: 61 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 62 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is A, $X_{39}$ is C and $X_{40}$ is Y, and at most a sequence chosen from the following sequences:
  i) sequence SEQ ID NO: 98 which corresponds to sequence SEQ ID NO: 46 in which $X_{18}$ to $X_{40}$ are as defined for sequence SEQ ID NO: 62 and $X_{41}$ is P, $X_{42}$ is A, $X_{43}$ is S, $X_{44}$ is Q, $X_{45}$ is S, $X_{46}$ is K and $X_{47}$ is T, and
  ii) sequence SEQ ID NO: 109 which corresponds to sequence SEQ ID NO: 46 in which $X_{18}$ to $X_{40}$ are as defined for sequence SEQ ID NO: 62 and $X_{41}$ is P, $X_{42}$ is A, $X_{43}$ is S, $X_{44}$ is Q, $X_{45}$ is T, $X_{46}$ is K and $X_{47}$ is T, the peptides having at least sequence SEQ ID NO: 63 which corresponds to sequence SEQ ID NO: 45 in which $X_{18}$ is V, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is H, $X_{33}$ is S, $X_{34}$ is A, $X_{35}$ is T, $X_{36}$ is C, $X_{37}$ is I, $X_{38}$ is V, $X_{39}$ is C and $X_{40}$ is Y, and at most sequence SEQ ID NO: 99 which corresponds to sequence SEQ ID NO: 46 in which $X_{18}$ to $X_{40}$ are as defined for sequence SEQ ID NO: 63 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 64 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is I, $X_{38}$ is A, $X_{39}$ is C and $X_{40}$ is Y, and at most sequence SEQ ID NO: 100 which corresponds to sequence SEQ ID NO: 46 in which $X_{18}$ to $X_{40}$ are as defined for sequence SEQ ID NO: 64 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 65 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is S, $X_{36}$ is C, $X_{37}$ is V, $X_{38}$ is V, $X_{39}$ is C and $X_{40}$ is Y, and at most sequence SEQ ID NO: 101 which corresponds to sequence SEQ ID NO: 46 in which $X_{18}$ to $X_{40}$ are as defined for sequence SEQ ID NO: 65 and $X_{41}$ is P, $X_{42}$ is A, $X_{43}$ is S, $X_{44}$ is Q $X_{45}$ is S, $X_{46}$ is K and $X_{47}$ is T, the peptides having at least sequence SEQ ID NO: 66 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is T, $X_{38}$ is V, $X_{39}$ is C and $X_{40}$ is Y, and at most sequence SEQ ID NO: 102 which corresponds to sequence SEQ ID NO: 46 in which $X_{18}$ to $X_{40}$ are as defined for sequence SEQ ID NO: 66 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 67 which corresponds to sequence SEQ ID NO: 45 in which $X_{18}$ is V, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is V, $X_{39}$ is C and $X_{40}$ is Y, and at most sequence SEQ ID NO: 103 which corresponds to sequence SEQ ID NO: 46 in which $X_{18}$ to $X_{40}$ are as defined for sequence SEQ ID NO: 67 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 68 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is K, $X_{32}$ is Q, $X_{33}$ is S, $X_{34}$ is A, $X_{35}$ is T, $X_{36}$ is C, $X_{37}$ is V, $X_{38}$ is V, $X_{39}$ is C and $X_{40}$ is Y, and at most sequence SEQ ID NO: 104 which corresponds to sequence SEQ ID NO: 46 in which $X_{18}$ to $X_{40}$ are as defined for sequence SEQ ID NO: 68 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 69 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is K, $X_{32}$ is Q, $X_{33}$ is S, $X_{34}$ is A, $X_{35}$ is T, $X_{36}$ is C, $X_{37}$ is V, $X_{38}$ is A, $X_{39}$ is C and $X_{40}$ is Y, and at most sequence SEQ ID NO: 106 which corresponds to sequence SEQ ID NO: 46 in which $X_{18}$ to $X_{40}$ are as defined for sequence SEQ ID NO: 69 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 70 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is T, $X_{34}$ is A, $X_{35}$ is T, $X_{36}$ is C, $X_{37}$ is V, $X_{38}$ is V, $X_{39}$ is C and $X_{40}$ is F, and at most sequence SEQ ID NO: 108 which corresponds to sequence SEQ ID NO: 46 in which $X_{18}$ to $X_{40}$ are as defined for sequence SEQ ID NO: 70 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 71 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is E, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is V, $X_{39}$ is C and $X_{40}$ is Y, and at most sequence SEQ ID NO: 111 which corresponds to sequence SEQ ID NO: 46 in which $X_{18}$ to $X_{40}$ are as defined for sequence SEQ ID NO: 71 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 72 which corresponds to sequence SEQ ID NO: 45 in which $X_{18}$ is L, $X_{19}$ is F, $X_{20}$ is G, $X_{21}$ is C, $X_{22}$ is I, $X_{23}$ is V, $X_{24}$ is K, $X_{25}$ is Q, $X_{26}$ is V, $X_{27}$ is E, $X_{28}$ is A, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is V, $X_{39}$ is C and $X_{40}$ is Y, and at most sequence SEQ ID NO: 112 which corresponds to sequence SEQ ID NO: 46 in which $X_{18}$ to $X_{40}$ are as defined for sequence SEQ ID NO: 72 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 73 which corresponds to sequence SEQ ID NO: 45 in which $X_{18}$ is L, $X_{19}$ is F, $X_{20}$ is G, $X_{21}$ is C, $X_{22}$ is I, $X_{23}$ is $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is I, $X_{38}$ is V, $X_{39}$ is C and $X_{40}$ is Y, and at most sequence SEQ ID NO: 113 which corresponds to sequence SEQ ID NO: 46 in which $X_{18}$ to $X_{40}$ are as defined for sequence SEQ ID NO: 73 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 74 which corresponds to sequence SEQ ID NO: 45 in which $X_{18}$ is L, $X_{19}$ is F, $X_{20}$ is G, $X_{21}$ is C, $X_{22}$ is I, $X_{23}$ is V, $X_{24}$ is K, $X_{25}$ is Q, $X_{26}$ is V, $X_{27}$ is E, $X_{28}$ is A, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is A, $X_{39}$ is C and $X_{40}$ is Y, and at most sequence SEQ ID NO: 114 which corresponds to sequence SEQ ID NO: 46 in which $X_{18}$ to $X_{40}$ are as defined for sequence SEQ ID NO: 74 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 75 which corresponds to sequence SEQ ID NO: 45 in which $X_{18}$ is L, $X_{19}$ is L, $X_{20}$ is G, $X_{21}$ is C, $X_{22}$ is I, $X_{23}$ is V, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is V, $X_{39}$ is C and $X_{40}$ is F, and at most a sequence chosen from the following sequences:
  i) sequence SEQ ID NO: 118 which corresponds to sequence SEQ ID NO: 46 in which $X_{18}$ to $X_{40}$ are as defined for sequence SEQ ID NO: 75 and $X_{41}$ is S, $X_{42}$ is A, $X_{43}$ is S, $X_{44}$ is Q, $X_{45}$ is S, $X_{46}$ is K and $X_{47}$ is T, and
  ii) sequence SEQ ID NO: 119 which corresponds to sequence SEQ ID NO: 46 in which $X_{18}$ to $X_{40}$ are as defined for sequence SEQ ID NO: 75 and $X_{41}$ is P, $X_{42}$ is A, $X_{43}$ is A, $X_{44}$ is Q, $X_{45}$ is S, $X_{46}$ is K and $X_{47}$ is T, the peptides having at least sequence SEQ ID NO: 76 which corresponds to sequence SEQ ID NO: 45 in which $X_{18}$ is L, $X_{19}$ is F, $X_{20}$ is G, $X_{21}$ is C, $X_{22}$ is I, $X_{23}$ is I, $X_{24}$ is R, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is I, $X_{38}$ is V, $X_{39}$ is C and $X_{40}$ is Y, and at most sequence SEQ ID NO: 121 which corresponds to sequence SEQ ID NO: 46 in which $X_{18}$ to $X_{40}$ are as defined for sequence SEQ ID NO: 76 and $X_{41}$ is P, $X_{42}$ is A, $X_{43}$ is A, $X_{44}$ is Q, $X_{45}$ is S, $X_{46}$ is K and $X_{47}$ is T, the peptides having at least sequence SEQ ID NO: 77 which corresponds to sequence SEQ ID NO: 45 in which $X_{18}$ is L, $X_{19}$ is F, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is I, $X_{38}$ is V, $X_{39}$ is C and $X_{40}$ is Y, and at most sequence SEQ ID NO: 122 which corresponds to sequence SEQ ID NO: 46 in which $X_{18}$ to $X_{40}$ are as defined for sequence SEQ ID NO: 77 and $X_{41}$ is P, $X_{42}$ is A, $X_{43}$ is A, $X_{44}$ is Q, $X_{45}$ is S, $X_{46}$ is K and $X_{47}$ is T, the peptides having at least sequence SEQ ID NO: 78 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is R, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is I, $X_{38}$ is V, $X_{39}$ is C and $X_{40}$ is F, and at most sequence SEQ ID NO: 123 which corresponds to sequence SEQ ID NO: 46 in which $X_{18}$ to $X_{40}$ are as defined for sequence SEQ ID NO: 78 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 79 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is R, $X_{25}$ is Q, $X_{26}$ is V, $X_{27}$ is E, $X_{28}$ is V, $X_{29}$ is M, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is V, $X_{39}$ is C and $X_{40}$ is Y, and at most sequence SEQ ID NO: 125 which corresponds to sequence SEQ ID NO: 46 in which $X_{18}$ to $X_{40}$ are as defined for sequence SEQ ID NO: 79 and $X_{41}$ is H, $X_{42}$ is A, $X_{43}$ is S, $X_{44}$ is Q, $X_{45}$ is S, $X_{46}$ is K and $X_{47}$ is T, and the peptides having at least sequence SEQ ID NO: 80 which corresponds to sequence SEQ ID NO: 45 in which $X_{18}$ is L, $X_{19}$ is F, $X_{20}$ is S, $X_{21}$ is T, $X_{22}$ is I, $X_{23}$ is I, $X_{24}$ is T, $X_{25}$ is E, $X_{26}$ is N, $X_{27}$ is C, $X_{28}$ is V, $X_{29}$ is V, $X_{30}$ is L, $X_{31}$ is T, $X_{32}$ is Q, $X_{33}$ is S, $X_{34}$ is G, $X_{35}$ is T, $X_{36}$ is A, $X_{37}$ is V, $X_{38}$ is V, $X_{39}$ is M and $X_{40}$ is Y, and at most sequence SEQ ID NO: 126 which corresponds to sequence SEQ ID NO: 46 in which $X_{18}$ to $X_{40}$ are as defined for sequence SEQ ID NO: 80 and $X_{41}$ is P, $X_{42}$ is A, $X_{43}$ is S, $X_{44}$ is Q, $X_{45}$ is A, $X_{46}$ is K and $X_{47}$ is T.

Preferably, the B peptide is chosen from the peptides of sequences SEQ ID NO: 47 to 80, the peptide of sequence SEQ ID NO: 47 being particularly preferred.

The C peptide in the compositions of the invention has at least the amino acid sequence SEQ ID NO: 127 as described previously.

According to one embodiment, the C peptide has at most the 57 amino acids as described in the following sequence SEQ ID NO: 128: NFIX$_{60}$GX$_{61}$ QYLAX$_{62}$ LST LPGNX$_{63}$AX$_{64}$X$_{65}$SX$_{47}$ MX$_{48}$FTX$_{49}$ X$_{50}$X$_{51}$ TSPLX$_{52}$X$_{53}$X$_{54}$ X$_{55}$ TLX$_{56}$FNIX$_{57}$ GGWVAX$_{58}$ QX$_{59}$X$_{66}$X$_{67}$X$_{68}$ in which $X_{47}$ to $X_{59}$ are as defined above and $X_{60}$ is T or S, $X_{61}$ is I, T or V, $X_{62}$ is G or A, $X_{63}$ is P or L, $X_{64}$ is I or M, $X_{65}$ is A, V or R, $X_{66}$ is A or R, $X_{67}$ is P, A or D and $X_{68}$ is P, A or S.

In this case, the C peptide is situated between positions 1767 and 1823 of the viral polyprotein.

According to another embodiment, the C peptide is chosen from the following peptides:
  the peptides having at least sequence SEQ ID NO: 129 which corresponds to sequence SEQ ID NO: 127 in which $X_{47}$ is L, $X_{48}$ is A, $X_{49}$ is A, $X_{50}$ is S, $X_{51}$ is I, $X_{52}$ is T, $X_{53}$ is T, $X_{54}$ is Q, $X_{55}$ is N, $X_{56}$ is L, $X_{57}$ is L, $X_{58}$ is A and $X_{59}$ is L and at most a sequence chosen from the following sequences:
    i) sequence SEQ ID NO: 147 which corresponds to sequence SEQ ID NO: 128 in which $X_{47}$ to $X_{59}$ are as defined for sequence SEQ ID NO: 129 and $X_{60}$ is T, $X_{61}$ is I, $X_{62}$ is G, $X_{63}$ is P, $X_{64}$ is I, $X_{65}$ is A, $X_{66}$ is A, $X_{67}$ is P and $X_{68}$ is P,
    ii) sequence SEQ ID NO: 153 which corresponds to sequence SEQ ID NO: 128 in which $X_{47}$ to $X_{59}$ are as defined for sequence SEQ ID NO: 129 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and $X_{68}$ is P,
    iii) sequence SEQ ID NO: 162 which corresponds to sequence SEQ ID NO: 128 in which $X_{47}$ to $X_{59}$ are as defined for sequence SEQ ID NO: 129 and $X_{60}$ is S, $X_{61}$ is I, $X_{62}$ is A, $X_{63}$ is P, $X_{64}$ is I, $X_{65}$ is A, $X_{66}$ is A, $X_{67}$ is P and $X_{68}$ is A, and
    iv) sequence SEQ ID NO: 167 which corresponds to sequence SEQ ID NO: 128 in which $X_{47}$ to $X_{59}$ are as defined for sequence SEQ ID NO: 129 and $X_{60}$ is S, $X_{61}$ is V, $X_{62}$ is G, $X_{63}$ is P, $X_{64}$ is I, $X_{65}$ is A, $X_{66}$ is A, $X_{67}$ is P and $X_{68}$ is P,
  the peptides having at least sequence SEQ ID NO: 130 which corresponds to sequence SEQ ID NO: 127 in which $X_{47}$ is L, $X_{48}$ is A, $X_{49}$ is A, $X_{50}$ is A, $X_{51}$ is V, $X_{52}$ is T, $X_{53}$ is T, $X_{54}$ is S, $X_{55}$ is Q, $X_{56}$ is L, $X_{57}$ is L, $X_{58}$ is A and $X_{59}$ is L and at most a sequence chosen from the following sequences:
    i) sequence SEQ ID NO: 148 which corresponds to sequence SEQ ID NO: 128 in which $X_{47}$ to $X_{59}$ are as defined for sequence SEQ ID NO: 130 and $X_{60}$ is S, $X_{61}$ is I, $X_{62}$ is G, $X_{63}$ is P, $X_{64}$ is I, $X_{65}$ is A, $X_{66}$ is A, $X_{67}$ is A and $X_{68}$ is P, and
    ii) sequence SEQ ID NO: 150 which corresponds to sequence SEQ ID NO: 128 in which $X_{47}$ to $X_{59}$ are as defined for sequence SEQ ID NO: 130 and $X_{60}$ is S, $X_{61}$ is T, $X_{62}$ is G, $X_{63}$ is P, $X_{64}$ is I, $X_{65}$ is A, $X_{66}$ is A, $X_{67}$ is A and $X_{68}$ is P, the peptides having at least sequence SEQ ID NO: 131 which corresponds to sequence SEQ ID NO: 127 in which $X_{47}$ is L, $X_{48}$ is A, $X_{49}$ is A, $X_{50}$ is A, $X_{51}$ is V, $X_{52}$ is T, $X_{53}$ is T, $X_{54}$ is G, $X_{55}$ is Q, $X_{56}$ is L, $X_{57}$ is L, $X_{58}$ is A and $X_{59}$ is L and at most sequence SEQ ID NO: 149 which corresponds to sequence SEQ ID NO: 128 in which $X_{47}$ to $X_{59}$ are as defined for sequence SEQ ID NO: 131 and $X_{60}$ is S, $X_{61}$ is I, $X_{62}$ is G, $X_{63}$ is P, $X_{64}$ is I, $X_{65}$ is A, $X_{66}$ is A, $X_{67}$ is A and $X_{68}$ is P the peptides having at least sequence SEQ ID NO: 132 which corresponds to sequence SEQ ID NO: 127 in which $X_{47}$ is L, $X_{48}$ is A, $X_{49}$ is A, $X_{50}$ is S, $X_{51}$ is I, $X_{52}$ is T, $X_{53}$ is T, $X_{54}$ is Q, $X_{55}$ is H, $X_{56}$ is L, $X_{57}$ is L, $X_{58}$ is A and $X_{59}$ is L and at most a sequence chosen from the following sequences:
  i) sequence SEQ ID NO: 151 which corresponds to sequence SEQ ID NO: 128 in which $X_{47}$ to $X_{59}$ are as defined for sequence SEQ ID NO: 132 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and $X_{68}$ is P,
  ii) sequence SEQ ID NO: 155 which corresponds to sequence SEQ ID NO: 128 in which $X_{47}$ to $X_{59}$ are as defined for sequence SEQ ID NO: 132 and $X_{60}$ is S, $X_{61}$ is I, $X_{62}$ is G, $X_{63}$ is P, $X_{64}$ is I, $X_{65}$ is V, $X_{66}$ is A, $X_{67}$ is P and $X_{68}$ is P,
  iii) sequence SEQ ID NO: 168 which corresponds to sequence SEQ ID NO: 128 in which $X_{47}$ to $X_{59}$ are as defined for sequence SEQ ID NO: 132 and $X_{60}$ is S, $X_{61}$ is V, $X_{62}$ is G, $X_{63}$ is P, $X_{64}$ is I, $X_{65}$ is A, $X_{66}$ is A, $X_{67}$ is P and $X_{68}$ is P, and
  iv) sequence SEQ ID NO: 171 which corresponds to sequence SEQ ID NO: 128 in which $X_{47}$ to $X_{59}$ are as defined for sequence SEQ ID NO: 132 and $X_{60}$ is 5, $X_{61}$ is I, $X_{62}$ is G, $X_{63}$ is L, $X_{64}$ is I, $X_{65}$ is A, $X_{66}$ is A, $X_{67}$ is P and $X_{68}$ is P, the peptides having at least sequence SEQ ID NO: 133 which corresponds to sequence SEQ ID NO: 127 in which $X_{47}$ is L, $X_{48}$ is A, $X_{49}$ is A, $X_{50}$ is S, $X_{51}$ is I, $X_{52}$ is T, $X_{53}$ is T, $X_{54}$ is Q, $X_{55}$ is S, $X_{56}$ is L, $X_{57}$ is L, $X_{58}$ is A and $X_{59}$ is L and at most sequence SEQ ID NO: 152 which corresponds to sequence SEQ ID NO: 128 in which $X_{47}$ to $X_{59}$ are as defined for sequence SEQ ID NO: 133 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and $X_{68}$ is P, the peptides having at least sequence SEQ ID NO: 134 which corresponds to sequence SEQ ID NO: 127 in which $X_{47}$ is L, $X_{48}$ is A, $X_{49}$ is A, $X_{50}$ is S, $X_{51}$ is I, $X_{52}$ is T, $X_{53}$ is T, $X_{54}$ is Q, $X_{55}$ is Y, $X_{56}$ is L, $X_{57}$ is L, $X_{58}$ is A and $X_{59}$ is L and at most a sequence chosen from the following sequences:
  i) sequence SEQ ID NO: 154 which corresponds to sequence SEQ ID NO: 128 in which $X_{47}$ to $X_{59}$ are as defined for sequence SEQ ID NO: 134 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and $X_{68}$ is P, and
  ii) sequence SEQ ID NO: 169 which corresponds to sequence SEQ ID NO: 128 in which $X_{47}$ to $X_{59}$ are as defined for sequence SEQ ID NO: 134 and $X_{60}$ is S, $X_{61}$ is V, $X_{62}$ is G, $X_{63}$ is P, $X_{64}$ is I, $X_{65}$ is A, $X_{66}$ is A, $X_{67}$ is P and $X_{68}$ is P, the peptides having at least sequence SEQ ID NO: 135 which corresponds to sequence SEQ ID NO: 127 in which $X_{47}$ is L, $X_{48}$ is A, $X_{49}$ is A, $X_{50}$ is S, $X_{51}$ is V, $X_{52}$ is T, $X_{53}$ is T, $X_{54}$ is Q, $X_{55}$ is N, $X_{56}$ is L, $X_{57}$ is L, $X_{58}$ is A and $X_{59}$ is L and at most sequence SEQ ID NO: 156 which corresponds to sequence SEQ ID NO: 128 in which $X_{47}$ to $X_{59}$ are as defined for sequence SEQ ID NO: 135 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and $X_{68}$ is P, the peptides having at least sequence SEQ ID NO: 136 which corresponds to sequence SEQ ID NO: 127 in which $X_{47}$ is L, $X_{48}$ is A, $X_{49}$ is A, $X_{50}$ is S, $X_{51}$ is V, $X_{52}$ is T, $X_{53}$ is T, $X_{54}$ is Q, $X_{55}$ is S, $X_{56}$ is L, $X_{57}$ is L, $X_{58}$ is A and $X_{59}$ is L and at most a sequence chosen from the following sequences:
  i) sequence SEQ ID NO: 157 which corresponds to sequence SEQ ID NO: 128 in which $X_{47}$ to $X_{59}$ are as defined for sequence SEQ ID NO: 136 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and $X_{68}$ is P, and
  ii) sequence SEQ ID NO: 170 which corresponds to sequence SEQ ID NO: 128 in which $X_{47}$ to $X_{59}$ are as defined for sequence SEQ ID NO: 136 and $X_{60}$ is S, $X_{61}$ is V, $X_{62}$ is G, $X_{63}$ is P, $X_{64}$ is I, $X_{65}$ is A, $X_{66}$ is A, $X_{67}$ is P and $X_{68}$ is P, the peptides having at least sequence SEQ ID NO: 137 which corresponds to sequence SEQ ID NO: 127 in which $X_{47}$ is L, $X_{48}$ is A, $X_{49}$ is A, $X_{50}$ is S, $X_{51}$ is I, $X_{52}$ is T, $X_{53}$ is T, $X_{54}$ is Q, $X_{55}$ is T, $X_{56}$ is M, $X_{57}$ is L, $X_{58}$ is A and $X_{59}$ is L and at most sequence SEQ ID NO: 158 which corresponds to sequence SEQ ID NO: 128 in which $X_{47}$ to $X_{59}$ are as defined for sequence SEQ ID NO: 137 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and $X_{68}$ is P, the peptides having at least sequence SEQ ID NO: 138 which corresponds to sequence SEQ ID NO: 127 in which $X_{47}$ is L, $X_{48}$ is A, $X_{49}$ is A, $X_{50}$ is S, $X_{51}$ is V, $X_{52}$ is T, $X_{53}$ is T, $X_{54}$ is Q, $X_{55}$ is Y, $X_{56}$ is L, $X_{57}$ is L, $X_{58}$ is A and $X_{59}$ is I and at most sequence SEQ ID NO: 159 which corresponds to sequence SEQ ID NO: 128 in which $X_{47}$ to $X_{59}$ are as defined for sequence SEQ ID NO: 138 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and $X_{68}$ is P, the peptides having at least sequence SEQ ID NO: 139 which corresponds to sequence SEQ ID NO: 127 in which $X_{47}$ is P, $X_{48}$ is A, $X_{49}$ is A, $X_{50}$ is S, $X_{51}$ is I, $X_{52}$ is T, $X_{53}$ is T, $X_{54}$ is Q, $X_{55}$ is H, $X_{56}$ is L, $X_{57}$ is L, $X_{58}$ is A and $X_{59}$ is L and at most sequence SEQ ID NO: 160 which corresponds to sequence SEQ ID NO: 128 in which $X_{47}$ to $X_{59}$ are as defined for sequence SEQ ID NO: 139 and $X_{60}$ is S, $X_{61}$ is I, $X_{62}$ is G, $X_{63}$ is P, $X_{64}$ is I, $X_{65}$ is R, $X_{66}$ is A, $X_{67}$ is P and $X_{68}$ is P, the peptides having at least sequence SEQ ID NO: 140 which corresponds to sequence SEQ ID NO: 127 in which $X_{47}$ is L, $X_{48}$ is A, $X_{49}$ is A, $X_{50}$ is S, $X_{51}$ is I, $X_{52}$ is T, $X_{53}$ is I, $X_{54}$ is Q, $X_{55}$ is H, $X_{56}$ is L, $X_{57}$ is L, $X_{58}$ is A and $X_{59}$ is P and at most sequence SEQ ID NO: 161 which corresponds to sequence SEQ ID NO: 128 in which $X_{47}$ to $X_{59}$ are as defined for sequence SEQ ID NO: 140 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and $X_{68}$ is P.

the peptides having at least sequence SEQ ID NO: 141 which corresponds to sequence SEQ ID NO: 127 in which $X_{47}$ is L, $X_{48}$ is A, $X_{49}$ is S, $X_{50}$ is S, $X_{51}$ is I, $X_{52}$ is T, $X_{53}$ is T, $X_{54}$ is Q, $X_{55}$ is S, $X_{56}$ is L, $X_{57}$ is L, $X_{58}$ is A and $X_{59}$ is L and at most sequence SEQ ID NO: 163 which corresponds to sequence SEQ ID NO: 128 in which $X_{47}$ to $X_{59}$ are as defined for sequence SEQ ID NO: 141 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and $X_{68}$ is P, the peptides having at least sequence SEQ ID NO: 142 which corresponds to sequence SEQ ID NO: 127 in which $X_{47}$ is L, $X_{48}$ is A, $X_{49}$ is A, $X_{50}$ is S, $X_{51}$ is I, $X_{52}$ is S, $X_{53}$ is T, $X_{54}$ is Q, $X_{55}$ is N, $X_{56}$ is L, $X_{57}$ is W, $X_{58}$ is A and $X_{59}$ is L and at most sequence SEQ ID NO: 164 which corresponds to sequence SEQ ID NO: 128 in which $X_{47}$ to $X_{59}$ are as defined for sequence SEQ ID NO: 142 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and $X_{68}$ is P, the peptides having at least sequence SEQ ID NO: 143 which corresponds to sequence SEQ ID NO: 127 in which $X_{47}$ is L, $X_{48}$ is A, $X_{49}$ is A, $X_{50}$ is S, $X_{51}$ is I, $X_{52}$ is T, $X_{53}$ is T, $X_{54}$ is Q, $X_{55}$ is N, $X_{56}$ is M, $X_{57}$ is L, $X_{58}$ is A and $X_{59}$ is L and at most sequence SEQ ID NO: 165 which corresponds to sequence SEQ ID NO: 128 in which $X_{47}$ to $X_{59}$ are as defined for sequence SEQ ID NO: 143 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and $X_{68}$ is P, the peptides having at least sequence SEQ ID NO: 144 which corresponds to sequence SEQ ID NO: 127 in which $X_{47}$ is L, $X_{48}$ is A, $X_{49}$ is A, $X_{50}$ is S, $X_{51}$ is I, $X_{52}$ is T, $X_{53}$ is T, $X_{54}$ is Q, $X_{55}$ is H, $X_{56}$ is M, $X_{57}$ is L, $X_{58}$ is A and $X_{59}$ is L and at most sequence SEQ ID NO: 166 which corresponds to sequence SEQ ID NO: 128 in which $X_{47}$ to $X_{59}$ are as defined for sequence SEQ ID NO: 144 and $X_{60}$ is S, $X_{61}$ is I, $X_{62}$ is G, $X_{63}$ is P, $X_{64}$ is M, $X_{65}$ is A, $X_{66}$ is A, $X_{67}$ is P and $X_{68}$ is P, the peptides having at least sequence SEQ ID NO: 145 which corresponds to sequence SEQ ID NO: 127 in which $X_{47}$ is L, $X_{48}$ is A, $X_{49}$ is A, $X_{50}$ is S, $X_{51}$ is I, $X_{52}$ is A, $X_{53}$ is T, $X_{54}$ is Q, $X_{55}$ is Y, $X_{56}$ is L, $X_{57}$ is L, $X_{58}$ is A and $X_{59}$ is L and at most sequence SEQ ID NO: 172 which corresponds to sequence SEQ ID NO: 128 in which $X_{47}$ to $X_{59}$ are as defined for sequence SEQ ID NO: 145 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and $X_{68}$ is P, the peptides having at least sequence SEQ ID NO: 146 which corresponds to sequence SEQ ID NO: 127 in which $X_{47}$ is L, $X_{48}$ is S, $X_{49}$ is A, $X_{50}$ is A, $X_{51}$ is V, $X_{52}$ is T, $X_{53}$ is T, $X_{54}$ is Q, $X_{55}$ is Q, $X_{56}$ is L, $X_{57}$ is L, $X_{58}$ is S and $X_{59}$ is I and at most sequence SEQ ID NO: 173 which corresponds to sequence SEQ ID NO: 128 in which $X_{47}$ to $X_{59}$ are as defined for sequence SEQ ID NO: 146 and $X_{60}$ is S, $X_{61}$ is I, $X_{62}$ is G, $X_{63}$ is P, $X_{64}$ is I, $X_{65}$ is A, $X_{66}$ is R, $X_{67}$ is D and $X_{68}$ is S.

Preferably, the C peptide is chosen from the peptides of sequences SEQ ID NO: 129 to 146, the peptide of sequence SEQ ID NO: 129 being particularly preferred.

The D peptide in the compositions of the invention has at least the amino acid sequence SEQ ID NO: 174 as described above.

According to one embodiment of the invention, the D peptide has at most the 44 amino acids as described in the following sequence SEQ ID NO: 175: KGGX$_{69}$KX$_{70}$ARX$_{71}$IVX$_{72}$PX$_{73}$LGX$_{74}$RVCEKX$_{75}$ALX$_{76}$X$_{77}$VX$_{78}$X$_{79}$X$_{80}$X$_{81}$X$_{82}$X$_{83}$X$_{84}$VMGX$_{85}$X$_{86}$YX$_{87}$X$_{88}$Q in which $X_{69}$ to $X_{81}$ are as defined above and $X_{82}$ is P or A, $X_{83}$ is Q, L, H, R, K or P, $X_{84}$ is A, T, V or P, $X_{85}$ is P, S or A, $X_{86}$ is S or A, $X_{87}$ is G or R and $X_{88}$ is F or C.

In this case, the D peptide is situated between positions 2570 and 2613 of the viral polyprotein.

According to a further embodiment, the D peptide is chosen from the following peptides:

the peptides having at least sequence SEQ ID NO: 176 which corresponds to sequence SEQ ID NO: 174 in which $X_{69}$ is R, $X_{70}$ is P, $X_{71}$ is L, $X_{72}$ is F, $X_{73}$ is D, $X_{74}$ is V, $X_{75}$ is M, $X_{76}$ is Y, $X_{77}$ is D, $X_{78}$ is V, $X_{79}$ is S, $X_{80}$ is T and $X_{81}$ is L, and at most a sequence chosen from:
i) sequence SEQ ID NO: 188 which corresponds to sequence SEQ ID NO: 175 in which $X_{69}$ to $X_{81}$ are as defined for sequence SEQ ID NO: 176 and $X_{82}$ is P, $X_{83}$ is Q, $X_{84}$ is A, $X_{85}$ is P, $X_{86}$ is S, $X_{87}$ is G and $X_{88}$ is F,
ii) sequence SEQ ID NO: 192 which corresponds to sequence SEQ ID NO: 175 in which $X_{69}$ to $X_{81}$ are as defined for sequence SEQ ID NO: 176 and $X_{82}$ is P, $X_{83}$ is Q, $X_{84}$ is A, $X_{85}$ is S, $X_{86}$ is S, $X_{87}$ is G and $X_{88}$ is F,
iii) sequence SEQ ID NO: 193 which corresponds to sequence SEQ ID NO: 175 in which $X_{69}$ to $X_{81}$ are as defined for sequence SEQ ID NO: 176 and $X_{82}$ is P, $X_{83}$ is Q, $X_{84}$ is A, $X_{85}$ is A, $X_{86}$ is S, $X_{87}$ is G and $X_{88}$ is F,
iv) sequence SEQ ID NO: 194 which corresponds to sequence SEQ ID NO: 175 in which $X_{69}$ to $X_{81}$ are as defined for sequence SEQ ID NO: 176 and $X_{82}$ is P, $X_{83}$ is Q, $X_{84}$ is V, $X_{85}$ is S, $X_{86}$ is S, $X_{87}$ is G and $X_{88}$ is F,
v) sequence SEQ ID NO: 201 which corresponds to sequence SEQ ID NO: 175 in which $X_{69}$ to $X_{81}$ are as defined for sequence SEQ ID NO: 176 and $X_{82}$ is P, $X_{83}$ is R, $X_{84}$ is A, $X_{85}$ is S, $X_{86}$ is S, $X_{87}$ is G and $X_{88}$ is C,
vi) sequence SEQ ID NO: 202 which corresponds to sequence SEQ ID NO: 175 in which $X_{69}$ to $X_{81}$ are as defined for sequence SEQ ID NO: 176 and $X_{82}$ is P, $X_{83}$ is Q, $X_{84}$ is P, $X_{85}$ is S, $X_{86}$ is S, $X_{87}$ is G and $X_{88}$ is F,
vii) sequence SEQ ID NO: 203 which corresponds to sequence SEQ ID NO: 175 in which $X_{69}$ to $X_{81}$ are as defined for sequence SEQ ID NO: 176 and $X_{82}$ is P, $X_{83}$ is H, $X_{84}$ is A, $X_{85}$ is S, $X_{86}$ is S, $X_{87}$ is G and $X_{88}$ is F,
viii) sequence SEQ ID NO: 204 which corresponds to sequence SEQ ID NO: 175 in which $X_{69}$ to $X_{81}$ are as defined for sequence SEQ ID NO: 176 and $X_{82}$ is P, $X_{83}$ is Q, $X_{84}$ is A, $X_{85}$ is S, $X_{86}$ is A, $X_{87}$ is G and $X_{88}$ is F,
ix) sequence SEQ ID NO: 205 which corresponds to sequence SEQ ID NO: 175 in which $X_{69}$ to $X_{81}$ are as defined for sequence SEQ ID NO: 176 and $X_{82}$ is P, $X_{83}$ is Q, $X_{84}$ is A, $X_{85}$ is S, $X_{86}$ is S, $X_{87}$ is R and $X_{88}$ is F, and
x) sequence SEQ ID NO: 210 which corresponds to sequence SEQ ID NO: 175 in which $X_{69}$ to $X_{81}$ are as defined for sequence SEQ ID NO: 176 and $X_{82}$ is P, $X_{83}$ is H, $X_{84}$ is T, $X_{85}$ is S, $X_{86}$ is S, $X_{87}$ is G and $X_{88}$ is F, the peptides having at least sequence SEQ ID NO: 177 which corresponds to sequence SEQ ID NO: 174 in which $X_{69}$ is R, $X_{70}$ is P, $X_{71}$ is L, $X_{72}$ is F, $X_{73}$ is D, $X_{74}$ is V, $X_{75}$ is M, $X_{76}$ is Y, $X_{77}$ is D, $X_{78}$ is V, $X_{79}$ is S, $X_{80}$ is K and $X_{81}$ is L, and at most a sequence chosen from the following sequences:
i) sequence SEQ ID NO: 189 which corresponds to sequence SEQ ID NO: 175 in which $X_{69}$ to $X_{81}$ are as defined for sequence SEQ ID NO: 177 and $X_{82}$ is P, $X_{83}$ is L, $X_{84}$ is A, $X_{85}$ is S, $X_{86}$ is S, $X_{87}$ is G and $X_{88}$ is F, and
ii) sequence SEQ ID NO: 190 which corresponds to sequence SEQ ID NO: 175 in which $X_{69}$ to $X_{81}$ are as defined for sequence SEQ ID NO: 177 and $X_{82}$ is P, $X_{83}$ is P, $X_{84}$ is A, $X_{85}$ is S, $X_{86}$ is S, $X_{87}$ is G and $X_{88}$ is F, the peptides having at least sequence SEQ ID NO: 178 which corresponds to sequence SEQ ID NO: 174 in which $X_{69}$ is R, $X_{70}$ is P, $X_{71}$ is L, $X_{72}$ is F, $X_{73}$ is D, $X_{74}$ est V, $X_{75}$ is M, $X_{76}$ is Y, $X_{77}$ is D, $X_{78}$ is V, $X_{79}$ is T, $X_{80}$ is K and $X_{81}$ is L, and at most sequence SEQ ID NO: 191 which corresponds to sequence SEQ ID NO: 175 in which $X_{69}$ to $X_{81}$ are as defined for sequence SEQ ID NO: 178 and $X_{82}$ is P, $X_{83}$ is L, $X_{84}$ is A, $X_{85}$ is S, $X_{86}$ is S, $X_{87}$ is G and $X_{88}$ is F, the peptides having at least sequence SEQ ID NO: 179 which corresponds to sequence SEQ ID NO: 174 in which $X_{69}$ is Q, $X_{70}$ is P, $X_{71}$ is L, $X_{72}$ is F, $X_{73}$ is D, $X_{74}$ is V, $X_{75}$ is M, $X_{76}$ is Y, $X_{77}$ is D, $X_{78}$ is V, $X_{79}$ is S, $X_{80}$ is T and $X_{81}$ is L, and at most sequence SEQ ID NO: 195 which corresponds to sequence SEQ ID NO: 175 in which $X_{69}$ to $X_{81}$ are as defined for sequence SEQ ID NO: 179 and $X_{82}$ is P, $X_{83}$ is Q, $X_{84}$ is A, $X_{85}$ is S, $X_{86}$ is S, $X_{87}$ is G and $X_{88}$ is F, the peptides having at least sequence SEQ ID NO: 180 which corresponds to sequence SEQ ID NO: 174 in which $X_{69}$ is R, $X_{70}$ is A, $X_{71}$ is L, $X_{72}$ is F, $X_{73}$ is D, $X_{74}$ is V, $X_{75}$ is M, $X_{76}$ is Y, $X_{77}$ is D, $X_{78}$ is V, $X_{79}$ is S, $X_{80}$ is T and $X_{81}$ is L, and at most a sequence chosen from the following sequences:
  i) sequence SEQ ID NO: 196 which corresponds to sequence SEQ ID NO: 175 in which $X_{69}$ to $X_{81}$ are as defined for sequence SEQ ID NO: 180 and $X_{82}$ is P, $X_{83}$ is Q, $X_{84}$ is A, $X_{85}$ is S, $X_{86}$ is S, $X_{87}$ is G and $X_{88}$ is F, and
  ii) sequence SEQ ID NO: 206 which corresponds to sequence SEQ ID NO: 175 in which $X_{69}$ to $X_{81}$ are as defined for sequence SEQ ID NO: 180 and $X_{82}$ is P, $X_{83}$ is Q, $X_{84}$ is A, $X_{85}$ is P, $X_{86}$ is S, $X_{87}$ is G and $X_{88}$ is F, the peptides having at least sequence SEQ ID NO: 181 which corresponds to sequence SEQ ID NO: 174 in which $X_{69}$ is R, $X_{70}$ is P, $X_{71}$ is L, $X_{72}$ is F, $X_{73}$ is D, $X_{74}$ is V, $X_{75}$ is M, $X_{76}$ is Y, $X_{77}$ is D, $X_{78}$ is V, $X_{79}$ is S, $X_{80}$ is I and $X_{81}$ is L, and at most sequence SEQ ID NO: 197 which corresponds to sequence SEQ ID NO: 175 in which $X_{69}$ to $X_{81}$ are as defined for sequence SEQ ID NO: 181 and $X_{82}$ is P, $X_{83}$ is Q, $X_{84}$ is A, $X_{85}$ is S, $X_{86}$ is S, $X_{87}$ is G and $X_{88}$ is F, the peptides having at least sequence SEQ ID NO: 182 which corresponds to sequence SEQ ID NO: 174 in which $X_{69}$ is R, $X_{70}$ is P, $X_{71}$ is L, $X_{72}$ is F, $X_{73}$ is E, $X_{74}$ is V, $X_{75}$ is M, $X_{76}$ is Y, $X_{77}$ is D, $X_{78}$ is V, $X_{79}$ is S, $X_{80}$ is T and $X_{81}$ is L, and at most a sequence chosen from the following sequences:
  i) sequence SEQ ID NO: 198 which corresponds to sequence SEQ ID NO: 175 in which $X_{69}$ to $X_{81}$ are as defined for sequence SEQ ID NO: 182 and $X_{82}$ is P, $X_{83}$ is Q, $X_{84}$ is A, $X_{85}$ is S, $X_{86}$ is S, $X_{87}$ is G and $X_{88}$ is F, and
  ii) sequence SEQ ID NO: 209 which corresponds to sequence SEQ ID NO: 175 in which $X_{69}$ to $X_{81}$ are as defined for sequence SEQ ID NO: 182 and $X_{82}$ is P, $X_{83}$ is Q, $X_{84}$ is A, $X_{85}$ is P, $X_{86}$ is S, $X_{87}$ is G and $X_{88}$ is F, the peptides having at least sequence SEQ ID NO: 183 which corresponds to sequence SEQ ID NO: 174 in which $X_{69}$ is R, $X_{70}$ is P, $X_{71}$ is F, $X_{72}$ is F, $X_{73}$ is D, $X_{74}$ is V, $X_{75}$ is M, $X_{76}$ is Y, $X_{77}$ is D, $X_{78}$ is V, $X_{79}$ is S, $X_{80}$ is T and $X_{81}$ is L, and at most a sequence chosen from the following sequences:
  i) sequence SEQ ID NO: 199 which corresponds to sequence SEQ ID NO: 175 in which $X_{69}$ to $X_{81}$ are as defined for sequence SEQ ID NO: 183 and $X_{82}$ is P, $X_{83}$ is K, $X_{84}$ is A, $X_{85}$ is S, $X_{86}$ is S, $X_{87}$ is G and $X_{88}$ is F, and
  ii) sequence SEQ ID NO: 200 which corresponds to sequence SEQ ID NO: 175 in which $X_{69}$ to $X_{81}$ are as defined for sequence SEQ ID NO: 183 and $X_{82}$ is P, $X_{83}$ is Q, $X_{84}$ is A, $X_{85}$ is S, $X_{86}$ is S, $X_{87}$ is G and $X_{88}$ is F, the peptides having at least sequence SEQ ID NO: 184 which corresponds to sequence SEQ ID NO: 174 in which $X_{69}$ is R, $X_{70}$ is A, $X_{71}$ is L, $X_{72}$ is F, $X_{73}$ is D, $X_{74}$ is V, $X_{75}$ is M, $X_{76}$ is Y, $X_{77}$ is N, $X_{78}$ is V, $X_{79}$ is S, $X_{80}$ is T and $X_{81}$ is L, and at most sequence SEQ ID NO: 207 which corresponds to sequence SEQ ID NO: 175 in which $X_{69}$ to $X_{81}$ are as defined for sequence SEQ ID NO: 184 and $X_{82}$ is P, $X_{83}$ is Q, $X_{84}$ is A, $X_{85}$ is S, $X_{86}$ is S, $X_{87}$ is G and $X_{88}$ is F, the peptides having at least sequence SEQ ID NO: 185 which corresponds to sequence SEQ ID NO: 174 in which $X_{69}$ is R, $X_{70}$ is P, $X_{71}$ is L, $X_{72}$ is F, $X_{73}$ is D, $X_{74}$ is V, $X_{75}$ is M, $X_{76}$ is Y, $X_{77}$ is D, $X_{78}$ is V, $X_{79}$ is S, $X_{80}$ is N and $X_{81}$ is L, and at most sequence SEQ ID NO: 208 which corresponds to sequence SEQ ID NO: 175 in which $X_{69}$ to $X_{81}$ are as defined for sequence SEQ ID NO: 185 and $X_{82}$ is P, $X_{83}$ is Q, $X_{84}$ is A, $X_{85}$ is S, $X_{86}$ is S, $X_{87}$ is G and $X_{88}$ is F, the peptides having at least sequence SEQ ID NO: 186 which corresponds to sequence SEQ ID NO: 174 in which $X_{69}$ is R, $X_{70}$ is P, $X_{71}$ is L, $X_{72}$ is Y, $X_{73}$ is D, $X_{74}$ is V, $X_{75}$ is M, $X_{76}$ is Y, $X_{77}$ is D, $X_{78}$ is V, $X_{79}$ is S, $X_{80}$ is T and $X_{81}$ is L, and at most sequence SEQ ID NO: 211 which corresponds to sequence SEQ ID NO: 175 in which $X_{69}$ to $X_{81}$ are as defined for sequence SEQ ID NO: 186 and $X_{82}$ is P, $X_{83}$ is Q, $X_{84}$ is A, $X_{85}$ is S, $X_{86}$ is S, $X_{87}$ is G and $X_{88}$ is F, the peptides having at least sequence SEQ ID NO: 187 which corresponds to sequence SEQ ID NO: 174 in which $X_{69}$ is R, $X_{70}$ is P, $X_{71}$ is L, $X_{72}$ is Y, $X_{73}$ is D, $X_{74}$ is S, $X_{75}$ is R, $X_{76}$ is H, $X_{77}$ is D, $X_{78}$ is Y, $X_{79}$ is K, $X_{80}$ is K and $X_{81}$ is T, and at most sequence SEQ ID NO: 212 which corresponds to sequence SEQ ID NO: 175 in which $X_{69}$ to $X_{81}$ are as defined for sequence SEQ ID NO: 187 and $X_{82}$ is A, $X_{83}$ is L, $X_{84}$ is A, $X_{85}$ is A, $X_{86}$ is A, $X_{87}$ is G and $X_{88}$ is F.

Preferably, the D peptide is chosen from the peptides of sequences SEQ ID NO: 176 to 187, the peptide of sequence SEQ ID NO: 176 being preferred.

The A, B, C or D peptides as defined by the preceding sequences 1 to 212 are novel and also constitute a subject of the invention.

Thus, according to the invention:

the A peptide has at least the amino acid sequence SEQ ID NO: 1 and at most sequence SEQ ID NO: 2; in particular it is chosen from the peptides:
  having at least sequence SEQ ID NO: 3 and at most sequence SEQ ID NO: 19,
  having at least sequence SEQ ID NO: 4 and at most a sequence chosen from sequences SEQ ID NO: 20, SEQ ID NO: 24, SEQ ID, N°32 and SEQ ID NO: 34,
  having at least sequence SEQ ID NO: 5 and at most a sequence chosen from sequences SEQ ID NO: 21, SEQ ID NO: 28 and SEQ ID NO: 36,
  having at least sequence SEQ ID NO: 6 and at most a sequence chosen from sequences SEQ ID NO: 22, SEQ ID NO: 27 and SEQ ID NO: 41,
  having at least sequence SEQ ID NO: 7 and at most a sequence chosen from sequences SEQ ID NO: 23 and SEQ ID NO: 37,
  having at least sequence SEQ ID NO: 8 and at most sequence SEQ ID NO: 25, having at least sequence SEQ ID NO: 9 and at most sequence SEQ ID NO: 26,
having at least sequence SEQ ID NO: 10 and at most sequence SEQ ID NO: 29,
having at least sequence SEQ ID NO: 11 and at most sequence SEQ ID NO: 30,
having at least sequence SEQ ID NO: 12 and at most sequence SEQ ID NO: 31,
having at least sequence SEQ ID NO: 13 and at most sequence SEQ ID NO: 33,
having at least sequence SEQ ID NO: 14 and at most a sequence chosen from sequences SEQ ID NO: 35 and SEQ ID NO: 39,
having at least sequence SEQ ID NO: 15 and at most sequence SEQ ID NO: 38,
having at least sequence SEQ ID NO: 16 and at most a sequence chosen from sequences SEQ ID NO: 40 and SEQ ID NO: 42,
having at least sequence SEQ ID NO: 17 and at most sequence SEQ ID NO: 43, and
having at least sequence SEQ ID NO: 18 and at most sequence SEQ ID NO: 44, the peptides of sequence SEQ ID NO: 3 to 18 being preferred and the peptide of sequence SEQ ID NO: 3 being particularly preferred, the B peptide has at least the amino acid sequence SEQ ID NO: 45 and at most sequence SEQ ID NO: 46; in particular, the B peptide is chosen from the peptides:
having at least sequence SEQ ID NO: 47 and at most sequence SEQ ID NO: 81,
having at least sequence SEQ ID NO: 48 and at most sequence SEQ ID NO: 82,
having at least sequence SEQ ID NO: 49 and at most sequence SEQ ID NO: 83,
having at least sequence SEQ ID NO: 50 and at most a sequence chosen from sequences SEQ ID NO: 84, SEQ ID NO: 90, SEQ ID NO: 105, SEQ ID NO: 107 and SEQ ID NO: 116,
having at least sequence SEQ ID NO: 51 and at most a sequence chosen from sequences SEQ ID NO: 85 and SEQ ID NO: 124,
having at least sequence SEQ ID NO: 52 and at most a sequence chosen from sequences SEQ ID NO: 86 and SEQ ID NO: 120,
having at least sequence SEQ ID NO: 53 and at most sequence SEQ ID NO: 87,
having at least sequence SEQ ID NO: 54 and at most a sequence chosen from sequences SEQ ID NO: 88 and SEQ ID NO: 117,
having at least sequence SEQ ID NO: 55 and at most sequence SEQ ID NO: 89,
having at least sequence SEQ ID NO: 56 and at most a sequence chosen from sequences SEQ ID NO: 91 and SEQ ID NO: 92,
having at least sequence SEQ ID NO: 57 and at most sequence SEQ ID NO: 93,
having at least sequence SEQ ID NO: 58 and at most a sequence chosen from sequences SEQ ID NO: 94 and SEQ ID NO: 110,
having at least sequence SEQ ID NO: 59 and at most sequence SEQ ID NO: 95,
having at least sequence SEQ ID NO: 60 and at most a sequence chosen from sequences SEQ ID NO: 96 and SEQ ID NO: 115,
having at least sequence SEQ ID NO: 61 and at most sequence SEQ ID NO: 97,
having at least sequence SEQ ID NO: 62 and at most a sequence chosen from sequences SEQ ID NO: 98 and SEQ ID NO: 109,
having at least sequence SEQ ID NO: 63 and at most sequence SEQ ID NO: 99,
having at least sequence SEQ ID NO: 64 and at most sequence SEQ ID NO: 100,
having at least sequence SEQ ID NO: 65 and at most sequence SEQ ID NO: 101,
having at least sequence SEQ ID NO: 66 and at most sequence SEQ ID NO: 102,
having at least sequence SEQ ID NO: 67 and at most sequence SEQ ID NO: 103,
having at least sequence SEQ ID NO: 68 and at most sequence SEQ ID NO: 104,
having at least sequence SEQ ID NO: 69 and at most sequence SEQ ID NO: 106,
having at least sequence SEQ ID NO: 70 and at most sequence SEQ ID NO: 108,
having at least sequence SEQ ID NO: 71 and at most sequence SEQ ID NO: 111,
having at least sequence SEQ ID NO: 72 and at most sequence SEQ ID NO: 112,
having at least sequence SEQ ID NO: 73 and at most sequence SEQ ID NO: 113,
having at least sequence SEQ ID NO: 74 and at most sequence SEQ ID NO: 114,
having at least sequence SEQ ID NO: 75 and at most a sequence chosen from sequences SEQ ID NO: 118 and SEQ ID NO: 119
having at least sequence SEQ ID NO: 76 and at most sequence SEQ ID NO: 121,
having at least sequence SEQ ID NO: 77 and at most sequence SEQ ID NO: 122,
having at least sequence SEQ ID NO: 78 and at most sequence SEQ ID NO: 123,
having at least sequence SEQ ID NO: 79 and at most sequence SEQ ID NO: 125, and
having at least sequence SEQ ID NO: 80 and at most sequence SEQ ID NO: 126, the peptides of sequences SEQ ID NO: 47 to 80 being preferred and the peptide of sequence SEQ ID NO: 47 being particularly preferred, the C peptide has at least the amino acid sequence SEQ ID NO: 127 and at most sequence SEQ ID NO: 128; in particular, the C peptide is chosen from the peptides:
having at least sequence SEQ ID NO: 129 and at most a sequence chosen from sequences SEQ ID NO: 147, SEQ ID NO: 153, SEQ ID NO: 162 and SEQ ID NO: 167,
having at least sequence SEQ ID NO: 130 and at most a sequence chosen from sequences SEQ ID NO: 148 and SEQ ID NO: 150,
having at least sequence SEQ ID NO: 131 and at most sequence SEQ ID NO: 149,
having at least sequence SEQ ID NO: 132 and at most a sequence chosen from sequences SEQ ID NO: 151, SEQ ID NO: 155, SEQ ID NO: 168 and SEQ ID NO: 171,
having at least sequence SEQ ID NO: 133 and at most sequence SEQ ID NO: 152,
having at least sequence SEQ ID NO: 134 and at most a sequence chosen from sequences SEQ ID NO: 154 and SEQ ID NO: 169,
having at least sequence SEQ ID NO: 135 and at most sequence SEQ ID NO: 156,
having at least sequence SEQ ID NO: 136 and at most a sequence chosen from sequences SEQ ID NO: 157 and SEQ ID NO: 170, having at least sequence SEQ ID NO: 137 and at most sequence SEQ ID NO: 158,
having at least sequence SEQ ID NO: 138 and at most sequence SEQ ID NO: 159,
having at least sequence SEQ ID NO: 139 and at most sequence SEQ ID NO: 160,
having at least sequence SEQ ID NO: 140 and at most sequence SEQ ID NO: 161,
having at least sequence SEQ ID NO: 141 and at most sequence SEQ ID NO: 163,
having at least sequence SEQ ID NO: 142 and at most sequence SEQ ID NO: 164,
having at least sequence SEQ ID NO: 143 and at most sequence SEQ ID NO: 165,
having at least sequence SEQ ID NO: 144 and at most sequence SEQ ID NO: 166,
having at least sequence SEQ ID NO: 145 and at most sequence SEQ ID NO: 172, and
having at least sequence SEQ ID NO: 146 and at most sequence SEQ ID NO: 173,
the peptides of sequence SEQ ID NO: 129 to 146 being preferred and the peptide of sequence SEQ ID NO: 129 being particularly preferred, and
the D peptide has at least the amino acid sequence SEQ ID NO: 174 and at most sequence SEQ ID NO: 175; in particular, the D peptide is chosen from the peptides:
having at least sequence SEQ ID NO: 176 and at most a sequence chosen from sequences SEQ ID NO: 188, SEQ ID NO: 192, SEQ ID NO: 193, SEQ ID NO: 194, SEQ ID NO: 201, SEQ ID NO: 202, SEQ ID NO: 203, SEQ ID NO: 204, SEQ ID NO: 205 and SEQ ID NO: 210,
having at least sequence SEQ ID NO: 177 and at most a sequence chosen from sequences SEQ ID NO: 189 and SEQ ID NO: 190,
having at least sequence SEQ ID NO: 178 and at most sequence SEQ ID NO: 191,
having at least sequence SEQ ID NO: 179 and at most sequence SEQ ID NO: 195,
having at least sequence SEQ ID NO: 180 and at most a sequence chosen from sequences SEQ ID NO: 196 and SEQ ID NO: 206,
having at least sequence SEQ ID NO: 181 and at most sequence SEQ ID NO: 197,
having at least sequence SEQ ID NO: 182 and at most a sequence chosen from sequences SEQ ID NO: 198 and SEQ ID NO: 209,
having at least sequence SEQ ID NO: 183 and at most a sequence chosen from sequences SEQ ID NO: 199 and SEQ ID NO: 200,
having at least sequence SEQ ID NO: 184 and at most sequence SEQ ID NO: 207,
having at least sequence SEQ ID NO: 185 and at most sequence SEQ ID NO: 208,
having at least sequence SEQ ID NO: 186 and at most sequence SEQ ID NO: 211, and
having at least sequence SEQ ID NO: 187 and at most sequence SEQ ID NO: 212,
the peptides of sequence SEQ ID NO: 176 to 187 being preferred and the peptide of sequence SEQ ID NO: 176 being particularly preferred.

The expression "the A peptide has at least the amino acid sequence SEQ ID NO: 1 and at most sequence SEQ ID NO: 2" signifies that the N-terminal end is delimited by the amino acid situated at one of positions 1 to 8 of SEQ ID NO: 2 and the C-terminal end is delimited by the amino acid situated at one of positions 38 to 46 of SEQ ID NO: 2.

Thus the A peptide has at least the 31 consecutive amino acids of sequence SEQ ID NO: 1 and at most the 46 consecutive amino acids of sequence SEQ ID NO: 2.

Sequence SEQ ID NO: 2 includes the 31 amino acids of sequence SEQ ID NO: 1.

Thus the A peptide of the invention always has at least the 31 amino acids of sequence SEQ ID NO: 1 and at most 15 additional amino acids distributed on both sides of these 31 amino acids within the limit of sequence SEQ ID NO: 2. For example, an A peptide of the invention can comprise 33 amino acids constituted by 31 amino acids of SEQ ID NO: 1 and either 2 N-terminal amino acids, or 2 C-terminal amino acids, or 1 N-terminal amino acid and a C-terminal amino acid.

The expression "the B peptide has at least the amino acid sequence SEQ ID NO: 45 and at most sequence SEQ ID NO: 46" signifies that the N-terminal end is delimited by the amino acid situated at one of positions 1 to 12 of SEQ ID NO: 46 and the C-terminal end is delimited by the amino acid situated at one of positions 56 to 63 of SEQ ID NO: 46.

Thus the B peptide has at least the 45 consecutive amino acids of sequence SEQ ID NO: 45 and at most the 63 consecutive amino acids of sequence SEQ ID NO: 46.

Sequence SEQ ID NO: 46 includes the 45 amino acids of sequence SEQ ID NO: 45.

Thus the B peptide of the invention always has at least the 45 amino acids of sequence SEQ ID NO: 45 and at most 18 additional amino acids distributed on both sides of these 45 amino acids within the limit of sequence SEQ ID NO: 46.

The expression "the C peptide has at least the amino acid sequence SEQ ID NO: 127 and at most sequence SEQ ID NO: 128" signifies that the N-terminal end is delimited by the amino acid situated at one of positions 1 to 23 of SEQ ID NO: 128 and the C-terminal end is delimited by the amino acid situated at one of positions 54 to 57 of SEQ ID NO: 128.

Thus the C peptide has at least the 32 consecutive amino acids of sequence SEQ ID NO: 127 and at most the 57 consecutive amino acids of sequence SEQ ID NO: 128.

Sequence SEQ ID NO: 128 includes the 32 amino acids of sequence SEQ ID NO: 127.

Thus the C peptide of the invention always has at least the 32 amino acids of sequence SEQ ID NO: 127 and at most 25 additional amino acids distributed on both sides of these 32 amino acids within the limit of sequence SEQ ID NO: 128.

The expression "the D peptide has at least the amino acid sequence SEQ ID NO: 174 and at most sequence SEQ ID NO: 175" signifies that the N-terminal end is delimited by the amino acid situated at one of positions 1 to 4 of SEQ ID NO: 175 and the C-terminal end is delimited by the amino acid situated at one of positions 32 to 44 of SEQ ID NO: 175.

Thus the D peptide has at least the 29 consecutive amino acids of sequence SEQ ID NO: 174 and at most the 44 consecutive amino acids of sequence SEQ ID NO: 175.

Sequence SEQ ID NO: 175 includes the 29 amino acids of sequence SEQ ID NO: 174.

Thus the D peptide of the invention always has at least the 29 amino acids of sequence SEQ ID NO: 174 and at most 15 additional amino acids distributed on both sides of these 29 amino acids within the limit of sequence SEQ ID NO: 175.

The B and C peptides contain novel epitopes having a strong immunogenic power.

Another subject of the invention relates to the B' epitope, contained in the B peptide and situated between positions 1038 and 1047 of the viral polyprotein, which possesses the following amino acid sequence SEQ ID NO: 213: $GX_{18}X_{19}X_{20}X_{21}X_{22}X_{23}TSL$ in which $X_{18}$ is L or V, $X_{19}$ is L or F, $X_{20}$ is G or S, $X_{21}$ is C or T, $X_{22}$ is I or V and $X_{23}$ is I or V.

According to one embodiment of the invention, the B' epitope is chosen from the following epitopes:
the epitope of sequence SEQ ID NO: 214 which corresponds to sequence SEQ ID NO: 213 in which $X_{18}$ is L, $X_{19}$ is L, $X_{20}$ is G, $X_{21}$ is C, $X_{22}$ is I and $X_{23}$ is I,
the epitope of sequence SEQ ID NO: 215 which corresponds to sequence SEQ ID NO: 213 in which $X_{18}$ is L, $X_{19}$ is F, $X_{20}$ is G, $X_{21}$ is C, $X_{22}$ is I and $X_{23}$ is I,
the epitope of sequence SEQ ID NO: 216 which corresponds to sequence SEQ ID NO: 213 in which $X_{18}$ is V, $X_{19}$ is L, $X_{20}$ is G, $X_{21}$ is C, $X_{22}$ is V and $X_{23}$ is I,
the epitope of sequence SEQ ID NO: 217 which corresponds to sequence SEQ ID NO: 213 in which $X_{18}$ is L, $X_{19}$ is V, $X_{20}$ is G, $X_{21}$ is C, $X_{22}$ is I and $X_{23}$ is I,
the epitope of sequence SEQ ID NO: 218 which corresponds to sequence SEQ ID NO: 213 in which $X_{18}$ is L, $X_{19}$ is L, $X_{20}$ is G, $X_{21}$ is C, $X_{22}$ is I and $X_{23}$ is V,
the epitope of sequence SEQ ID NO: 219 which corresponds to sequence SEQ ID NO: 213 in which $X_{18}$ is L, $X_{19}$ is F, $X_{20}$ is G, $X_{21}$ is C, $X_{22}$ is I and $X_{23}$ is V, and
the epitope of sequence SEQ ID NO: 220 which corresponds to sequence SEQ ID NO: 213 in which $X_{18}$ is L, $X_{19}$ is F, $X_{20}$ is S, $X_{21}$ is T, $X_{22}$ is I and $X_{23}$ is I.

Preferably, the B' epitope possesses at least one of the following characteristics:
it has sequence SEQ ID NO: 214 and
it is restricted to HLA-A2.

Another subject of the invention relates to the C' epitope, contained in the C peptide and situated between positions 1789 and 1821 of the viral polyprotein, which possesses the following amino acid sequence SEQ ID NO: 221: $SPLX_{52}X_{53}X_{54}X_{55}TL$
in which $X_{52}$ is T, S or A, $X_{53}$ is T or I, $X_{54}$ is Q, S or G and $X_{55}$ is N, Q, H, S, Y or T.

According to one embodiment of the invention, the C' epitope is chosen from the following epitopes:
the epitope of sequence SEQ ID NO: 222 which corresponds to sequence SEQ ID NO: 221 in which $X_{52}$ is T, $X_{53}$ is T, $X_{54}$ is Q and $X_{55}$ is N,
the epitope of sequence SEQ ID NO: 223 which corresponds to sequence SEQ ID NO: 221 in which $X_{52}$ is T, $X_{53}$ is T, $X_{54}$ is S and $X_{55}$ is Q,
the epitope of sequence SEQ ID NO: 224 which corresponds to sequence SEQ ID NO: 221 in which $X_{52}$ is T, $X_{53}$ is T, $X_{54}$ is G and $X_{55}$ is Q,
the epitope of sequence SEQ ID NO: 225 which corresponds to sequence SEQ ID NO: 221 in which $X_{52}$ is T, $X_{53}$ is T, $X_{54}$ is Q and $X_{55}$ is H,
the epitope of sequence SEQ ID NO: 226 which corresponds to sequence SEQ ID NO: 221 in which $X_{52}$ is T, $X_{53}$ is T, $X_{54}$ is Q and $X_{55}$ is S,
the epitope of sequence SEQ ID NO: 227 which corresponds to sequence SEQ ID NO: 221 in which $X_{52}$ is T, $X_{53}$ is T, $X_{54}$ is Q and $X_{55}$ is Y,
the epitope of sequence SEQ ID NO: 228 which corresponds to sequence SEQ ID NO: 221 in which $X_{52}$ is T, $X_{53}$ is T, $X_{54}$ is Q and $X_{55}$ is T,
the epitope of sequence SEQ ID NO: 229 which corresponds to sequence SEQ ID NO: 221 in which $X_{52}$ is T, $X_{53}$ is I, $X_{54}$ is Q and $X_{55}$ is H,
the epitope of sequence SEQ ID NO: 230 which corresponds to sequence SEQ ID NO: 221 in which $X_{52}$ is S, $X_{53}$ is T, $X_{54}$ is Q and $X_{55}$ is N,
the epitope of sequence SEQ ID NO: 231 which corresponds to sequence SEQ ID NO: 221 in which $X_{52}$ is A, $X_{53}$ is T, $X_{54}$ is Q and $X_{55}$ is Y, and
the epitope of sequence SEQ ID NO: 232 which corresponds to sequence SEQ ID NO: 221 in which $X_{52}$ is T, $X_{53}$ is T, $X_{54}$ is Q and $X_{55}$ is Q.

Preferably, the C' epitope possesses at least one of the following characteristics:
it has sequence SEQ ID NO: 222 and
it is restricted to HLA-B7.

The compositions of the invention, apart from the A to D peptides, can also contain the B' and C' epitopes, which constitutes another subject of the invention.

In a preferred embodiment, the peptide composition of the present invention comprises at least two peptides as defined above which are fused each other.

The present invention also relates to a novel fusion peptide comprising at least two peptides as defined above which are fused each other. The term "fusion" as used herein means that the amino acids of the first peptide and of the second peptide are fused in one polypeptide chain, preferably by in frame fusion of the corresponding coding nucleotide sequences. Advantageously, the fusion peptide of the invention comprises a fusion of at least two peptides chosen from the group consisting of A, B, C, D, B' and C' peptides as defined above, as well as pharmaceutical compositions containing such a fusion peptide and its use in particular as a vaccine, for the preparation of a medicament intended for the inhibition or prevention of an infection caused by the hepatitis C virus, and as a diagnostic composition.

A preferred fusion peptide comprises a fusion of at least four peptides chosen from the group consisting of A, B, C, and D peptides. A more preferred peptide composition comprises a fusion of A to D peptides with B peptide located at the N-terminus which is fused to A peptide which is fused to C peptide which is fused to D peptide (B/A/C/D fusion peptide). In particular, the A peptide comprised in the fusion peptide of the invention has at least SEQ ID NO: 3 and at most SEQ ID NO: 19. Independently or in combination with the other peptides, the B peptide comprised in the fusion peptide of the invention has at least SEQ ID NO: 47 and at most SEQ ID NO: 81. Independently or in combination with the other peptides, the C peptide comprised in the fusion peptide of the invention has at least SEQ ID NO: 129 and at most SEQ ID NO: 147, SEQ ID NO: 153, SEQ ID NO: 162 or SEQ ID NO: 167. Independently or in combination with the other peptides, the D peptide comprised in the fusion peptide of the invention has at least SEQ ID NO: 176 and at most SEQ ID NO: 188, SEQ ID NO: 192, SEQ ID NO: 193 or SEQ ID NO: 194, SEQ ID NO: 201, SEQ ID NO: 202, SEQ ID NO: 203, SEQ ID NO: 204, SEQ ID NO: 205 or SEQ ID NO: 210. In a preferred embodiment, the A peptide comprised in the fusion peptide of the invention has the amino acid sequence defined in SEQ ID NO: 3, the B peptide comprised in the fusion peptide of the invention has the amino acid sequence defined in SEQ ID NO: 47, the C peptide comprised in the fusion peptide of the invention has the amino acid sequence defined in SEQ ID NO: 129 and the D peptide comprised in the fusion peptide of the invention has the amino acid sequence defined in SEQ ID NO: 176. Even more preferably, the fusion peptide of the invention comprises the amino acid sequence defined in SEQ ID NO: 234.

The present invention also relates to the nucleotide sequences coding for any one of the A to D peptides as defined by sequences SEQ ID NO: 1 to 212 and B' and C' epitopes as defined by sequences SEQ ID NO: 213 to 232 and any one of the fusion peptides as defined above, with a special preference for the fusion peptide comprises the amino acid sequence defined by SEQ ID NO: 234.

The peptides of the invention can be obtained by the genetic engineering technique which comprises the stages of:
culture of a microorganism or of eukaryotic cells transformed using a nucleotide sequence according to the invention and
recovery of the peptide produced by said microorganism or said eukaryotic cells.

This technique is well known to a person skilled in the art. For more details concerning this, reference can be made to the following work: Recombinant DNA Technology I, Editors Ales Prokop, Raskesh K Bajpai; Annals of the New York Academy of Sciences, Volume 646, 1991.

The peptides of the invention can also be prepared by the standard peptide syntheses well known to a person skilled in the art.

The nucleotide sequences according to the invention can be prepared by chemical synthesis and genetic engineering using the techniques well known to a person skilled in the art and described for example in Sambrook J. et al., Molecular Cloning: A Laboratory Manual, 1989.

The nucleotide sequences of the invention can be inserted into expression vectors in order to obtain the compositions or peptides of the invention.

Thus, another subject of the invention is the expression vectors comprising a nucleotide sequence of the invention, as well as the means necessary for its expression. Such means necessary for expression are well known in the art and can vary according to the host cell, the expression vector and the level of expression desired.

As expression vectors, there can be mentioned for example the plasmids, the viral vectors of the vaccine virus type, adenovirus, baculovirus, poxvirus, bacterial vectors of *salmonella* type, BCG. Such vectors and methods of using and making them are well known in the art (see for example <<*Nonviral Vectors for gene Therapy*>>, 2001, edited by M. Findeis, Humana Press; <<*Adenoviral Vectors for Gene Therapy*>>, 2002, edited by Curiel and Douglas, Elsevier Science, Academic Press; and <<*Vaccinia Virus and poxvirology*>>, 2004, edited by S. Isaacs, Humana Press). The term "viral vector" as used herein encompasses vector DNA as well as viral particles generated thereof by conventional technologies.

In one embodiment, the vector of the invention is an adenoviral vector. It can be derived from a variety of human or animal sources. Any serotype can be employed from the adenovirus serotypes 1 through 51, with a special preference for human adenoviruses 2 (Ad2), 5 (Ad5), 6 (Ad6), 11 (Ad11), 24 (Ad24) and 35 (Ad35). The cited adenoviruses are available from the American Type Culture Collection (ATCC, Rockville, Md.), and have been the subject of numerous publications describing their sequence, organization and methods of producing, allowing the artisan to apply them (see for example U.S. Pat. No. 6,133,028; U.S. Pat. No. 6,110,735; WO02/40665; WO00/50573; EP 1 016 711; Vogels et al., 2003, J. Virol. 77: 8263-8271). Preferably, the adenoviral vector of the invention is replication-defective (see for example WO94/28152; Lusky et al., 1998, J. Virol 72, 2022-2032). Preferred replication-defective adenoviral vectors are E1-defective with an E1 deletion extending from approximately positions 459 to 3328 or from approximately positions 459 to 3510 (by reference to the sequence of the human adenovirus type 5 disclosed in the GeneBank under the accession number M 73260 and in Chroboczek et al., 1992, Virol. 186, 280-285). The cloning capacity can further be improved by deleting additional portion(s) of the adenoviral genome (all or part of the non essential E3 region or of other essential E2, E4 regions). The nucleotide sequence of the present invention can be inserted in any location of the adenoviral genome. Preferably, it is inserted in replacement of the E1 region. It may be positioned in sense or antisense orientation relative to the natural transcriptional direction of the region in question.

In another embodiment the vector of the invention is derived from a poxvirus. It may be obtained from any member of the poxyiridae, in particular canarypox, fowlpox and vaccinia virus, the latter being preferred. Suitable vaccinia viruses include without limitation the Copenhagen strain (Goebel et al., 1990, Virol. 179: 247-266 and 517-563; Johnson et al., 1993, Virol. 196: 381-401), the Wyeth strain and the modified Ankara (MVA) strain (Antoine et al., 1998, Virol. 244: 365-396). The general conditions for constructing recombinant poxvirus are well known in the art (see for example EP 206 920; Mayr et al., 1975, Infection 3: 6-14; Sutter and Moss, 1992, Proc. Natl. Acad. Sci. USA 89: 10847-10851; U.S. Pat. No. 6,440,422). The nucleotide sequence of the present invention is preferably inserted within the poxyiral genome in a non-essential locus. Thymidine kinase gene is particularly appropriate for insertion in Copenhagen vaccinia vectors (Hruby et al., 1983, Proc. Natl. Acad. Sci. USA 80: 3411-3415; Weir et al., 1983, J. Virol. 46: 530-537) and deletion II or III for insertion in MVA vector (Meyer et al., 1991, J. Gen. Virol. 72: 1031-1038; Sutter et al., 1994, Vaccine 12: 1032-1040).

In another embodiment, the expression vector of the invention can be optionally coupled or complexed to conventional drug delivery systems (e.g. lipid or polymer-based liposomes, nanoparticles, etc. such as those described for example in Mahato et al., 1998, Human Gene Ther. 9: 2083-2099 and Allen et al., 2004, Science 303: 18181822).

By "means necessary for the expression" it is meant any means which make it possible to obtain the peptide or fusion peptide of the invention, such as in particular, a promoter, a transcription terminator, a replication origin and preferably a selection marker.

The promoter used in the context of the invention can be of any origin, e.g. viral, cellular or synthetic and be ubiquitous providing constitutive expression or regulable providing for example specific expression in a particular cell type or under specific conditions. It can further be operably linked to an enhancer. Suitable viral promoters include without limitation early promoters obtained from RSV (Rous Sarcoma Virus), SV40 (Simian Virus), and CMV (Cytomegalovirus; Boshart et al., 1985, Cell 41, 521-530), as well as the TK (Thymidine kinase) promoter of HSV-1 virus (Herpes Virus Simplex-1), the major late adenovirus promoter (MLP) and vaccinia promoters (e.g. 7.5K, HSR, TK, p28, p11 and K1 L promoters). One may use synthetic promoters such as those described in particular by Chakrabarti et al. (1997, Biotechniques 23: 1094-1097), Hammond et al. (1997, J. Virological Methods 66: 135-138). Suitable cellular promoters include any promoter driving expression of cellular genes with a special interest for liver specific promoters such as those of phosphoglycero kinase (PGK; Adra et al., 1987, Gene 60: 65-74), albumin (Pinkert et al., 1987, Genes Dev. 1: 268-277), phosphoenol pyruvate carboxy kinase (PEPCK) (Eisenberger et al., 1992, Mol. Cell. Biol. 12: 1396-1403), cholesterol 7-alpha hydroylase (CYP-7) (Lee et al., 1994, J. Biol. Chem. 269: 14681-14689), alpha-1 antitrypsin (Ciliberto et al., 1985, Cell 41: 531-540), transferrine (Mendelzon et al., 1990, Nucleic Acids Res. 18: 5717-5721); and facteur IX (U.S. Pat. No. 5,814,716) genes.

The vectors of the invention may also comprise one or more additional means in order to improve the transcription rate or level of the nucleotide sequence of the invention in a given host cell, its stability, nuclear RNA transport and/or translation rate or level of the mRNA. Such means are well known by the skilled person and include for example 5', 3' non-coding sequences, intervening sequences, splicing sequences, Shine-Dalgarno sequence, Kozak sequence and initiator methionine.

The vectors of the invention can also comprise sequences necessary for the screening of the peptides towards particular cell compartments. An example of screening can be screening towards the endoplasmic reticulum obtained using orientation sequences of the type of the leader sequence originating from the protein E3 of the adenovirus (Ciernik I. F., et al., The Journal of Immunology, 1999, 162: 3915-3925).

The expression vectors of the invention can comprise either a single nucleotide sequence coding for any one of the peptides of the invention, or at least two nucleotide sequences, it being understood that each nucleotide sequence codes for a peptide of different type.

According to one embodiment of the invention, the expression vectors include two nucleotide sequences coding for the A and B, A and C, A and D, B and C, B and D, or D and C peptides.

Preferably, the expression vectors include two nucleotide sequences coding for the A and B, A and C, B and D, or C and D peptides, the vectors comprising two sequences coding for the A and B, C and D, and B and D peptides being particularly preferred.

According to another embodiment, the expression vectors include three nucleotide sequences coding for the A, B and C, A, B and D, A, C and D, or B, C and D peptides.

According to yet another method, the expression vectors include four nucleotide sequences coding for the A to D peptides.

Preferably, the vectors include three nucleotide sequences coding for the A, B and C, A, C and D, and B, C and D peptides. More preferably, the vectors include four nucleotide sequences coding for the A, B, C, and D peptides. In this case, the order of the nucleotide sequences is relatively unimportant, as in the preceding combinations, such that the following combinations, given relative to the peptides, are comprised within the scope of the invention: A/B/C/D, A/B/D/C, A/C/B/D, A/C/D/B, A/D/B/C, A/D/C/B, B/A/C/D, B/A/D/C, B/C/A/D, B/C/D/A, B/D/A/C, B/D/C/A, C/A/B/D, C/A/DB, C/B/A/D, C/B/D/A, C/D/A/B, C/D/B/A, D/A/B/C, D/A/C/B, DB/A/C, D/B/C/A, D/C/A/B and D/C/B/A. The more preferred combination is B/A/C/D, and especially the B/A/C/D fusion peptide previously defined.

The expression vectors of the invention can also comprise at least one nucleotide sequence coding for any one of the B' and C' epitopes as defined previously, which constitutes another embodiment of the invention.

Thus, the vectors of the invention can comprise for example:
  a nucleotide sequence coding for one of the following epitopes: B' and C',
  two nucleotide sequences coding for the B' and C' epitopes or
  several repetitive sequences coding for the B' epitope, the C' epitope or both.

The vectors of the invention can also comprise from two to four nucleotide sequences chosen from the sequences coding for the A, B, C, D peptides and the B' and C' epitopes, it being understood that:
  the nucleotide sequence coding for the B peptide and the nucleotide sequence coding for the B' epitope are not present at the same time, and
  the nucleotide sequence coding for the C peptide and the nucleotide sequence coding for the C' epitope are not present at the same time.

Thus, for example, the vectors of the invention can comprise the following combinations, given relative to said peptides and epitopes: A/B', A/C', A'/D, B/C', B'/C, B'/D, C'/D, A/B'/C, A/B'/C', A/B/C', A/B'/D, A/C'/D, B'/C/D, B/C'/D, B'/C'/D, A/B'/C/D, A/B/C'/D and A/B'/C'/D.

Of course, as previously, the order of the nucleotide sequences in the expression vectors is relatively unimportant.

When the expression vectors of the invention include several nucleotide sequences, said sequences can be linked to each other directly, or via spacing or binding agents which are typically made up of small neutral molecules such as amino acids or amino acid mimetics which typically have a neutral charge under physiological conditions. Direct linkage of the peptide-encoding nucleotide sequences each other in a fusion peptide is preferred in the context of the invention.

In a preferred embodiment of the invention, the at least two nucleotide sequences are linked in the same reading frame. The expression "linked in the same reading frame" implies that in said reading frame, there is no stop codon between said two nucleotide sequences.

As spacing agents, there can be mentioned the Ala, Gly residues or other neutral spacing agents of non-polar amino acids or neutral polar amino acids.

These amino acid spacers have at least one or two residues and usually from 3 to 6 residues.

A subject of the invention is also the microorganisms and eukaryotic cells transformed by an expression vector of the invention. In the context of the invention, the term "transformation" or "transformed" has to be understood as meaning "introduction" or "introduced" in a host cell. Any routine method can be used in the art to "transform" a nucleotide sequence or a vector in a host cell, e.g. a microorganism or eukaryotic cell.

Such methods include, but are not limited to, microinjection (Capechi et al., 1980, Cell 22, 479-488), $CaPO_4$-mediated transfection (Chen and Okayama, 1987, Mol. Cell. Biol. 7, 2745-2752), DEAE-dextran-mediated transfection, electroporation (Chu et al., 1987, Nucleic Acid Res. 15: 1311-1326), lipofection/liposome fusion (Feigner et al., 1987, Proc. Natl. Acad. Sci. USA 84: 7413-7417), particle bombardement (Yang et al., 1990, Proc. Natl. Acad. Sci. USA 87: 9568-9572), gene guns, transduction as well as viral infection. For example, in the context of the invention, a viral vector can be transformed in the host cell by transfection of its genome or by infection of a viral particle. The term "host cell" should be understood broadly without any limitation concerning microorganisms and eukaryotic cells including isolated cells or cells organized in particular structures such as tissues and organs. The host cells may be of a unique type of cells or a group of different types of cells and encompass cultured cell lines, primary cells and proliferative cells.

When a composition of the invention containing at least two A to D peptides of the invention is to be obtained, the microorganisms or eukaryotic cells are transformed by an expression vector containing at least two nucleotide sequences, or they are cotransformed by at least two expression vectors containing a single nucleotide sequence, each vector coding for a peptide of different type.

According to one embodiment of the invention, the microorganisms and eukaryotic cells are cotransformed with:

two vectors coding respectively for the A and B, A and C, A and D, B and C, B and D, or C and D peptides, three vectors coding respectively for the A, B and C, A, B and D, A, C and D, or B, C and D peptides, or four vectors coding respectively for the A, B, C and D peptides.

Similarly, when a composition of the invention is to be obtained containing at least two B' and C' epitopes, or at least one B' or C' epitope and at least one A to D peptide, the microorganisms or eukaryotic cells are transformed by a single vector coding for the desired combination of epitopes or epitopes/peptides or by several vectors each coding for each constituent of the desired combination.

As examples of microorganisms which are appropriate for the purposes of the invention, there can be mentioned yeasts, such as those of the following families: *Saccharomyces, Schizosaccharomyces, Kluveromyces, Pichia, Hanseluna, Yarowia, Schwaniomyces, Zygosaccharomyces, Saccharomyces cerevisiae, Saccharomyces carlsbergensis* and *Kluveromyces* lactis being preferred; and bacteria, such as *E. coli* and those of the following families: *Lactobacillus, Lactococcus, Salmonella, Streptococcus, Bacillus* and *Streptomyces*.

As examples of eukaryotic cells, there can be mentioned cells originating from animals such as mammals, reptiles, insects and equivalent. The preferred eukaryotic cells are cells originating from the Chinese hamster (CHO cells), monkey (COS and Vero cells), baby hamster kidney (BHK cells), pig kidney (PK 15 cells) and rabbit kidney (RK13 cells), human osteosarcoma cell lines (143 B cells), human HeLa cell lines and human hepatoma cell lines (Hep G2 cell type), as well as insect cell lines (for example of *Spodoptera frugiperda*).

The host cells can be supplied in cultures in suspension or in vials, in tissue cultures, organ cultures and equivalent. The host cells can also be from transgenic animals. Host cells of the present invention can be cultured in conventional fermentation bioreactors, flasks, and petri plates. Culturing can be carried out at a temperature, pH and oxygen content appropriate for a given host cell. No attempts to describe in detail the various methods known for the production of polypeptides in microorganisms and eukaryote cells will be made here.

The peptides and fusion peptides of the invention can be purified from the producing host cells by well-known purification methods including ammonium sulfate precipitation, acid extraction, gel electrophoresis, filtration and chromatographic methods (e.g. reverse phase, size exclusion, ion exchange, affinity, phosphocellulose, hydrophobic-interaction, hydroxylapatite, or high performance liquid chromatography). The conditions and technology used to purify a particular peptide or fusion peptide of the invention will depend on factors such as net charge, molecular weight, hydrophobicity, hydrophilicity and will be apparent to those having skill in the art. Moreover, the level of purification will depend on the intended use.

The invention also relates to antibodies directed against one of the abovementioned peptides of the invention or against one of the peptide compositions of the invention as defined previously, or also against one of the epitopes of the invention.

The antibodies according to the invention are either polyclonal or monoclonal antibodies.

The abovementioned polyclonal antibodies can be obtained by immunization of an animal with at least one viral antigen of interest, followed by the recovery of the sought antibodies in purified form, by taking a sample of the serum of said animal, and separation of said antibodies from the other constituents of the serum, in particular by affinity chromatography on a column on which an antigen specifically recognized by the antibodies, in particular a viral antigen of interest, is fixed.

The monoclonal antibodies can be obtained by the hybridoma technique, the general principle of which is recalled hereafter.

Firstly, an animal, generally a mouse, (or cells in culture within the framework of in vitro immunizations) is immunized with a viral antigen of interest, the B lymphocytes of which are then capable of producing antibodies against said antigen. These antibody-producing lymphocytes are then fused with "immortal" myelomatous cells (murine in the example) in order to produce hybridomas. From the heterogeneous mixture of the cells thus obtained, a selection is then made of cells capable of producing a particular antibody and multiplying indefinitely. Each hybridoma is multiplied in clone form, each leading to the production of a monoclonal antibody the recognition properties of which vis-à-vis the viral antigen of interest can be tested for example in ELISA, by immunotransfer in one or two dimensions, in immunofluorescence, or using a biocaptor. The monoclonal antibodies thus selected are subsequently purified in particular according to the affinity chromatography technique described above.

The compositions of the invention, containing at least two A to D peptides or at least one of the B' and C' epitopes or a fusion peptide as described previously, are particularly effective for the inhibition, prevention and treatment of the virus or infection of patients carrying the virus belonging more particularly to the genotypes 1a, 1b and 4, in such a manner that its use for the preparation of a medicament constitutes another subject of the invention.

The present invention also relates to a pharmaceutical composition, in particular a vaccine, containing as active ingredient at least two different peptides chosen from the A to D peptides as defined previously, or at least two nucleotide sequences as described previously, placed under the control of elements necessary for a constitutive and/or inducible expression of said peptides, or at least one of the antibodies as defined previously, or also at least one of the B' and C' epitopes as defined previously, or at least one of their nucleotide sequences, in combination with a pharmaceutically appropriate vehicle.

The present invention also relates to a pharmaceutical composition, in particular vaccine, containing as active ingredient at least a fusion peptide as defined previously or at least a nucleotide sequence or a vector or a host cell as defined previously encoding the fusion peptide of the invention, placed under the control of the elements necessary for a constitutive and/or inducible expression of said fusion peptide in a given host cell, in combination with a pharmaceutically appropriate vehicle.

By elements necessary for a constitutive expression of the peptides/fusion peptide, is meant a ubiquitous or specific promoter of the eukaryotic cells as previously described.

As elements necessary for an inducible expression of the peptides, there can be mentioned the elements of regulation of the operon of *E. coli* for resistance to tetracycline (Gossen M. and al, Proc Natl Acad Sci USA, 89: 5547-5551 (1992).

Of course, a person skilled in the art will easily determine the pharmaceutically appropriate vehicle and the quantity of active ingredient to be used as a function of the constituents of the pharmaceutical composition. Preferably, the composition of the invention contains the active ingredient or a combination of active ingredients at a dose sufficient for the alleviation of one or more symptoms normally associated with the disease or condition desired to be treated. When prophylactic use is concerned, this means a dose sufficient to prevent or to delay the establishment of a chronic HCV infection. For example, the active ingredient or a combination thereof is preferably contained in the composition of the invention at a dose sufficient for inducing a specific immune response in the treated host (e.g. resulting in the development of an anti-HCV response, whether humoral or cellular or both, with a special preference for a cytolytic T cell response).

The appropriate dosage can be adapted as a function of various parameters, in particular the mode of administration; the composition employed; the age, health, and weight of the patient to be treated; the nature and extent of symptoms; kind of concurrent treatment; the frequency of treatment; and/or the need for prevention or therapy. Further refinement of the calculations necessary to determine the appropriate dosage for treatment is routinely made by a practitioner, in the light of the relevant circumstances. For general guidance, suitable dosage for a virus-comprising composition (e.g. vaccinia or adenovirus particles) varies from about $10^5$ to $10^{13}$ iu (infectious units), desirably from about $10^6$ and $10^{12}$ iu. A composition based on vector plasmids may be administered in doses of between 10 μg and 20 mg, advantageously between 100 μg and 2 mg. A peptide composition may be administered in one or more doses of between 10 ng and 20 mg, with a special preference for a dosage from about 0.1 μg to about 2 mg of peptide(s) per kg body weight. The administration may take place in a single dose or a dose repeated one or several times after a certain time interval.

As used herein, a "pharmaceutically appropriate vehicle" is intended to include any and all carriers, solvents, diluents, excipients, adjuvants, dispersion media, coatings, antibacterial and antifungal agents, and absorption delaying agents compatible with pharmaceutical administration. The composition of the invention can be in various forms, e.g. solid, liquid or frozen. Solid (e.g. dry powdered or lyophilized) compositions can be obtained by a process involving vacuum drying and freeze-drying.

Suitably, the pharmaceutical composition of the invention comprises a diluent appropriate for human or animal use. It is preferably isotonic, hypotonic or weakly hypertonic and has a relatively low ionic strength. Representative examples include sterile water, physiological saline (e.g. sodium chloride), Ringer's solution, glucose, trehalose or saccharose solutions, Hank's solution, and other aqueous physiologically balanced salt solutions (see for example the most current edition of Remington: The Science and Practice of Pharmacy, A. Gennaro, Lippincott, Williams&Wilkins). The composition of the invention is suitably buffered in order to be appropriate for human use at a physiological or slightly basic pH (e.g. between about pH 7 to about pH 9). Suitable buffers include without limitation phosphate buffer (e.g. PBS), bicarbonate buffer and/or Tris buffer.

The pharmaceutically appropriate vehicles included in the composition of the invention must also permit to preserve its stability under the conditions of manufacture and long-term storage (i.e. at least one month) at freezing (e.g. −70° C., −20° C.), refrigerated (e.g. 4° C.) or ambient temperatures. In this respect, formulations which are particularly adapted to the composition of the invention include:

1M saccharose, 150 mM NaCl, 1 mM $MgCl_2$, 54 mg/l Tween 80, 10 mM Tris pH 8.5 (especially when the active ingredient is an adenoviral vector),
10 mg/ml mannitol, 1 mg/ml HSA, 20 mM Tris, pH 7.2, and 150 mM NaCl, and
physiological saline.

In addition, the composition of the invention may comprise one or more adjuvant(s) suitable for systemic or mucosal application in humans. Preferably, the adjuvant is capable of stimulating immunity to the composition of the invention, especially a T cell-mediated immunity e.g. through the toll-like receptors (TLR). Suitable adjuvants are well known in the art. Representative examples include without limitation alum, mineral oil emulsion such as Freunds complete and incomplete (IFA), lipopolysaccharide (Ribi et al., 1986, Immunology and Immunopharmacology of Bacterial Endotoxins, Plenum Publ. Corp., NY, p407-419), saponins (Sumino et al., 1998, J. Virol. 72, 4931-4939; WO 98/56415), imidazo-quinoline compounds (Suader, 2000, J. Am. Acad Dermatol. 43, S6-S11; Smorlesi, 2005, Gene Ther. 12, 1324-1332), and cationic peptides (Kritsch et al., 2005, J. Chromatogr Anal. Technol Biomed Life Sci 822, 263-270).

The composition of the present invention may be administered by a variety of modes of administration, including systemic, topical and localized administration. Injection can be performed by any means, for example by subcutaneous, intradermal, intramuscular, intravenous, intraperitoneal, intratumoral, intravascular, intraarterial injection or by direct injection into an artery (e.g. by hepatic artery infusion) or a vein feeding liver (e.g. injection into the portal vein). Injections can be made with conventional syringes and needles, or any other appropriate devices available in the art. Topical administration can also be performed using transdermal means (e.g. patch and the like). Administration via mucosal route can also be envisaged (e.g. intranasal, intravaginal). In the context of the invention, intramuscular and subcutaneous administrations constitute the preferred routes.

The pharmaceutical composition of the invention may be employed in methods for treating a variety of diseases and pathologic conditions, especially those associated with an HCV infection. As used herein, the term "treatment" or "treating" encompasses prophylaxis and/or therapy. It is especially useful for treating HCV persistent infection and liver cancer in HCV-infected patients. The term "cancer" encompasses any cancerous conditions including diffuse or localized tumors, metastasis, cancerous polyps as well as preneoplastic lesions (e.g. cirrhosis). Preferably, upon introduction into a host organism according to the modalities described herein, the composition of the invention provides a therapeutic benefit to the treated host. The term "host organism" is intended to encompass mammals including humans infected with HCV. The therapeutic benefit can be evidenced by a number of ways, for instance a decrease of HCV viremia detected in blood, plasma or sera of an infected mammal as compared to before treatment, and/or by the detection of an anti-HCV immune response (e.g. production of anti-HCV antibodies and/or T cell-mediated immunity) and/or by a modification of the proteomic profile analyzed before and after therapy (e.g. using the Gene Array Affimetrix technology on blood cells) and/or by the delay of the symptoms associated with an HCV infection (e.g. delay in the development of liver cirrhosis or cancer), and/or by a decrease of liver inflammation/steatosis/fibrosis conditions typically associated with HCV infection or by an improved response of the mammal to conventional therapies.

The invention also relates to a diagnostic composition for the detection and/or quantification of the hepatitis C virus comprising at least two different peptides chosen from the A to D peptides as defined previously, or at least one B' or C' epitope as defined previously, or at least one antibody as defined previously.

There also, a person skilled in the art will easily determine the quantity of peptides to be used as a function of the diagnostic technique used.

The invention also relates to a process for detection and/or quantification of the hepatitis C virus in a biological sample taken from an individual capable of being infected by said virus, such as plasma, serum or tissue, characterized in that it comprises stages consisting of:

bringing said biological sample into contact with at least one of the antibodies of the invention under conditions allowing the formation of a complex between the virus and the antibody, detecting and/or quantifying the formation of said complex by any appropriate means.

The processes of detection and/or quantification of the virus are implemented using standard techniques well known to a person skilled in the art and there can be mentioned, by way of illustration, blots, so-called sandwich techniques, competition techniques and PCR detection techniques, in particular so-called "real-time" techniques.

The invention also relates to the use of the compositions of the invention for the in vitro diagnosis of the hepatitis C virus in a biological sample.

Finally, the invention relates to the use of the compositions of the invention for the preparation of a vaccine composition.

In a preferred embodiment, the present invention relates to the use of the peptide composition, fusion peptide, nucleotide sequence, vector, host cell or pharmaceutical composition of the invention for the preparation of a drug intended for inhibiting or treating or preventing HCV infections, HCV-associated diseases and pathologic conditions, in an animal, preferably human, according to the modalities described above.

The present invention also provides a method for the treatment or prevention of a human or animal organism, comprising administering to said organism a therapeutically effective amount of the peptide composition, fusion peptide, nucleotide sequence, vector, host cell or pharmaceutical composition of the invention. If desired, the method of the invention can be carried out in conjunction with one or more conventional therapeutic modalities (e.g. radiation, chemotherapy antiviral treatment and/or surgery). The use of multiple therapeutic approaches provides the patient with a broader based intervention.

The method or use of the invention may be carried out according to a prime boost therapeutic modality which comprises sequential administration of one or more primer composition(s) and one or more booster composition(s). Typically, the priming and the boosting compositions use different vehicles which comprise or encode at least an antigenic domain in common. In the context of the invention, a composition of the invention may be used to either prime or boost or both prime and boost an anti-HCV immune response. For illustrative purposes, one may prime with a fusion peptide having the amino acid sequence shown in SEQ ID NO: 234 and boost with a vector encoding an antigenic domain in common with the composition of the invention (e.g. an antigenic domain of NS3, NS4 and/or NS5B polypeptide). The source of such material is wide and includes without limitation peptides, proteins, viral vector from a variety of viruses, plasmid DNA, proteinaceous particles such as virus-like particles (Burns et al., 1994, Mol. Biol. Techno. 1: 137-145), cellular materials such as irradiated cells, virus particles (e.g. as described in WO2004/111082), etc. Alternatively, one may prime with the adenovirus particles of WO2004/111082 and subsequently boost with a MVA vector encoding the fusion peptide as defined in SEQ ID NO: 234. However other prime boost combinations are also possible in the context of the invention.

The present invention also provides a method of inducing or stimulating an immune response against HCV in a host organism comprising administering to said organism the peptide composition, fusion peptide, nucleotide sequence, vector, host cell, antibodies or pharmaceutical composition of the invention so as to induce or stimulate said immune response. The immune response can be a specific and/or a nonspecific, a humoral and/or a cell-mediated response. The immune response is preferably a T cell-mediated response directed to a T cell-recognized HCV epitope. The ability of the method of the invention to induce or stimulate an anti-HCV immune response upon administration in an animal or human organism can be evaluated either in vitro or in vivo using a variety of assays which are standard in the art (see for example Coligan et al., 1992 and 1994, Current Protocols in Immunology; ed J Wiley & Sons Inc, National Institute of Health). Measurement of cellular immunity can be performed by measurement of cytokine profiles secreted by activated effector cells including those derived from CD4+ and CD8+ T-cells (e.g. quantification of IL-10 or IFNg-producing cells by ELl-spot), by determination of the activation status of immune effector cells (e.g. T cell proliferation assays by a classical [$^3$H] thymidine uptake), by assaying for antigen-specific T lymphocytes in a sensitized subject (e.g. peptide-specific lysis in a cytotoxicity assay). The ability to stimulate a humoral response may be determined by antibody binding and/or competition in binding (see for example Harlow, 1989, Antibodies, Cold Spring Harbor Press). The method of the invention can also be further validated in animal models challenged with an appropriate infectious or tumor-inducing agent (e.g. surrogate murine challenge assays described in the art using for example a recombinant *Listeria* expressing NS3, a NS2-NS5 vaccinia virus) to determine neutralization of the infectious or tumor-inducing agent and eventually partial resistance to the associated symptoms, reflecting an induction or an enhancement of an anti-HCV immune response. Testing and validation of the compositions of the invention are also illustrated in the appended Example section.

The invention has been described in an illustrative manner, and it is to be understood that the terminology which has been used is intended to be in the nature of words of description rather than of limitation. Obviously, many modifications and variations of the present invention are possible in light of the above teachings. It is therefore to be understood that within the scope of the appended claims, the invention may be practiced in a different way from what is specifically described herein.

All of the above cited disclosures of patents, publications and database entries are specifically incorporated herein by reference in their entirety to the same extent as if each such individual patent, publication or entry were specifically and individually indicated to be incorporated by reference.

The present invention will be better understood using the following examples given only by way of illustration and non-limitatively, as well as using the attached FIGS. 1 to 16, in which:

FIG. 1A represents the average production of gamma interferon for 3 patients (Pt 1 to 3) infected by HCV strains of genotype 1 and having an HLA. A2+. This production is determined by the number of spots observed per million of blood cells brought into contact with the FLAT (FLATCVNGV SEQ ID NO:238) and LLG (LLGCIITSL SEQ ID NO:239) peptides, FIG. 1B represents the average production of interleukin-10 for 3 patients (Pt 1 to 3) infected by HCV strains of genotype 1 and having an HLA. A2+. This production is determined by the number of spots observed per million of blood cells brought into contact with the FLAT and LLG peptides, FIG. 2 represents the alignment of the A peptides of the invention (SEQ ID NO:19), FIG. 3 represents the alignment of the B peptides of the invention (SEQ ID NO:81), FIG. 4 represents the alignment of the C peptides of the invention (SEQ ID NO:147); and FIG. 5 represents the alignment of the D peptides of the invention (SEQ ID NO:188).

FIG. 6 relates to the A peptide and shows a graph giving the specific lysis percentage of splenocytes of HLA-A2 transgenic mice according to the CTL test conditions after immunization of the mice by the A peptide of the invention, FIGS. 7A and 7B relate to the B peptide and show on the one hand a graph giving the specific lysis percentage of splenocytes of HLA-A2 transgenic mice according to the conditions of the CTL test after immunization of the mice by the B peptide of the invention (FIG. 7A) and on the other hand another graph giving the number of gamma-interferon-producing cells revealed by the ELISPOT method originating from the same transgenic mice and brought into contact with the ATL epitope of the prior art contained in the A peptide (FIG. 7B), FIGS. 8A and 8B relate to the C peptide and show on the one hand a graph giving the specific lysis percentage of splenocytes of HLA-A2 transgenic mice according to the CTL test conditions after immunization of the mice by the C peptide of the invention (FIG. 8A) and on the other hand another graph giving the number of gamma-interferon-producing cells revealed by the ELISPOT method originating from the same transgenic mice and brought into contact with the C peptide (FIG. 8B), FIGS. 9A and 9B relate to the D peptide and show on the one hand a graph giving the specific lysis percentage of splenocytes of HLA-A2 transgenic mice according to the CTL test conditions after immunization of the mice by the D peptide of the invention (FIG. 9A) and on the other hand another graph giving the number of gamma-interferon-producing cells revealed by the ELISPOT method originating from the same transgenic mice and brought into contact with the epitope ALY of the prior art contained in the D peptide (FIG. 9C), and FIG. 10 is a graph giving the specific lysis percentage of splenocytes of HLA-A2 transgenic mice according to the CTL test conditions after immunization of the mice by the D peptide of the invention or after immunization with the ALY epitope, FIG. 11 is a graph representing the number of gamma-interferon-producing cells revealed by the ELISPOT method originating from an HCV-seropositive patient and brought into contact with the A, B, C and D peptides, as well as with the compositions A/B, B/C/D and A/B/C/D, FIG. 12 is a graph representing the number of gamma-interferon-producing cells revealed by the ELISPOT method originating from another HCV-seropositive patient and brought into contact with the A, B, C and D peptides, as well as with the compositions A/B, A/C, C/D, A/B/C, A/C/D, B/C/D and A/B/C/D, FIG. 13 is a graph representing the number of gamma-interferon-producing cells revealed by the ELISPOT method originating from another HCV-seropositive patient and brought into contact with the A, B, C and D peptides, as well as with the composition A/B/C/D, FIG. 14 is a graph representing the number of gamma-interferon-producing cells revealed by the ELISPOT method originating from another HCV-seropositive patient and brought into contact with the A, B, C and D peptides, as well as with the compositions AB, B/D, B/C/D and A/B/C/D.

FIGS. 15A and 15B illustrate the number of gamma-interferon-producing cells revealed by ELISPOT of splenocytes collected from HLA-A2 transgenic mice immunized with DNA plasmids encoding the B/A/C/D fusion peptide of the invention (FIG. 15A) or immunized with adenoviruses encoding the B/A/C/D fusion peptide of the invention (FIG. 15B) using the indicated peptides (GLL, ALY and CVN). Striped histograms represent polyEp-WT-expressing vectors, black histograms represent polyEp-C-expressing vectors, stippled histograms represent polyEp-E3-expressing vectors and white histograms represent empty vectors. In FIG. 15A, WT, C, E3 and Φ represent mice immunized with gwiz plasmids encoding polyEp-WT, polyEp-C, polyEp-E3 and with an empty gwiz plasmid whereas in FIG. 15B, WT, C, E3 and Φ represent mice immunized with Ad-polyEp-WT, Ad-polyEp-C, Ad-polyEp-E3 and with an empty adenovirus vector respectively FIGS. 16A and 16B illustrate the specific lysis percentage revealed by CTL assay of splenocytes collected from HLA-A2 transgenic mice immunized with gwiz plasmids encoding polyEp-WT, Ad-polyEp-C, Ad-polyEp-E3 encoding the B/A/C/D fusion peptide of the invention (FIG. 16A) or immunized with Ad-polyEp-WT, Ad-polyEp-C and Ad-polyEp-E3 (FIG. 16B). Striped histograms represent polyEp-WT-expressing vectors, black histograms represent polyEp-C-expressing vectors, stippled histograms represent polyEp-E3-expressing vectors and white histograms represent empty vectors. Tested peptides are indicated under each graph. Effector/Target (E/T) ratio is 100/1 except for CVN and GLL peptides where the E/T ratio is 4/1.

EXAMPLE 1

Absence of Correlation Between the Binding Score and the Immunogenic Power of a Peptide-Epitope 1a: Test on Human Cells The ability of blood cells from 3 patients infected by the hepatitis C virus of genotype 1 and having an HLA of type HLA-A2+ to produce gamma-interferon cytokines and interleukin-10, in response to two peptides predicted by software developed by bioMerieux (Centre d'Immunologie de Pierre Fabre) to bind to the HLA-A2 molecule was tested.

The assay of these cytokines reflects the ability of the peptides to induce immune responses to cell mediation, either of type 1 (gamma interferon), or of type 2 (interleukin-10)

In order to do this, the FLAT (FLATCVNGV SEQ ID NO:238) and LLG (LLGCIITSL SEQ ID NO:239) epitopes included in the B peptide of the invention, which have equivalent binding scores (694 for FLAT and 619 for LLG) were used.

Mononucleated blood cells from 3 infected patients (200, 000 cells per well) were incubated in an ELISPOT plate (Human IL10 Elispot Set, San Diego, Calif., USA) on which biotinylated antibodies specific to gamma interferon (BD kit) or interleukin-10 (purified mouse anti-human γ-IFN monoclonal antibody, BD, No. 554548) had been previously fixed, in the presence of the FLAT and LLG peptides.

After 48 hours of incubation at 37° C., a period during which the cells specific to the peptides will locally produce cytokines which will bind to the specific antibodies, anti-gamma interferon or anti-interleukin-10 antibodies, alkaline phosphatase coupled to avidine and the alkaline phosphatase substrate (NBT/BCIP) were added.

The violet-blue spots, which represent each gamma-interferon or interleukin-10-producing cell were counted, using Zeiss's ELISPOT automated reader (KS Elispot) and only considered positive when the number of spots per well was greater than 20.

The results obtained are shown FIG. 1, in which Pt represents patient. They show that, despite an equivalent binding score on the HLA-A2 molecule, these two peptides do not induce equivalent responses.

In fact, the FLAT peptide induces little if any production of the two cytokines in the three patients, whereas the LLG peptide induces a significant production of gamma interferon in 2 of the 3 patients and of interleukin-10 in the three patients.

The results obtained also show that the peptides of the invention, as well as their combination was not evident with regard to the teachings of the prior art.

1b: Test on Murine Cells

Mice transgenic for the molecule HLA.A2.1 and devoid of murine class 1 molecules (Pascolo S., et al., 1997, J. Exp Med., 185: 2043-2051) were immunized with the FLL and ILA epitopes predicted as being class I epitopes restricted by the molecule HLA.A2.1. The FLL peptide has an average score (515) whereas the ILA peptide has a very high score (893).

In order to do this, the mice were immunized in the base of their tails with a peptide mixture containing one of the above epitopes (60 µM) and the T-helper peptide (Lone, Y. C. et al., (1998), J. Immunother. 21:283-294) (60 µM) emulsified in incomplete Freund's adjuvant (Sigma St Louis, Mo.). The mice received two injections with an interval of two weeks and the immune responses were analyzed two weeks after the last immunization as indicated in Example 1 (Elispot).

The results are shown in Table 1 below.

TABLE 1

| Epitope | Viral antigen | Score | Number of spots/ $10^6$ cells[1]* |
|---|---|---|---|
| FLLLADARV SEQ ID NO: 240 | E2 | 515 | 333; 215; 622 |
| ILAGYAGAGV SEQ ID NO: 241 | NS4 | 893 | 5; 2; 0 |

[1]Gamma-interferon-producing cells
*Number of spots for three individual mice tested.

These results show that the score ascribed to a peptide does not reflect its immunogenicity.

EXAMPLE 2

Demonstration of the Immunogenicity of the Peptides/Peptide Compositions/Epitopes of the Invention in Mice HLA-A2.1-transgenic mice were immunized either with the A peptide of sequence SEQ ID NO: 3, or with the B peptide of sequence SEQ ID NO: 47, or with the C peptide of sequence SEQ ID NO: 129, or with the D peptide of sequence SEQ ID NO: 176, or with the B' epitope of sequence SEQ ID NO: 214 or with the ATL and ALY epitopes of the prior art contained respectively in the A and D peptides (ATLGF-GAYM SEQ ID NO:242, amino acids 1260-1268 of the viral polyprotein and ALYDVVSTL SEQ ID NO:243, amino acids 2594-2602 of the viral polyprotein).

In order to do this, 2 sub-cutaneous injections were administered into the base of the tail of each mouse, with an interval of 15 days, of a mixture containing 18 nmoles of peptide of the invention and 18 nmoles of the HBV core helper peptide in incomplete Freund's adjuvant (IFA, Brinster et al., Hepatology 2001) or containing 60 nmoles of epitope of the invention and 60 nmoles of the helper peptide in IFA.

The control mice received only the helper peptide in IFA.

Fifteen days after the 2nd injection, the cell response was analyzed by isolating the spleen cells (splenocytes) of mice and a CTL test and an ELISPOT test were carried out as follows:

For the CTL test, these splenocytes were cultured in 24-well plates in the presence of 5 µM of the peptide or epitope of interest and 10 U of recombinant murine interleukin-2 (Brinster et al., Hepatology 2001) per ml in alpha minimum essential medium (αMEM) for 5 days. On the 5th day, the restimulation stage was carried out, consisting of adding to the splenocytes in culture splenocytes of naïve mice in the presence of the peptide or epitope of interest over 2 days. On the 7th day, the CTL test itself was carried out, consisting of bringing together the splenocytes of the immunized mice after the 7 days of culture (effective cells) and EL4 S3-Rob HDD cells charged with 10 µM of the peptide or epitope of interest marked with $Cr^{51}$ (target cells). The specific cytotoxic activity of the effective cells was determined by measuring, after 4 hours of incubation with the target cells, the $Cr^{51}$ released following the lysis of the target cells using a γ-Cobra II (Packard, Rungis, France) counting device. The spontaneous and maximum release from wells containing either the medium alone, or the lysis buffer (HCl 1N) were determined. The specific percentage of cytotoxicity was calculated by the formula:

(release in the test−spontaneous release)/(maximum release−spontaneous release)×100.

The peptide or epitope-specific lysis was determined by the difference between the percentage of specific lysis obtained in the presence or absence of the peptide or epitope.

The ELISPOT test was carried out by culturing the splenocytes for 48 hours in Multiscreen (Millipore) 96-well plates previously coated with anti-γ-interferon (γIFN) antibodies (10 µg/ml final). The splenocytes were cultured in the presence of 10 µM of peptide or epitope of interest and 10 U of recombinant murine interleukin-2 per ml in aMEM. For the positive control, the splenocytes were cultured in the presence of concanavalin A (5 µg/ml). For the negative control, the splenocytes were cultured either in the presence of a non-specific peptide belonging to the HCV capsid protein, of sequence DLMGYIPLV SEQ ID NO:244 (also called irrelevant peptide), or in medium alone without peptide or epitope of interest. The wells were washed three times, respectively with PBS-Tween 0.05% then PBS, an operation followed by incubation for 2 hours with biotinylated anti-γ-IFN antibodies of mice. After washing, the wells were incubated for 1 hour with a streptavidin-horseradish peroxidase conjugate and the enzymatic activity was revealed by degradation of the AEC (aminoethylcarbazole) substrate. The spots obtained were counted using a Zeiss ELISpot reader (Zeiss microscope coupled with the KS-ELISpot software).

The results of the CTL tests are shown in FIGS. 6, 7A to 9A and 10 where S1 is mouse 1, S2 is mouse 2, S3 is mouse 3, S4 is mouse 4 and S neg is the control mouse and where:

FIG. 6 shows the specific lysis percentage, as a function of the effectors/target ratio, after injection of the A peptide taking the ATL epitope as target, FIG. 7A shows the specific lysis percentage, as a function of the effectors/target ratio, after injection of the B peptide taking the B' epitope as target, FIG. 8A shows the specific lysis percentage, as a function of the effectors/target ratio, after injection of the C peptide taking the C peptide as target, FIG. 9A shows the specific lysis percentage, as a function of the effectors/target ratio, after injection of the D peptide taking the ALY epitope as target, and FIG. 10 shows the specific lysis percentage, as a function of the effectors/target ratio, after injection of the D peptide taking the ALY epitope (mice S1 and S3) as target or the ALY epitope taking the ALY epitope (mice S3 and S4) as target.

The results as shown in FIGS. 6 to 9 show that the injection of each peptide induces a cytotoxic response against the corresponding epitopes such that:

(i) both said peptides and said epitopes have an immunogenic power, and (ii) the peptides of the invention are capable of inducing immune responses specific to epitopes present in the natural infection.

It is to be noted that FIG. 10 shows that the D peptide and the epitope have identical lysis effectiveness. It is therefore clear from this experience, with regard to the quantities of peptide and epitopes used (injection of 18 nmoles of the D peptide (mice S1 and S2) and injection of 60 nmoles of the ALY epitope (mice S3 and S4), taking the ALY epitope as target), that the peptides of the invention have the advantage that they are immunogenic at doses lower than the epitopes that they contain.

The CTL test was also repeated injecting the composition ABCD or the B peptide taking the B' epitope as target and injecting the composition ABCD or the C peptide taking the C peptide as target. The results are indicated in Table 3 below.

TABLE 3

| | | | Effectors/targets ratio | |
|---|---|---|---|---|
| | | | 100:1 | 33:1 |
| Injection ABCD | Target B' | S1 | 55 | 52 |
| | | S2 | 32 | 55 |
| | | S3 | 53 | 65 |
| Injection B | | S1 | 46 | 63 |
| | | S2 | 22 | 27 |
| Injection ABCD | Target C | S1 | 52 | 69 |
| | | S2 | 1 | 67 |
| Injection C | | S1 | 2 | 9 |
| | | S2 | 0 | 0 |

The results in the above table demonstrate that injection of the combination of the 4 A, B, C and D peptides induces a cytotoxic response more effective than injection of the peptides alone.

The results of the ELISPOT tests are shown in FIGS. 7B to 9B where S1, S2 S3 and S neg have the same definitions as previously and where:

FIG. 7B shows the number of spots relative to $10^6$ cells for mice having received the B peptide relative to the B' epitope target, as well as the number of spots for the irrelevant peptide.

FIG. 9B shows the number of spots relative to $10^6$ cells for mice having received the D peptide relative to the ALY epitope target, as well as the number of spots for the irrelevant peptide.

Figure 1A:
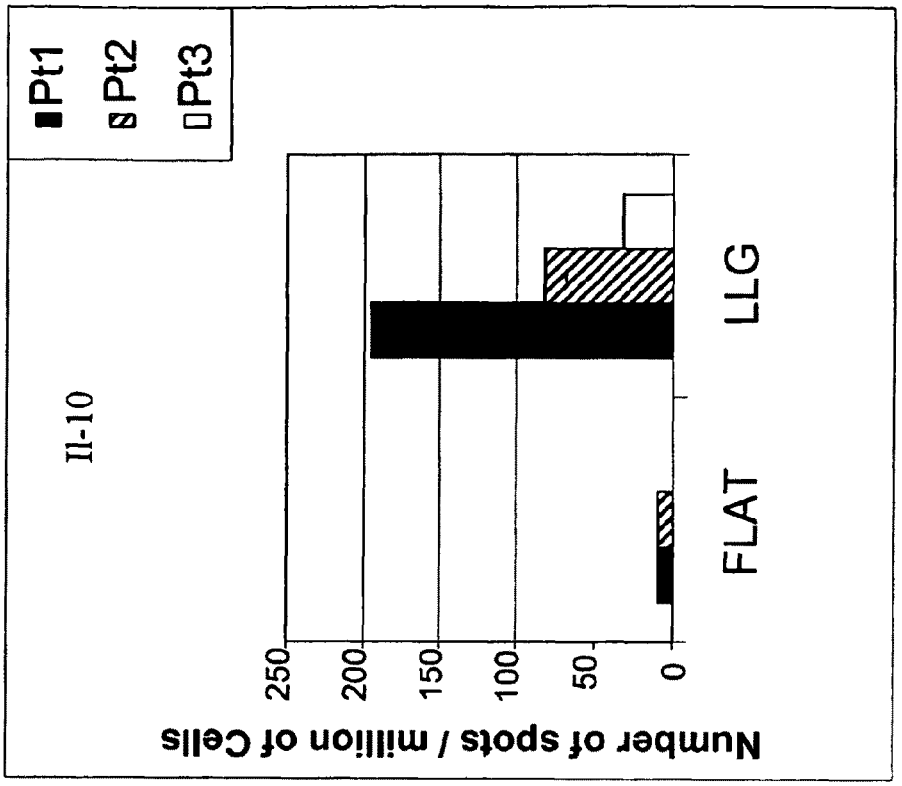
Figure 1B:
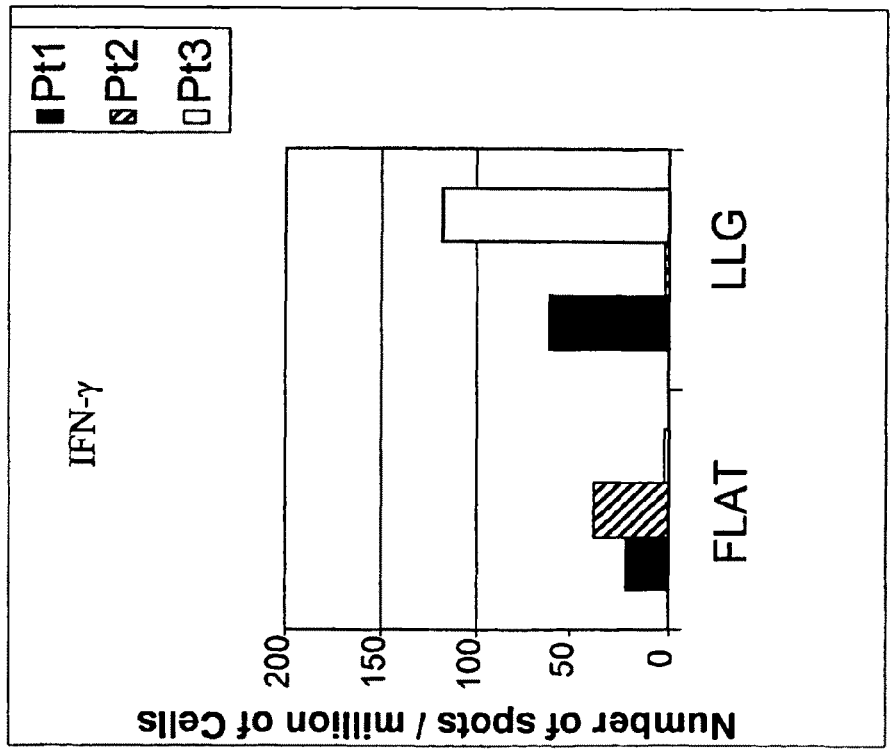
Figure 8B:
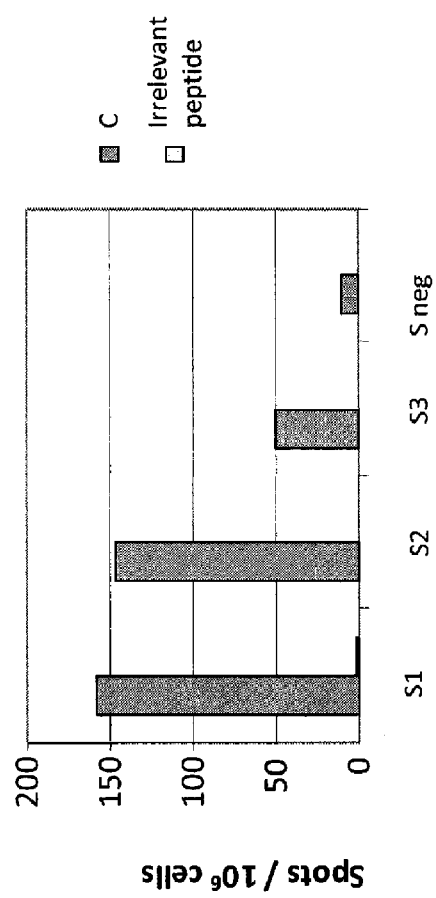
FIG. 8B shows the number of spots relative to $10^6$ cells for mice having received the C peptide relative to the C peptide target, as well as the number of spots for the irrelevant peptide.
Figure 8A:
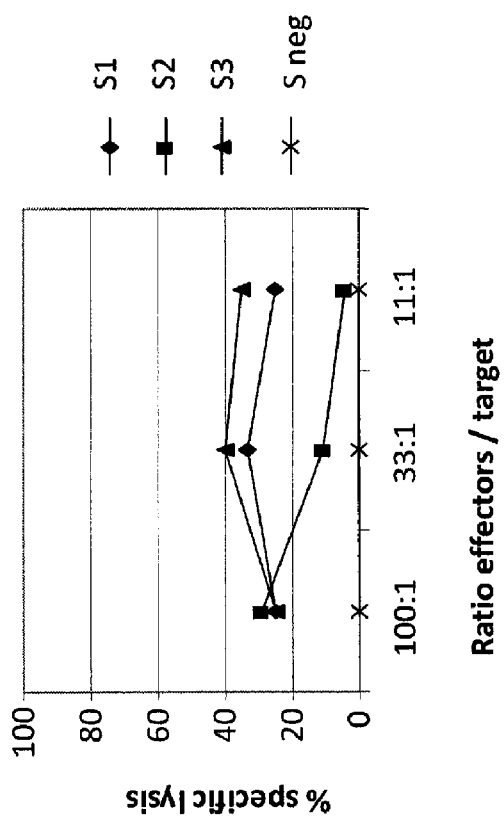
Figure 10:
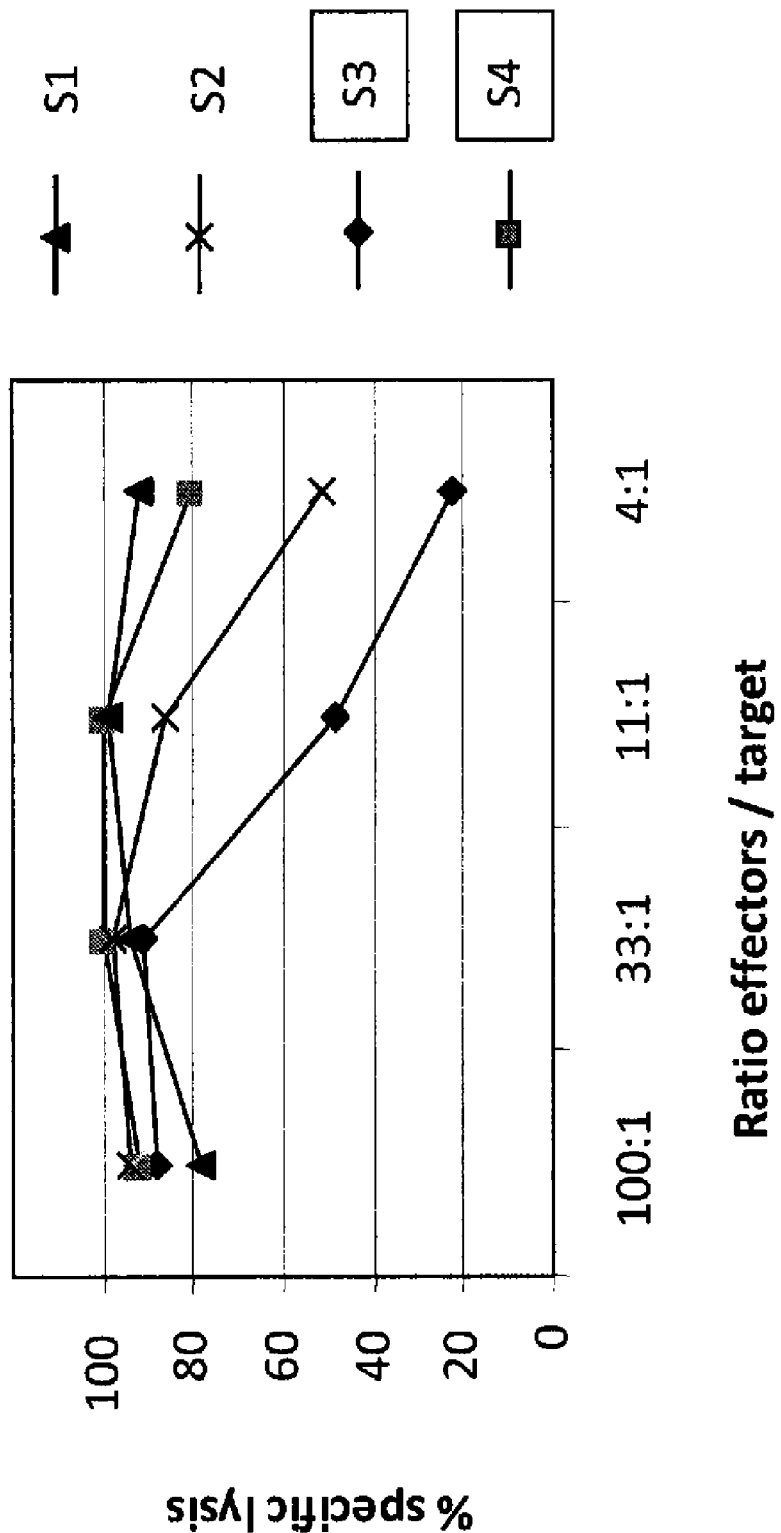
Figure 11:
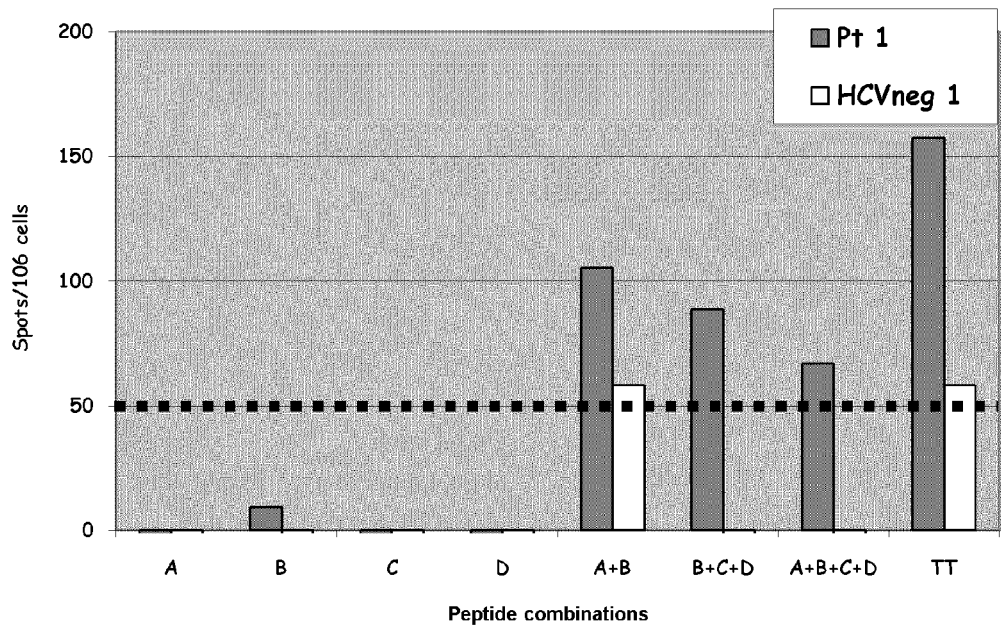
Figure 12:
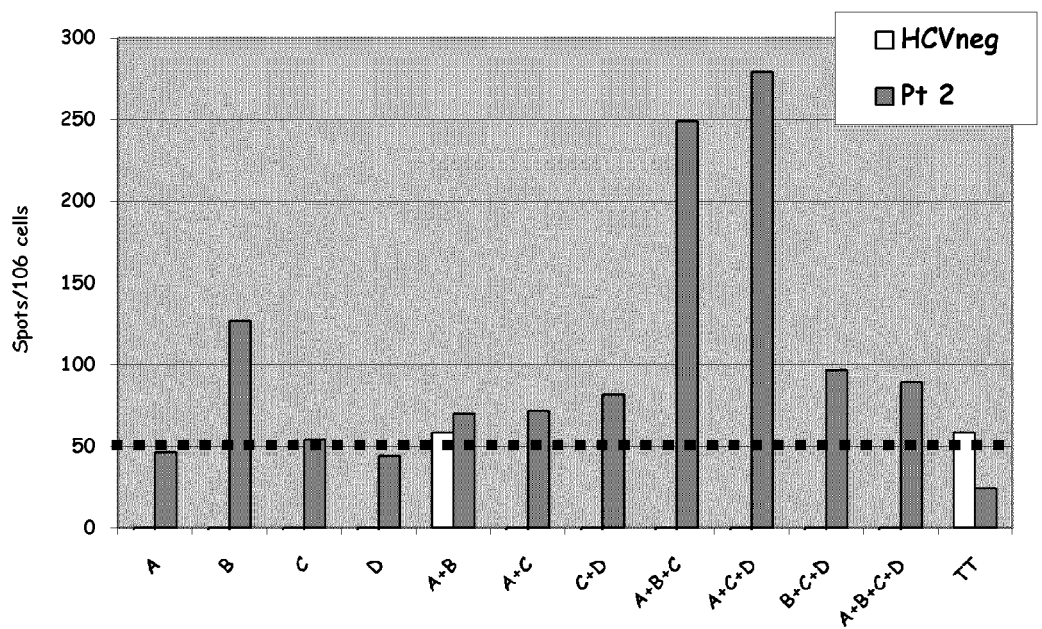
Figure 13:
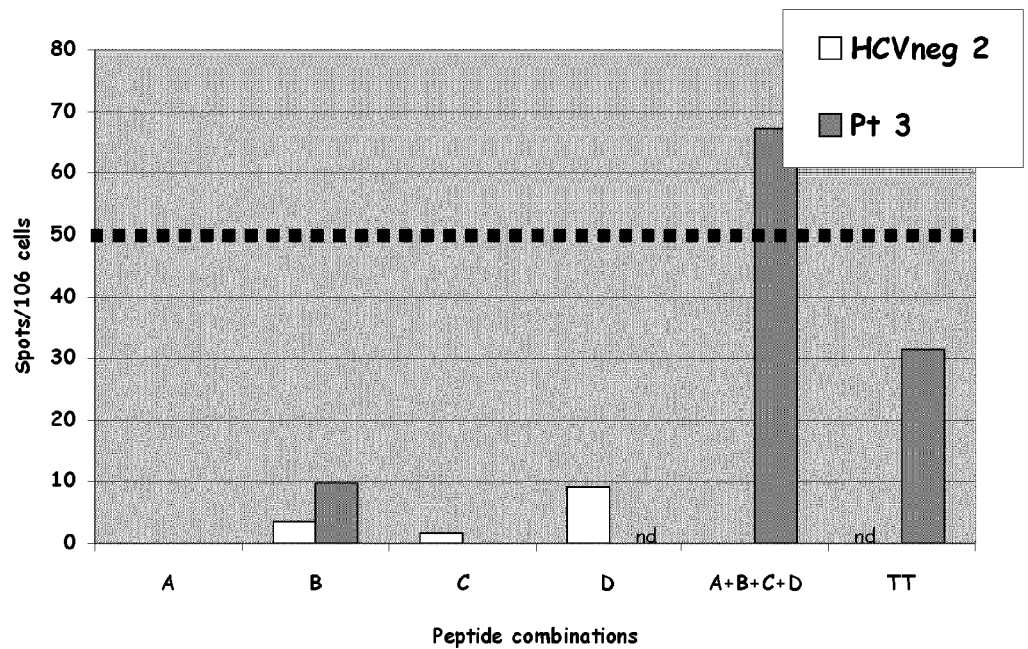
Figure 14:
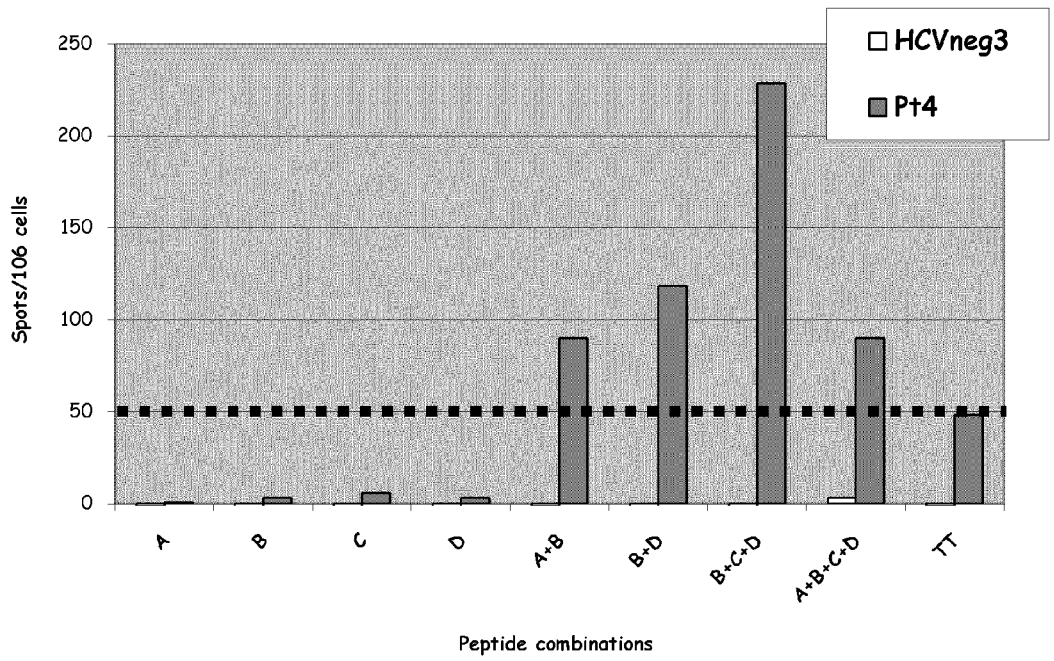

The results shown in FIGS. 7B to 9B confirm the good immunogenic power of the peptides and epitopes of the invention.

EXAMPLE 3

Demonstration of the Immunogenicity of the Peptides/Peptide Compositions of the Invention in Humans Peripheral blood mononucleated cells from four patients chronically infected by the hepatitis C virus were purified by Ficoll gradient centrifugation. Two hundred thousand cells were pre-incubated at 37° C., 5% $CO_2$, overnight in polypropylene tubes in the presence of the A to D peptides, having the amino acid sequences as defined in Example 2 above, and their compositions, in culture medium comprising $RPMI_{1640}$ (Invitrogen Life technology, Cergy Pontoise, France) supplemented with 2 mM of L-Glutamine (Invitrogen Life Technology), 50 UI/ml of penicillin (Invitrogen Life Technology), 50 µg/ml of streptomycin (Invitrogen Life Technology) and 10% of f calf serum (Hyclone, Logan, Utah, USA) according to the following Table 4:

TABLE 4

| Patient | Genotype | Clinical status | Peptides/peptide compositions |
|---|---|---|---|
| 1 | 1b | Not treated | A, B, C, D, AB, BCD, ABCD |
| 2 | 1 | Not responsive to ribavirin M12 | A, B, C, D, AB, AC, CD, ABC, ACD, BCD, ABCD |
| 3 | 4f | Not treated | A, B, C, D, ABCD |
| 4 | 1 | Not responsive to γIFN + ribavirin M6 | A, B, C, D, AB, BD, BCD, ABCD |

The peptides, alone or in combination, were present in the following concentrations: A at 10 µM, B at 5 µM, C at 1 µM and D at µM.

The cells were then transferred to an ELISPOT plate made of PVDF (polyvinylidene fluoride) previously coated with anti-γIFN antibodies according to the manufacturer's (Diaclone, Besancon, France) recommendations and incubated for another 24 hours at 37° C., 5% $CO_2$. As previously, here cytokine-producing cells are sought, which will form blue spots which are revealed, after sequential incubation with a biotinylated anti-γIFN antibody and PAL coupled to streptavidin, by degradation of the BCIP/NBT (salt of 5-bromo-4-chloro-3-indolylphosphate p-toluidine/nitroblue tetrazolium chloride) substrate and which are counted using the Zeiss ELISPOT reader.

As positive control, the peptides/peptide compositions were replaced by tetanic toxin (TT) at 1 µg/ml.

This procedure was repeated starting with cells from HCV-seronegative patients.

The results are shown in FIGS. 11 to 14 giving the number of spots per million cells as a function of the peptides and their combinations (average of the triplicates) obtained with patients 1 to 4 respectively, and in which the dotted line represents the significance threshold of the test (50 spots), Pt is patient and HCVneg is an HCV-seronegative patient.

The results demonstrate that the peptide compositions of the invention have a strong immunogenic power.

EXAMPLE 4

Minigenes Encoding a Chimeric Polypeptide Composed of the Peptides of the Invention in Fusion Induced T Cell Response in HLA-A2.1-Transgenic Mice Material and Methods Peptides The synthetic peptides used for Elispot and CTL assays were purchased from Eurogentec (Liege, Belgium). Seven peptides were generated with a purity of more than 85%, which sequences derived from the HCV-JA strain (Kato et al., 1990, Proc. Natl. Acad. Sci. USA 87: 9524-9528): ATLGFGAYM SEQ ID NO:242, GLLGCIITSL SEQ ID NO:214, CVNGVCWTV SEQ ID NO:245, LLFNILGGWV SEQ ID NO:246, SLMAFTASI SEQ ID NO:247, ALYDVVSTL SEQ ID NO:243, and RLIVFPDLGV SEQ ID NO:248, respectively referred as to ATL, GLL, CVN, LLF, SLM, ALY and RLI. They were dissolved in 100% DMSO at 10 µM and stored at −20° C. until use.

Cell Cultures

Human Huh 7 hepatoma cells were maintained at 37° C. in 5% CO2 atmosphere in complete DMEM medium containing Dulbecco's modified Eagles medium supplemented with 10% fetal calf serum, 2 mM L-Glutamine and 100 UI/ml penicillin/streptomycin (Sigma). HeLa cells (available at ATCC), a human cervix carcinoma cell line, were cultured according to supplier's instructions.

Mice

The HLA-A2.1 transgenic mice used for vaccination experiments are described in Pascolo et al. (1997, J. Exp. Med. 185: 2043-2051). These mice express a transgenic monochain histocompatibility class I molecule in which the C-terminus of the human β2-m is covalently linked to the N-terminus of a chimeric heavy chain composed of the HLA-A0201 α1 and α2 and H2-D$^b$ α3-transmembrane and intracytoplasmic domains. In addition, they are knocked out for the H2-D$^b$ and murine β2-m genes which were disrupted by homologous recombination. Mice were hosted in appropriate animal care facilities and handled following international guidelines required for experiments with animals.

Plasmids and Adenovirus Constructions

Three synthetic oligonucleotidic sequences were synthesised by Geneart (Regensburg, Germany) and cloned in pCR-Script Amp plasmids (Stratagene, La Jolla, US). The polyEp-WT minigene comprised a fusion of the wild-type nucleotide sequences (as found in the HCV JA genome) encoding B/A/C/D peptides. The polyEp-C minigene comprised a B/A/C/D encoding nucleotide sequence which codons had been optimized for translation in mammalian cells by computer software. The polyEp-E3 minigene encodes the B/A/C/D fusion with an N-terminal adenovirus E3 leader peptide (RYMILGLLALAAVCSA; SEQ ID NO: 233) for endoplasmic reticulum targeting.

The synthetic minigenes were amplified by PCR using appropriate primers incorporating a Kozack sequence and an AUG codon. The amplified sequences were inserted between the SalI and NotI sites of the gwiz plasmid (Gene Therapy System, San Diego, US), and placed under transcriptional control of the CMV promoter. The resulting gwiz constructions are named polyEp-WT, polyEp-C and polyEp-E3 respectively. A myc-tagged version was also generated. For this purpose, the above-described minigenes were inserted in the pcDNA3.1/myc-His/lacZ (Invitrogen, Carlsbad, US) in order to add a myc tag at the carboxy-terminus. The tagged minigenes were amplified by PCR as described above and inserted between SalI and NotI sites of the gwiz plasmid.

The myc-tagged minigenes were also cloned in E1-defective Ad5 vectors (kindly provided by the Gene Vector Production Network of Genethon, Paris, France), giving Ad-polyEp-WT, Ad-polyEp-C and Ad-polyEp-E3. As in the gwiz plasmids, the minigenes were placed under transcriptional control of the CMV promoter. Adenovirus stocks were produced in an appropriate packaging cell line such as 293 (Graham et al., 1977, J. Gen. Virol. 36: 59-72) or PERC.6 (Fallaux et al., 1998, Human Gene Ther. 9: 1909-1917) cells.

DNA Transfection and Adenovirus Infection

Human Huh7 cells were transfected with the different plasmid constructions described above in the presence of Lipofectamin/Plus Reagent (Invitrogen, Carlsbad, US). Briefly, $5 \times 10^5$ cells were plated in 6-well plates and 24 h later 1 µg of DNA was added to each well with Lipofectamin and Plus Reagent according to the manufacturer's instructions. HeLa or Huh7 cells were infected with the adenoviral vectors encoding the different myc-tagged minigenes at a MOI of 100. Briefly, $5 \times 10^5$ cells were plated in 6-well plates and 24 h later $5 \times 10^7$ iu of each adenovirus construction were added to each well.

Western Blot

Huh7 cells transfected by gwiz plasmids or infected with the different adenoviruses were incubated in ice-cold lysis buffer containing 1% NP40, 8M of urea and complete protease inhibitor (Roche Meyland). Lysed cells were centrifuged at 12,000 g for 10 min, and supernatants containing cytosolic fractions were assayed for protein concentrations (Comassie Blue, Pierce, Rockford, US) as described by the manufacturer. Equivalent protein amounts were loaded on a 12% acrylamide gel and run for 2 h. After electrophoretic transfer, polyvinylidene fluoride membranes (Hybond PVDF transfer membrane, Amersham, Uppsala, Sweden) were saturated and incubated with an anti-myc monoclonal antibody (dilution 1/5 000, Invitrogen, Carlsbad, US) and an anti-actin moclonal antibody (dilution 1/10 000, Sigma, Saint-Louis, US). Membranes were then incubated with an HRP-conjugated goat anti-mouse IgG antibody (1/10 000, Dako Cytomation, Glostrup, Denmark) and revealed by chemiluminescence (ECL Western-blotting Detection System, Amersham).

Immunofluorescence

Huh7 or HeLa cells were cultured and transfected or infected on coverslips in 6-well plates as previously described. 48 h post transfection or infection, cells were washed in 1×PBS, fixed with 1×PBS plus 4% paraformaldehyde followed by 1×PBS plus Glycine 0.1M and permeabilized with 1×PBS plus Triton 0.1%. Staining was carried out by sequential incubation with first anti-myc monoclonal antibody (mouse IgG, dilution 1/1000, Invitrogen, Carlsbad, US) or anti-calnexin monoclonal antibody (rabbit IgG, dilution 1/500, Stressgen, San Diego, US) for cellular localization experiments and then TRITC-conjugated goat anti-mouse IgG antibody (1/150, Sigma Aldrich) or FITC-conjugated swine anti-rabbit IgG antibody (dilution 1/40, Dako Cytomation). Antibody incubations and washes were done in PBS 1× plus BSA 0.1%. Cell nucleus were counter stained with Hoechst reagent (Sigma) at 1/200 diluted in PBS 80%-Glycerol 20%, observed using a fluorescence microscope (Zeiss, Le Pecq, France) and analysed with Adobe Photoshop 5.0.

Immunization Protocols

All plasmid DNA preparations were generated using endotoxin-free Macherey-Nagel purification columns (Macherey-Nagel, Duren, Germany) and adenovirus stocks were tested for the absence of endotoxins (Genethon, Paris, France). Six to eight week-old HLA-A2.1 transgenic mice were immunized with two intramuscular injections at 2-weeks intervals of 100 µg of gwiz plasmid, polyEp-WT, polyEp-C or polyEp-E3. Adenovirus immunization was carried out with one intramuscular injection of $10^9$ IU of Ad-polyEp-WTmyc, Ad-polyEp-Cmyc or Ad-polyEp-E3myc. Control mice were injected with an empty gwiz plasmid or a non-recombinant adenoviral vector.

Elispot Assays

Splenocytes ($2 \times 10^5$ cells per well) collected from immunized mice were cultured in triplicate for 40 h in Multiscreen plates (Millipore, France) coated with anti-mouse IFNγ monoclonal antibody (Pharmingen, France; 10 µg/ml) in complete αMEM culture medium (GIBCO BRL, France) in the presence of recombinant IL-2 (PeproTech Inc, England) at 10 U/mL alone as negative control, or with 10 µM of peptide (specific or irrelevant), or 5 µg/mL of Concavalin A as positive control. IFNγ-producing cells were quantified by cytokine-specific enzyme linked immunospot assay (ELISPOT) as previously described (Himoudi et al., 2002, J. Virol 76: 12735-12746). Each spot represents an individual IFNγ-producing cell. The number of spots in negative control was subtracted to the number of spots obtained in the experimental wells containing specific or irrelevant peptide. Results are shown as the mean value obtained for triplicate wells.

CTL Assays

CTL assays were performed as previously described (Brinster et al., 2001, Hepatology 34: 1206-1217). Briefly, spleen cells were stimulated for 7 days in the presence of 5 µM peptide and then re-stimulated on day 5 using irradiated cells loaded with 10 µM of the selected peptide. On day 7, the re-stimulated spleen cells were used as effector cells in a standard $^{51}$Cr-release assay against EL4S3-Rob HHD target cells, either loaded or not with 10 µM of the selected peptide. Effector and target cells were also used at different ratio. After 4 h incubation, $^{51}$Cr release was measured using a TopCount NXT counter (Packard). Spontaneous and total lysis were determined from wells containing target cells, loaded or not, either in medium alone or in lysis buffer (HCl 1N) respectively. Specific cytotoxicity was calculated using the formula: (release in assay−spontaneous release)/(total lysis−spontaneous release)×100. For each effector/target cell ratio, results are shown as the mean percentage of specific lysis obtained from duplicate points.

Listeria Monocytogenes Infectious Challenge

A recombinant and kanamycin-resistant *Listeria Monocytogenes* expressing the HCV NS3 protein (named TC-LNS3; Simon et al., 2003, Infect. Immunol. 71, 6372-6380) was inoculated intravenously to immunized mice 15 days after adenovirus immunization (an intramuscular administration of $10^9$ IU/mice as described above). Mice were anaesthetized and received from 1 to 2 LD50 of TC-LNS3 (ILD50=9.10$^7$ pfu). Two days later, mice were sacrificed and pieces of liver and spleen were removed and weighted. The collected organ samples were homogenized in PBS/Tween 0.05% and residual bacterial titers were determined by serial dilution on BHI-agar plates (containing 30 µg/mL kanamycin). After 48 to 60 h of culture at room temperature, colonies obtained on plates were numerated and titers corresponding to numbers of bacteria per mg of organs were calculated.

Results

Both CD8+ and CD4+ lymphocytes mediated immune responses play a critical role in the outcome of HCV infection. Examples 2 and 3 demonstrate the capacity of four HCV peptides from non-structural protein NS3 (A and B peptides), NS4 (C peptide) and NS5B (D peptide) of inducing T cell responses alone or in various combinations in natural infection (Example 3) or in a transgenic mouse model (Example 2).

The four peptides were combined in a unique chimeric fusion peptide of 137 amino acids having the amino acid sequence disclosed in SEQ ID NO: 234 and comprising from N to C terminus B/A/C/D peptides (plus an initiator Met). Three minigene constructs were generated, respectively polyEp-WT, polyEp-C and polyEp-E3 which encode the same chimeric B/A/C/D fusion peptide but differ at the nucleotide level. The polyEp-WT construct comprises the "natural" nucleotide sequence as found in the HCV-JA genome encoding the 4 peptides fused in the B/A/C/D combination (SEQ ID NO: 235). In polyEp-C, the nucleotide sequence encoding each of the peptide has been optimized for translation in mammalian cells (SEQ ID NO: 236). The polyEp-E3 construct (SEQ ID NO: 237) encodes the B/A/C/D fusion preceded at its N-terminus by the leader sequence of the adenovirus E3 protein for endoplasmic reticulum (ER) targeting of the resulting 154 amino acid long polypeptide (Met+16 amino acid E3 leader sequence+137 amino acid B/A/C/D fusion). The minigene constructs were cloned in gwiz DNA plasmids and E1-defective adenovirus vectors under control of the CMV promoter in both cases.

Expression of the minigene products was evaluated by Western blot and immunofluorescence in Huh 7 cells transfected or infected with myc-tagged minigene vectors. Huh 7 cells transfected with an empty gwiz plasmid or infected with a non-recombinant adenoviral vector were used as negative controls. Myc-tagged fusion peptides were revealed using an anti-myc monoclonal antibody with or without MG132 proteasome inhibitor. Western blot analysis revealed a unique band having the expected molecular weight of approximately 16 KD for the fusion peptide encoded by polyEp-WT and polyEp-C and approximately 17 KD for the fusion peptide encoded by polyEp-E3. As expected, no proteins were highlighted in Huh 7 negative controls. Optimization of the minigene codons for mammalian translation does not result in a significant improvement of expression (approximately same level of expression in Huh 7 cells transfected with polyEp-WT plasmid as in Huh 7 cells transfected with polyEp-C). Interestingly, addition of the ER targeting E3 leader signal provides a partial protection from proteasome degradation as illustrated by the fusion peptide detected in the absence of MG132 in samples collected from Huh7 transfected polyEp-E3-encoding plasmid.

Immunofluorescence analysis confirmed expression of the minigene products in Huh 7 and HeLa transfected cells. Interestingly, fusion peptides encoded by polyEp-WT and polyEp-C plasmids showed a cytoplasmic localization whereas ER localisation is suggested for the fusion peptide encoded by polyEp-E3.

Figure 15A:
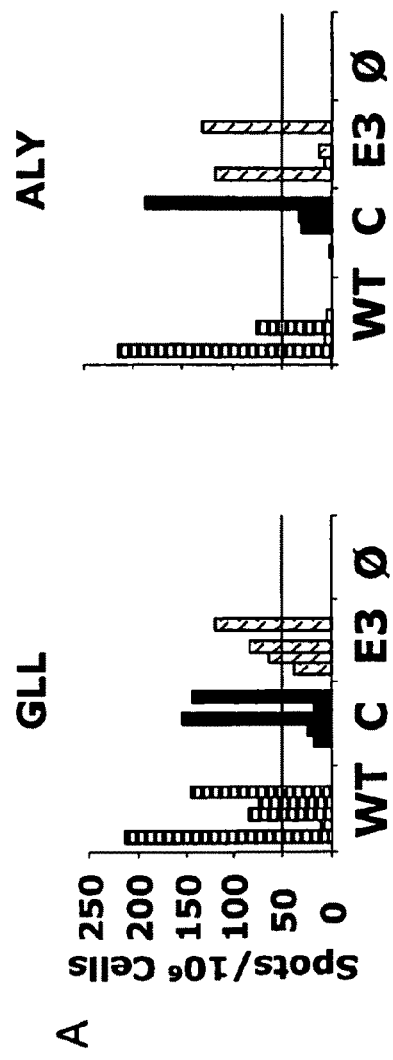

The immunogenic activity of the fusion peptides was evaluated in HLA-A2.1 transgenic mice immunized by two intramuscular injections at two weeks interval of plasmids encoding polyEp-WT, polyEp-C or polyEp-E3 (100 µg/injection/mouse). Specific anti-HCV T cell responses were analysed 15 days after the last immunization by Elispot and CTL assays against 7 HLA-A2 restricted epitopes contained in the fusion peptides, respectively ATL, GLL, CVN, LLF, SLM, ALY and RLI. As illustrated in FIG. 15A, the minigene-encoding gwiz plasmids are able to induce IFNγ producing cells specific of 2 out of the 7 tested epitopes, GLL and ALY epitopes. More specifically, GLL-specific responses ranged from 75 to 212 spots per $10^6$ cells for 4 out of 6 mice immunized with polyEp-WT plasmid, from 142 to 153 spots per $10^6$ cells for 2 out of 6 mice immunized with polyEp-C plasmid and from 64 to 118 spots per $10^6$ cells for 3 out of 6 mice immunized with polyEp-E3 plasmid. Specific responses against ALY epitope are also detected with number of spots per $10^6$ cells ranging from 75 to 215 spots for 2 out of 6 mice for polyEp-WT and from 117 to 130 spots for 2 out of 6 mice for polyEp-E3. For polyEp-C, only 1 out of 6 mice displayed ALY-specific IFNγ producing cells (187 spots). As expected no specific IFNγ producing cells are revealed against the irrelevant epitope (data not shown). The absence of specific responses against the 5 other HCV-specific epitopes can be explained by the fact that these epitopes are usually poor inducers of IFNγ producing cells in the HLA-A2.1 transgenic mouse model (Himoudi et al, 2002, J. Virol. 76, 12735-12746; Martin et al., 2004, J. Med. Virol. 74, 397-405).

Specific cytolytic responses were also characterized by CTL assays in HLA-A2.1 transgenic mice twice immunized with minigene-encoding plasmids. Interestingly, as illustrated in FIG. 16A, cytolytic responses targeted a larger number of epitopes than IFNg-producing T cells. The polyEp-WT plasmid induced cytolytic responses specific of 4 epitopes, ATL, GLL, CVN and ALY (with GLL and ALY-specific lysis higher than 45% in all immunized mice). The cytolytic responses obtained after immunization with PolyEp-C plasmid targeted three HCV epitopes, ATL, CVN and ALY with the stronger responses being generated with CVN (45% to 62% of specific lysis for 2 out of 3 mice). Immunization with PolyEp-E3 plasmid induced cytolytic responses specific of ATL, GLL and ALY which are similar as those obtained after injections of PolyEp-WT plasmid. Specific lysis higher than 50% was obtained against GLL and ALY in all immunized animals (from 51% to 77% of specific lysis against GLL for 3 out of 3 mice and from 50% to 68% of specific lysis against ALY for 3 out of 3 mice).

Figure 15B:
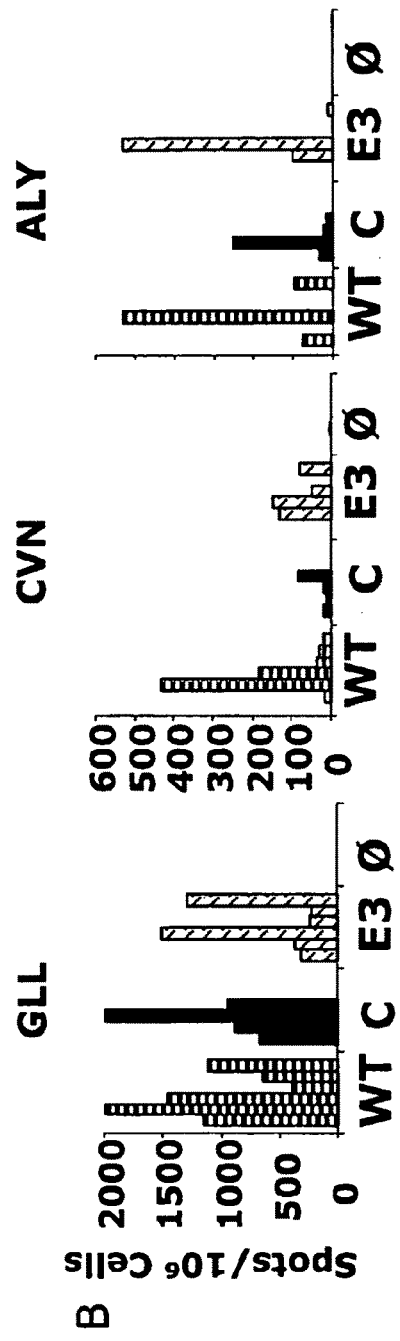

Immunogenicity of minigene-encoded fusion peptide was also evaluated in transgenic HLA-A2.1 immunized with an intramuscular injection of Ad-polyEp-WT, Ad-polyEp-C or Ad-polyEp-E3. As illustrated in FIG. 15B, Elispot assays revealed a strong specific immune response against GLL, CVN and ALY epitopes. GLL-specific responses were detected in all vaccinated mice and ranged from 395 to 1988 spots, from 660 to 1978 spots and from 237 to 1504 spots per $10^6$ cells, respectively in Ad-polyEp-WT, Ad-polyEp-C and Ad-polyEp-E3 immunized mice. CVN-specific IFNγ producing cells were detected in 2 out of 6 Ad-polyEp-WT injected mice (from 184 to 430 spots per $10^6$ cells), and 4 out of 6 Ad-polyEp-E3 injected mice (from 53 to 146 spots per $10^6$ cells). ALY-specific IFNγ producing cells were detected in 3 out of 6 Ad-polyEp-WT injected mice (from 74 to 531 spots per $10^6$ cells), and 2 out of 6 Ad-polyEp-E3 injected mice (from 103 to 531 spots per $10^6$ cells). Only 1 out of 6 mice immunized with Ad-polyEp-C displayed IFNγ producing cells specific of CVN (85 spots/$10^6$ cells) and of ALY (252 spots/$10^6$ cells).

Cytolytic immune responses were measured by CTL assays against five HLA-A2 epitopes, four low inducer epitopes in DNA immunization assays (ATL, SLM, LLF and RLI) and a potent inducer epitope (CVN). After injection of the different minigene-encoding adenoviruses, no specific cytolytic response could be observed against SLM and RLI peptides. As illustrated in FIG. 16B, moderate cytolytic responses were detected against ATL in animals immunized with Ad-polyEp-WT and Ad-polyEp-E3 (specific lysis ranging from 27% to 38% for 1 to 2 mice out of 3) whereas no anti-ATL response was obtained following immunization with Ad-polyEp-C. In contrast, high CVN-specific cytolytic responses were detected following injection of minigene-encoding adenoviruses (39% to 46% of specific lysis in 2 out of 3 Ad-polyEp-WT-injected mice; 54% to 63% of specific lysis in the 3 mice injected with Ad-polyEp-C and 45 to 59% of specific lysis in the Ad-polyEp-E3-injected mice).

The protective immunity conferred by the fusion peptides was evaluated in HLA-A2.1 transgenic mice immunized with the different minigene-encoding adenoviruses during a recombinant *Listeria* surrogate challenge assay. Mice received an intramuscular injection of Ad-polyEp-WT, Ad-polyEp-C or Ad-polyEp-E3 at Day 0 and were challenged by intravenous injection of TC-LNS3 15 days later. Control mice are injected under the same condition with a non-recombinant (i.e. empty) adenovirus. Mice were sacrificed two days after the challenge and residual bacterial titers were determined in spleens and livers. The results show that Ad-polyEp-WT and Ad-polyEp-E3 immunisations allowed a significant decrease of TC-LNS3 residual titers in spleen as compared to control mice. Based on the average titers observed for each group, this decrease is about 1 log for Ad-polyEp-WT and about 2 logs for Ad-polyEp-E3 as compared to empty adenovirus (p=0.0253 and p=0.0143 respectively, according to Mann Whitney statistical analysis). In livers, a significant decrease of TC-LNS3 residual titers was observed only for Ad-polyEp-E3 immunised mice (about 1.5 log of decrease considering the mean of each group) compared to control mice immunised with an empty adenoviral vector (p=0.0143 according to Mann Whitney statistical analysis).

In conclusion, immunization with DNA plasmids encoding the B/A/C/D fusion peptide was able to induce both IFNγ producing cells and cytolytic responses respectively directed against 2 to 4 HLA-A2 restricted epitopes, depending on the constructions and the assays employed. Equivalent induced T cell responses are observed for the three minigenes under the experimental conditions tested and codon optimization did not lead to any improvement. Interestingly, adenovirus vectorization induced the strongest T cell responses. More specifically, immunization with adenovirus vectors permits to broader spectrum of HLA-A2 restricted epitopes recognized by IFNγ-producing cells (2 epitopes out of 7 recognized after DNA immunization against 3 after Adenovirus immunization) and to maximize both the cytolytic and the IFNγ producing cell-mediated immune responses (higher level of specific lysis and higher number of spots when the mice are injected with the minigene-encoding adenoviruses than with DNA plasmids). A protective immunity was conferred by Ad-polyEp-WT and Ad-polyEp-E3 against a recombinant *Listeria* expressing the NS3 protein. Based on these results, vectorized minigenes encoding the B/A/C/D fusion peptide are potential HCV vaccine candidates.

The invention claimed is:

1. A viral vector comprising a nucleotide sequence coding a fusion peptide comprising a fusion of at least four peptides chosen from the group consisting of A, B, C, and D peptides, B' and C' epitopes, as well as a regulatory element necessary for its expression, wherein:
the A peptide is SEQ ID NO:3;
the B peptide is SEQ ID NO:47;
the C peptide is SEQ ID NO:129;
the D peptide is SEQ ID NO:176;
the B' epitope is SEQ ID NO:214; and
the C' epitope is SEQ ID NO:222.

2. The expression vector according to claim 1, wherein said vector is a replication-defective adenoviral vector.

3. The expression vector according to claim 1, wherein said vector is a MVA vaccinia vector.

4. An isolated microorganism or an isolated host cell transformed by an expression vector as defined in claim 1.

5. The viral vector according to claim 1, wherein the fusion peptide comprises a fusion of the four A to D peptides.

6. The viral vector according to claim 1, wherein the fusion peptide comprises a fusion of the A to D peptides, with a B peptide located at the N-terminus of the fusion, which is fused to a A peptide, which is fused to a C peptide, which is fused to a D peptide.

7. The viral vector according to claim 6, wherein the fusion peptide comprises the amino acid sequence defined in SEQ ID NO: 234.

8. An immunogenic composition, containing as active ingredient at least a viral vector according to claim 1, or at least a microorganism or a host cell transformed by said vector, in combination with a pharmaceutically appropriate vehicle.

* * * * *